US011059794B2

(12) United States Patent
Mattei et al.

(10) Patent No.: US 11,059,794 B2
(45) Date of Patent: Jul. 13, 2021

(54) HETEROCYCLIC COMPOUNDS USEFUL AS DUAL ATX/CA INHIBITORS

(71) Applicant: Hoffmann-La Roche Inc., Little Falls, NJ (US)

(72) Inventors: Patrizio Mattei, Basel (CH); Jérôme Hert, Basel (CH); Daniel Hunziker, Basel (CH); Markus Rudolph, Basel (CH); Petra Schmitz, Basel (CH); Patrick Di Giorgio, Basel (CH); Justin Gomme, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/569,475

(22) Filed: Sep. 12, 2019

(65) Prior Publication Data

US 2020/0002297 A1    Jan. 2, 2020

Related U.S. Application Data

(63) Continuation of application No. PCT/EP2018/056140, filed on Mar. 13, 2018.

(30) Foreign Application Priority Data

Mar. 16, 2017 (EP) ..................................... 17161249

(51) Int. Cl.

| | | |
|---|---|---|
| *C07D 257/04* | (2006.01) | |
| *C07D 401/06* | (2006.01) | |
| *C07D 401/10* | (2006.01) | |
| *C07D 401/12* | (2006.01) | |
| *C07D 401/14* | (2006.01) | |
| *C07D 403/10* | (2006.01) | |
| *C07D 405/12* | (2006.01) | |
| *C07D 405/14* | (2006.01) | |
| *C07D 409/14* | (2006.01) | |
| *C07D 417/14* | (2006.01) | |

(52) U.S. Cl.
CPC ......... *C07D 257/04* (2013.01); *C07D 401/06* (2013.01); *C07D 401/10* (2013.01); *C07D 401/12* (2013.01); *C07D 401/14* (2013.01); *C07D 403/10* (2013.01); *C07D 405/12* (2013.01); *C07D 405/14* (2013.01); *C07D 409/14* (2013.01); *C07D 417/14* (2013.01)

(58) Field of Classification Search
CPC .. C07D 257/04; C07D 401/06; C07D 401/10; C07D 401/12; C07D 401/14; C07D 403/10; C07D 405/12; C07D 405/14; C07D 409/14; C07D 417/14
See application file for complete search history.

(56) References Cited

U.S. PATENT DOCUMENTS

| | | |
|---|---|---|
| 3,392,149 A | 7/1968 | von der Emden et al. |
| 5,202,322 A | 4/1993 | Allen et al. |
| 5,238,942 A | 8/1993 | Chakravarty et al. |
| 5,240,928 A | 8/1993 | Allen et al. |
| 5,290,780 A | 3/1994 | Venkatesan et al. |
| 5,304,565 A | 4/1994 | Morimoto et al. |
| 5,358,951 A | 10/1994 | Levin et al. |
| 5,470,975 A | 11/1995 | Atwal et al. |
| 5,472,961 A | 12/1995 | Gottschlich et al. |
| 5,532,243 A | 7/1996 | Gilligan |
| 6,821,964 B2 | 11/2004 | Colon-Cruz et al. |
| 6,841,560 B2 | 1/2005 | Thompson et al. |
| 7,271,260 B2 | 9/2007 | Lee et al. |
| 8,329,907 B2 | 12/2012 | Schultz et al. |
| 8,440,694 B2 | 5/2013 | Turner et al. |
| 8,697,883 B2 | 4/2014 | Abouabdellah et al. |
| 8,841,324 B2 | 9/2014 | Staehle et al. |
| 8,946,264 B2 | 2/2015 | Shinozuka et al. |
| 9,029,387 B2 | 5/2015 | Staehle et al. |
| 9,493,486 B2 | 11/2016 | Hunziker et al. |
| 9,580,434 B2 | 2/2017 | Mazurov et al. |
| 9,598,418 B2 | 3/2017 | Srivastava et al. |
| 9,802,944 B2 | 10/2017 | Di Giorgio et al. |
| 10,208,052 B1 | 2/2019 | Zheng et al. |

(Continued)

FOREIGN PATENT DOCUMENTS

| | | |
|---|---|---|
| CA | 2768095 | 1/2011 |
| CA | 2878442 A1 | 4/2014 |

(Continued)

OTHER PUBLICATIONS

CAS Registry Database, 1352926-14-7,Database Registry [retrieved online May 25, 2016] Chemical Abstracts Service Jan. 12, 2012 (Jan. 12, 2012), All i chern LLC: XP002707617, retrieved from STN Database accession No. 1352926-14-7 see also RN: 135295-74-6; the whole document.

(Continued)

*Primary Examiner* — Erich A Leeser
(74) *Attorney, Agent, or Firm* — Katherine J. Mackenzie

(57) ABSTRACT

The invention provides novel compounds having the general formula (I)

$$Y-N\underset{R^1}{\overset{m}{\diamond}}X-W \quad (I)$$

$R^2$ wherein $R^1$, $R^2$, Y, X, W, m and n are as defined herein, compositions including the compounds and methods of using the compounds.

35 Claims, No Drawings

(56) References Cited

U.S. PATENT DOCUMENTS

| | | |
|---|---|---|
| 10,550,150 B2 | 2/2020 | Desai et al. |
| 10,633,384 B2 | 4/2020 | Hunziker et al. |
| 10,640,472 B2 | 5/2020 | Hert et al. |
| 10,647,719 B2 | 5/2020 | Di Giorgio et al. |
| 10,654,857 B2 | 5/2020 | Di Giorgio et al. |
| 10,669,268 B2 | 6/2020 | Hert et al. |
| 10,669,285 B2 | 6/2020 | Hunziker et al. |
| 10,676,446 B2 | 6/2020 | Hert et al. |
| 10,738,053 B2 | 8/2020 | Hert et al. |
| 10,787,459 B2 | 9/2020 | Di Giorgio et al. |
| 10,800,786 B2 | 10/2020 | Mattei et al. |
| 2005/0203112 A1 | 9/2005 | Castonguay et al. |
| 2006/0074078 A1 | 4/2006 | Prevost et al. |
| 2008/0090802 A1 | 4/2008 | Letourneau et al. |
| 2010/0222341 A1 | 9/2010 | Schiemann et al. |
| 2010/0298290 A1 | 11/2010 | Kumar et al. |
| 2011/0230471 A1 | 9/2011 | Staehle et al. |
| 2012/0015959 A1 | 1/2012 | Staehle et al. |
| 2012/0015976 A1 | 1/2012 | Schultz et al. |
| 2012/0095040 A1 | 4/2012 | Abouabdellah et al. |
| 2012/0115852 A1 | 5/2012 | Schultz et al. |
| 2012/0115858 A1 | 5/2012 | Tesconi et al. |
| 2015/0252046 A1 | 9/2015 | Staehle et al. |
| 2015/0353559 A1 | 12/2015 | Hert et al. |
| 2015/0376194 A1 | 12/2015 | Hert et al. |
| 2016/0264586 A1 | 9/2016 | Mattei et al. |
| 2017/0008900 A1 | 1/2017 | Di Giorgio et al. |
| 2017/0008913 A1 | 1/2017 | Hunziker et al. |
| 2017/0029425 A1 | 2/2017 | Hunziker et al. |
| 2017/0050960 A1 | 2/2017 | Hert et al. |
| 2018/0029996 A1 | 2/2018 | Hert et al. |
| 2018/0118741 A1 | 5/2018 | Hert et al. |
| 2018/0208601 A1 | 7/2018 | Hert et al. |
| 2018/0208602 A1 | 7/2018 | Di Giorgio et al. |
| 2018/0215765 A1 | 8/2018 | Di Giorgio et al. |
| 2018/0258095 A1 | 9/2018 | Hert et al. |
| 2018/0280352 A1 | 10/2018 | Mattei et al. |
| 2018/0312515 A1 | 11/2018 | Mattei et al. |
| 2018/0327410 A1 | 11/2018 | Grice et al. |
| 2018/0327416 A1 | 11/2018 | Grice et al. |
| 2019/0144457 A1 | 5/2019 | Di Giorgio et al. |
| 2020/0002297 A1 | 1/2020 | Mattei et al. |
| 2020/0002336 A1 | 1/2020 | Hert et al. |
| 2020/0079779 A1 | 3/2020 | Di Giorgio et al. |
| 2020/0087307 A1 | 3/2020 | Mattei et al. |
| 2020/0199155 A1 | 6/2020 | Hunziker et al. |
| 2020/0207769 A1 | 7/2020 | Hunziker et al. |
| 2020/0216457 A1 | 7/2020 | Di Giorgio et al. |
| 2020/0223854 A1 | 7/2020 | Di Giorgio et al. |
| 2020/0291038 A1 | 9/2020 | Hert et al. |
| 2020/0317624 A1 | 10/2020 | Hert et al. |
| 2020/0339522 A1 | 10/2020 | Hert et al. |
| 2020/0339570 A1 | 10/2020 | Hert et al. |

FOREIGN PATENT DOCUMENTS

| | | |
|---|---|---|
| CN | 1068114 A | 1/1993 |
| CN | 1751047 A1 | 3/2006 |
| CN | 102459207 A | 5/2012 |
| CN | 103237799 A | 8/2013 |
| CN | 104428299 A | 3/2015 |
| CN | 104918917 A | 9/2015 |
| EP | 0417631 A2 | 3/1991 |
| EP | 0 424 850 A1 | 5/1991 |
| EP | 2301936 A1 | 3/2011 |
| EP | 3 187 492 A1 | 7/2017 |
| EP | 3385261 A1 | 10/2018 |
| JP | 2001-039950 | 2/2001 |
| JP | 2005-239708 | 9/2005 |
| JP | 2007-176809 | 7/2007 |
| JP | 2008-501743 | 1/2008 |
| JP | 2008-31064 | 2/2008 |
| JP | 2008-031064 A | 2/2008 |
| JP | 2008-531533 | 8/2008 |
| JP | 2008-5405477 | 11/2008 |
| JP | 2009/161449 | 7/2009 |
| JP | 2011-502150 | 1/2011 |
| KR | 2006-0088557 | 8/2006 |
| RU | 2375352 C2 | 12/2009 |
| RU | 2 480 463 | 4/2013 |
| RU | 2 483 068 | 5/2013 |
| RU | 2 517 693 | 5/2014 |
| WO | 99/40070 | 8/1999 |
| WO | 01/30780 | 5/2001 |
| WO | 02/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/049771 | 5/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2009/046841 A2 | 4/2009 |
| WO | 2009/054914 A1 | 4/2009 |
| WO | 2009/058347 | 5/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108268 | 9/2010 |
| WO | 2010/108651 | 9/2010 |
| WO | 2010/112116 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2009/154132 | 12/2011 |
| WO | 2011/151461 A2 | 12/2011 |
| WO | 2012/020008 A1 | 2/2012 |
| WO | 2012/024620 | 2/2012 |
| WO | 2012/028243 | 3/2012 |
| WO | 2012/080727 A1 | 6/2012 |
| WO | 2012/166415 A1 | 12/2012 |
| WO | 2013/033059 A1 | 3/2013 |
| WO | 2013/054185 A1 | 4/2013 |
| WO | 2013/064467 A1 | 5/2013 |
| WO | 2013/065712 A1 | 5/2013 |
| WO | 2013/079223 A1 | 6/2013 |
| WO | 2013/175053 | 11/2013 |
| WO | 2013/186159 A1 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |

(56) References Cited

FOREIGN PATENT DOCUMENTS

| WO | 2014/066659 | | 5/2014 | | |
| --- | --- | --- | --- | --- | --- |
| WO | 2014/102817 | A1 | 7/2014 | | |
| WO | 2014/133112 | A1 | 9/2014 | | |
| WO | 2014/139324 | | 9/2014 | | |
| WO | 2014/139978 | A1 | 9/2014 | | |
| WO | 2014/143579 | | 9/2014 | | |
| WO | 2014/152725 | A1 | 9/2014 | | |
| WO | WO 2014/139978 | * | 9/2014 | ........... | C07D 471/04 |
| WO | 2014/164905 | | 10/2014 | | |
| WO | 2014/179564 | | 11/2014 | | |
| WO | 2015/008230 | A1 | 1/2015 | | |
| WO | 2015/058031 | | 4/2015 | | |
| WO | 2015/077503 | A1 | 5/2015 | | |
| WO | 2015/078800 | A1 | 6/2015 | | |
| WO | 2015/078803 | | 6/2015 | | |
| WO | 2015/144480 | A1 | 10/2015 | | |
| WO | 2015/144605 | A1 | 10/2015 | | |
| WO | 2015/144609 | A1 | 10/2015 | | |
| WO | 2015/144803 | A1 | 10/2015 | | |
| WO | 2015/154023 | A1 | 10/2015 | | |
| WO | 2016/031987 | | 3/2016 | | |
| WO | 2016/061160 | A1 | 4/2016 | | |
| WO | 2016/128529 | A1 | 8/2016 | | |
| WO | 2016/162390 | | 10/2016 | | |
| WO | 2017/005073 | A1 | 1/2017 | | |
| WO | 2017/037146 | | 3/2017 | | |
| WO | 2017/037670 | A1 | 3/2017 | | |
| WO | 2017/050732 | A1 | 3/2017 | | |
| WO | 2017/050747 | A1 | 3/2017 | | |
| WO | 2017/050791 | A1 | 3/2017 | | |
| WO | 2017/050792 | A1 | 3/2017 | | |
| WO | 2017/053722 | A1 | 3/2017 | | |
| WO | 2017/091673 | A2 | 6/2017 | | |
| WO | 2018/167001 | A1 | 9/2018 | | |
| WO | 2018/167113 | A1 | 9/2018 | | |

OTHER PUBLICATIONS

CAS Registry Database, 959567-58-9, pp. 1-38, Dec. 26, 2007.
959567-58-9,CAS Database Registry [retrieved online May 25, 2016] Chemical Abstracts Service Dec. 26, 2007 (Dec. 26, 2007), NIH Chemical Genomics Center: XP002707620, retrieved from STN Database accession No. 959567-58-9.
Albers et al., "Chemical Evolution of Autotaxin Inhibitors" Chem Rev 112(5):2593-2603 (May 9, 2012).
Albers et al., "Structure-Based Design of Novel Boronic Acid-Based Inhibitors of Autotaxin" J Med Chem 54(13):4619-4626 ( 2011).
Albers, H., et al., "Discovery and Optimization of Boronic Acid Based Inhibitors of Autotaxin" J Med Chem 53:4958-4967 (Jun. 10, 2010).
Anderson, "The Process of Structure-Based Drug Design" Chem & Biol 10:787-797 (Sep. 2003).
Angeli et al., "Synthesis and carbonic anhydrase inhibition of polycyclic imides moieties" Bioorgan Med Chem 25(20):5373-5379 (Oct. 20, 2017).
Armstrong, J., et al., "Purification and Properties of Human Erythrocyte Carbonic Anhydrases" J Biol Chem 241(21):5137-5149 (Nov. 10, 1966).
Balbayianni Efrosini, "Autotaxin inhibitors:a patent review" Expert Opin Ther Pat 23(9):1123-1132 (Sep. 1, 2013).
Benesch, Matthew G.K., et al., "Autotaxin in the crosshairs: Taking aim at cancer and other inflammatory conditions" FEBS Lett 588:2712-2727 (Feb. 19, 2014).
Bora, Rajesh O., et al., "[1, 2, 4]-Oxadiazoles: Synthesis and Biological Applications" Mini-Rev in Med. Chem 14(4):355-369 (Mar. 13, 2014).
CAS Database Registry, ID#1206969-43-8 [retrieved online May 25, 2016], Feb. 22, 2010 (Feb. 22, 2010), BroadPharm:, retrieved from STN Database accession No. 1206969-43-8 the whole document.

CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.
Database Capulus (online) Chemical Abstracts Service Columbus Ohio, 1993, Database accession No. 1994:483155 RN156411-73-3, 156411-74-4 (1993).
Erdik, Ender, "Transition Metal Catalyzed Reactions of Organozinc Reagents" Tetrahedron Rep No. 23 48(44):9577-9648 (Jan. 1, 1992).
Farina, V. et al. Organic Reactions "The Stille Reaction" Paquette, Leo A., New York—US: Wiley and Sons, vol. 50:1-704 (Apr. 1, 1997).
Garcia-Gutierrez et al., "Novel inhibitors to Taenia solium Cu/Zn superoxide dismutase identifed by virtual screening" J. Comp Aided Molecular Design 25:1135-1145 (2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Green et al. Protective Groups in Organic Synthesis (Table of Contents only, in 4 pages), Second edition, New York: John Wiley & Sons, Inc., ( 1991).
Hall, Dennis.. ed. et al. Boronic Acids: Preparation, Applications in Organic Synthesis and Medicine (Description and table of contents only, 2 pages), Hall, Dennis,Wiley,:1-571 (Jan. 1, 2006).
Hemming, K. Science of Synthesis, Product 13: 1, 2, 3-Triazoles "Product Class 6: 1,2,4-Oxadiazoles" Storr, R.C. & Gilchrist, T.L., eds., Stuttgart—DE: Thieme Verlagsgruppe, vol. 113:127-184 (Jan. 1, 2004).
Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
Hoeglund et al., "Optimization of a pidemidic acid autotaxin inhibitor" J Med Chem 153:1056-1066 (Dec. 30, 2009).
"International Preliminary Report on Patentability—PCT/EP2018/056140":pp. 1-8 (dated Sep. 26, 2019).
"International Search Report—PCT/EP2014/054631":pp. 1-4 (dated Apr. 15, 2014).
"International Search Report—PCT/EP2014/075360":pp. 1-5 (dated Feb. 9, 2015).
"International Search Report—PCT/EP2015/056041":pp. 1-5 (dated May 6, 2015).
"International Search Report—PCT/EP2016/072277":pp. 1-5 (dated Dec. 8, 2016).
"International Search Report—PCT/EP2016/072349":pp. 1-5 (dated Nov. 29, 2016).
"International Search Report—PCT/EP2018/056140":pp. 1-9 (dated May 4, 2018).
"International Search Report—PCT/EP2018/056324" pp. 1-7 (dated May 8, 2018).
"International Search Report—PCT/EP2013/061890":pp. 1-9 (dated Sep. 17, 2013).
"International Search Report—PCT/EP2013/069679":pp. 1-3 (dated Nov. 8, 2013).
"International Search Report—PCT/EP2015/056032" :pp. 1-5 (dated Apr. 23, 2015).
"International Search Report—PCT/EP2016/057549":pp. 1-5 (dated Jun. 22, 2016).
"International Search Report—PCT/EP2016/072243":pp. 1-5 (dated Dec. 6, 2016).
"International Search Report—PCT/EP2016/072347":pp. 1-5 (dated Jan. 17, 2017).
"International Search Report—PCT/EP2016/070561":pp. 1-6 (dated Oct. 28, 2016).
Jones et al., "Novel autotaxin inhibitors for the treatment of osteoarthritis pain: Lead optimization via structure based drug design" ACS Med Chem Lett 7(9):857-861 (Sep. 8, 2016).
Kung et al., "Identification of spirocyclic piperidine-azetidine inverse agonists of the ghrelin receptor" Bioorg Med Chem Lett 22(13):4281-4287 (May 8, 2012).

(56) References Cited

OTHER PUBLICATIONS

Li, Jie Jack et al. Name Reactions for Homologation, Part 1 "Name Reactions for Homologation, Part 1" (Abstract of text, author information, and table of contents only, 2 pages),Wiley and Sons,:1-685 (May 1, 2009).

Litherland, et al., "The Amino-derivatives of Pentuerythritol. Part I. Preparation." J Chem Soc:1588-1595 (Jan. 1, 1938).

Matralis et al., "Development and therapeutic potential of autotaxin small molecule inhibitors: From bench to advanced clinical trials" Med. Res. Rev.:1-38 ( 2018).

Mayo Clinic Staff, (Lupus[online], retrieved from the internet on Jan. 24, 2017; http://www. mayoclinic.org/diseases-conditions/lupus basics/definition/CON-20019676) 2017.

Mitchell, Terence N., "Palladium-Catalysed Reactions of Organotin Compounds" Synthesis 9:803-815 (Aug. 16, 1991).

Negishi, et al. Metal-Catalyzed Cross-Coupling Reactions "Chapter 1: Palladium or NickelCatalyzed Cross Coupling with Organometals Containing Zinc, Magnesium, Aluminum, and Zirconium" (Preface, table of contents, list of contributors only, 22 pages), Diederich, Francois, Stang, Peter J., eds., Weinheim, DE:Wiley-VCH Verlag GmbH,:1-47 (Jan. 1, 2004).

Orr et al., "One-pot synthesis of chiral azetidines from chloroaldehyde and chiral amines" Tetrahedron Lett 52:36183620 (May 14, 2011).

Overberger et al., "Absolute Configuration of 2,7-Diazaspiro[4.4Inonane. A Reassignment" J. Org. Chem. 46(13):2757-2764 (Jun. 1, 1981).

Patani, G., et al., "Bioisosterism: A Rational Approach in Drug Design" Chem Rev 96(8):3147-3176 (Dec. 19, 1996).

Polshettiwar, V., et al., "Suzuki-Miyaura Cross-Coupling Reations in Aqueous Media: Green and Sustainable Syntheses of Biaryls" Chem Sus Chem 3:502-522 (Jan. 1, 2010).

Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2012).

Schlaeger, E. et al., "The protein hydrolysate, primatone RL, is a cost-effective multiple growth promoter of mammalian cel culture in serum-containing and serum-free medi and displays anti-apoptosis properties" J Immunol Methods 194:191-199 (Apr. 12, 1996).

Sheridan et al., "Cautious optimism surrounds early clinical data for PD-1 blocker" Nat. Biotechnol 30(8):729-730 (Aug. 1, 2012).

Sheridan et al., "The Most Common Chemical Replacements in Drug-Like Compounds" J. Chem. Inf. Comput. Sci. 42(1):103-108 ( 2002).

Sippy et al., "Preparation and characterization of N-(3-pyridinyl) spirocyclic diamines as ligands fo nicotinic acetylcholine receptors" Bioorg Med Chem Lett 19:1682-1685 (Feb. 4, 2009).

Stille, John K., "The Palladium-Catalyzed Cross-Coupling Reactions of Organotin Reagents with Organic Electrophiles" Angew Chem. Int. Ed. Engl. 25:508-524 (Jan. 1, 1986).

STN Columbus (STN International), pp. 1-13 ( Oct. 9, 2015).

Stocks et al., "A Practical Method for Targeted Library Design Balancing Lead-like Properties with Diversity" Chem Med Chem, 4:800-808 ( 2009).

Suzuki, A., et al., "Palladium-Catalyzed Cross-Coupling Reactions of Organoboron Compounds" Chem Rev. 95:2457-2483 (Jan. 31, 1995).

Suzuki, A., et al., "Recent advances in the cross-coupling reactions of organoboron derivatives with organic electrophiles, 1995-1998" J Organomet Chem 576:147-168 (Jan. 1, 1999).

Suzuki, A., et al., "Synthetic Studies via the cross-coupling reaction of organoboron derivatives with organic halides" Pure Appl Chem 63(3):419-422 (Jan. 1, 1991).

Thiel "Structure-aided drug design's next generation" Nat Biotechnol 22(5):513-519 (May 1, 2004).

Tucker, T., et al., "Discovery of 3-{5-[(6-Amino-1H-pyrazolo[3,4-b]pyridine-3-yl)methoxy]—2-chlorophenoxyl}-5-chlorobenzonitrile (MK-4965): A Potent, Orally Bioavailable HIV-1 Non-Nucleoside Reverse Transcriptase Inhibitor with Improved Potency against Key Mutan Viruses" J Med Chem 51:6503-6511 (Jul. 11, 2008).

Liu, Medicinal Chemistry (English translation):349 (Aug. 31, 2007).

Tan, Pharmacology (English translation),:27-28 (Jul. 31, 2006).

"U.S. Appl. No. 17/034,240, filed Sep. 28, 2020".

"U.S. Appl. No. 17/034,323, filed Sep. 28, 2020".

Written Opinion for PCT/EP2013/061890, 7 pages (dated Dec. 13, 2014).

Written Opinion for PCT/EP2013/069679, 6 pages (dated Mar. 25, 2013).

* cited by examiner

HETEROCYCLIC COMPOUNDS USEFUL AS DUAL ATX/CA INHIBITORS

This application is a continuation of International Application No. PCT/EP2018/056140, filed Mar. 13, 2018, which claims priority to EP Application No. 17161249.2 filed Mar. 16, 2017, each of which is incorporated herein by reference in its entirety.

The present invention relates to organic compounds useful for therapy or prophylaxis in a mammal, and in particular to dual autotaxin (ATX)/carbonic anhydrase inhibitors which are inhibitors of lysophosphatidic acid (LPA) production and thus modulators of LPA levels and associated signaling, for the treatment or prophylaxis of inflammatory conditions, conditions of the nervous system, vascular and cardiovascular conditions, cancer, and ocular conditions.

The present invention provides novel compounds of formula (I)

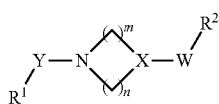

wherein
$R^1$ is selected from
  i) phenyl substituted by $R^3$, $R^4$ and $R^5$,
  ii) pyridinyl substituted by $R^3$, $R^4$ and $R^5$, and
  iii) thiophenyl substituted by $R^3$, $R^4$ and $R^5$;
X is selected from
  i) N, and
  ii) CH;
Y is selected from
  i) —$CH_2$—OC(O)—,
  ii) —$(CH_2)_q$C(O)—,
  iii) —(CH=CH)$_r$—C(O)—, and
  iv) —(CH≡CH)$_r$—C(O)—;
W is selected from
  i) —$(CR^9R^{10})_p$—,
  ii) —$(CR^9R^{10})_p$—C(O)—,
  iii) —$(CR^9R^{10})_p$—O—,
  iv) —$(CR^9R^{10})_p$—S—,
  v) —$(CR^9R^{10})_p$—S(O)—, and
  vi) —$(CR^9R^{10})_p$—S(O)$_2$—;
$R^2$ is selected from
  i) substituted phenyl, wherein the phenyl ring is substituted by $R^6$, $R^7$ and $R^8$,
  ii) substituted pyridinyl, wherein the pyridinyl ring is substituted by $R^6$, $R^7$ and $R^8$,
  iii) substituted thiophenyl, wherein the thiophenyl ring is substituted by $R^6$, $R^7$ and $R^8$, and
  iv) substituted thiazolyl, wherein the thiazolyl ring is substituted by $R^6$, $R^7$ and $R^8$;
$R^3$ is selected from
  i) halo-$C_{1-6}$-alkoxy,
  ii) $C_{3-8}$-cycloalkyl,
  iii) $C_{3-8}$-cycloalkyl-$C_{1-6}$-alkyl,
  iv) $C_{3-8}$-cycloalkyl-$C_{1-6}$-alkoxy,
  v) $C_{3-8}$-cycloalkoxy,
  vi) $C_{3-8}$-cycloalkoxy-$C_{1-6}$-alkyl,
  vii) tetrazolylmethyl,
  viii) triazolylmethyl,
  ix) pyrazolylmethyl,
  x) $C_{1-6}$-alkyltetrazolylmethyl,
  xi) $C_{1-6}$-alkyltriazolylmethyl,
  xii) $C_{1-6}$-alkylpyrazolylmethyl,
  xiii) heterocycloalkyl-$C_{1-6}$-alkoxy;
$R^4$ is selected from
  i) halogen,
  ii) hydroxy,
  iii) cyano,
  iv) $C_{1-6}$-alkyl,
  v) $C_{1-6}$-alkoxy,
  vi) $C_{1-6}$-alkoxy-$C_{1-6}$-alkyl,
  vii) halo-$C_{1-6}$-alkoxy,
  viii) halo-$C_{1-6}$-alkyl,
  ix) hydroxy-$C_{1-6}$-alkyl,
  x) $C_{3-8}$-cycloalkyl,
  xi) $C_{3-8}$-cycloalkyl-$C_{1-6}$-alkyl,
  xii) $C_{3-8}$-cycloalkyl-$C_{1-6}$-alkoxy,
  xiii) $C_{3-8}$-cycloalkoxy,
  xiv) $C_{3-8}$-cycloalkoxy-$C_{1-6}$-alkyl,
  xv) $C_{1-6}$-alkylcarbonylamino,
  xvi) $C_{3-8}$-cycloalkylcarbonylamino,
$R^5$ is selected from
  i) H,
  ii) halogen,
  iii) hydroxy,
  iv) cyano,
  v) $C_{1-6}$-alkyl,
  vi) $C_{1-6}$-alkoxy,
  vii) $C_{1-6}$-alkoxy-$C_{1-6}$-alkyl,
  viii) halo-$C_{1-6}$-alkoxy,
  ix) halo-$C_{1-6}$-alkyl,
  x) hydroxy-$C_{1-6}$-alkyl,
  xi) $C_{3-8}$-cycloalkyl,
  xii) $C_{3-8}$-cycloalkyl-$C_{1-6}$-alkyl,
  xiii) $C_{3-8}$-cycloalkyl-$C_{1-6}$-alkoxy,
  xiv) $C_{3-8}$-cycloalkoxy,
  xv) $C_{3-8}$-cycloalkoxy-$C_{1-6}$-alkyl,
  xvi) $C_{1-6}$-alkylcarbonylamino,
  xvii) $C_{3-8}$-cycloalkylcarbonylamino,
$R^6$ is aminosulfonyl;
$R^7$ and $R^8$ are independently selected from
  i) H,
  ii) halogen,
  iii) hydroxy,
  iv) cyano,
  v) $C_{1-6}$-alkyl,
  vi) $C_{1-6}$-alkoxy,
  vii) $C_{1-6}$-alkoxy-$C_{1-6}$-alkyl,
  viii) halo-$C_{1-6}$-alkoxy,
  ix) halo-$C_{1-6}$-alkyl,
  x) hydroxy-$C_{1-6}$-alkyl,
  xi) $C_{3-8}$-cycloalkyl,
  xii) $C_{3-8}$-cycloalkyl-$C_{1-6}$-alkyl,
  xiii) $C_{3-8}$-cycloalkyl-$C_{1-6}$-alkoxy,
  xiv) $C_{3-8}$-cycloalkoxy, and
  xv) $C_{3-8}$-cycloalkoxy-$C_{1-6}$-alkyl;
$R^9$ and $R^{10}$ are independently selected from
  i) H,
  ii) $C_{1-6}$-alkyl, and
  iii) $C_{3-8}$-cycloalkyl;
m and n are independently selected from zero, 1, 2, 3, 4 or 5, with the proviso that the sum of m and n is 2, 3, 4 or 5;
p is selected from zero, 1 or 2;
q is selected from zero or 2;
r is selected from zero and 1;
or pharmaceutically acceptable salts.

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

Carbonic anhydrases (CA) are a family of zinc-dependent enzymes, which catalyze the equilibration between carbon dioxide and water and hydrogencarbonate and a proton. The CA reaction is involved in many physiological and pathological processes. Carbonic anhydrase inhibition is useful for the treatment of ocular conditions, conditions of reduced blood flow, cancer, edema and inflammatory conditions including bacterial infections. Dual acting ATX/CA inhibitors are expected to lower intraocular pressure by facilitating two independent pathways, such as inhibition of aqueous humor (AH) production through CA inhibition at the ciliary body and facilitation of AH outflow by ATX inhibition within the AH drainage system. In conditions of vascular leakage in the eye such as diabetic retinopathy, age related macular disease, or retinal vein occlusion, CA levels have been shown or are expected to increase in the eye and facilitate an increase in pH. This is expected to activate many hydrolytic enzymes that can contribute to disease progression including ATX suggesting additional ATX inhibition by shifting the pH optimum.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and carbonic anhydrase activity therefore inhibit LPA production and modulate LPA levels and associated signaling. Dual ATX/CA-II inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and- chronic organ transplant rejection, and the use of the said compounds, salts or esters for the production of medicaments for the treatment or prophylaxis of inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particularly, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

The term "$C_1$-$C_6$-alkoxy" denotes a group of the formula —O—R', wherein R' is a $C_1$-$C_6$-alkyl group. Examples of $C_1$-$C_6$-alkoxy group include methoxy, ethoxy, n-propoxy, isopropoxy, n-butoxy, isobutoxy and tert-butoxy.

The term "$C_1$-$C_6$-alkoxy-$C_{1-6}$-alkyl" denotes a $C_1$-$C_6$-alkyl group wherein at least one of the hydrogen atoms of the $C_1$-$C_6$-alkyl group is replaced by a $C_1$-$C_6$-alkoxy group. Particular examples are methoxymethyl, methoxyethyl, ethoxymethyl, ethoxyethyl, iso-propoxymethyl and iso-propoxyethyl.

The term "$C_1$-$C_6$-alkyl" denotes a monovalent linear or branched saturated hydrocarbon group of 1 to 6 carbon atoms. Examples of $C_1$-$C_6$-alkyl include methyl, ethyl, propyl, isopropyl, n-butyl, iso-butyl, sec-butyl, tert-butyl and pentyl. Particular alkyl groups include methyl, isopropyl and tert-butyl.

The term "$C_1$-$C_6$-alkylcarbonyl" denotes a group of the formula —C(O)—R', wherein R' is a $C_1$-$C_6$-alkyl group. Examples of $C_1$-$C_6$-alkylcarbonyl group include groups wherein R' is methoxy, ethoxy, n-propoxy, isopropoxy, n-butoxy, isobutoxy and tert-butoxy.

The term "$C_1$-$C_6$-alkylcarbonylamino" denotes an amino group wherein the nitrogen atom is substituted by one H atom and by a $C_1$-$C_6$-alkylcarbonyl group. Particular example is an amino group wherein the nitrogen atom is substituted by H and tertbutylcarbonyl.

The term "$C_1$-$C_6$-alkylpyrazolyl" denotes a pyrazolyl group wherein one of the nitrogen atoms is substituted by a $C_1$-$C_6$-alkyl group. Particular example is a pyrazolyl group wherein one of the nitrogen atoms is substituted by methyl.

The term "$C_1$-$C_6$-alkylpyrazolyl-$C_1$-$C_6$-alkyl" denotes an $C_1$-$C_6$-alkyl group wherein one of the H atom is replaced by an $C_1$-$C_6$-alkylpyrazolyl group. Particular example is a methyl or a ethyl group wherein one of the hydrogen atoms is substituted by methylpyrazolyl.

The term "$C_1$-$C_6$-alkyltetrazolyl" denotes a tetrazolyl group wherein one of the nitrogen atoms is substituted by a $C_1$-$C_6$-alkyl group. Particular example is a tetrazolyl group wherein one of the nitrogen atoms is substituted by methyl.

The term "$C_1$-$C_6$-alkyltetrazolyl-$C_1$-$C_6$-alkyl" denotes an $C_1$-$C_6$-alkyl group wherein one of the H atom is replaced by an $C_1$-$C_6$-alkyltetrazolyl group. Particular example is a methyl or a ethyl group wherein one of the hydrogen atoms is substituted by methyltetrazolyl.

The term "$C_1$-$C_6$-alkyltriazolyl" denotes a triazolyl group wherein one of the nitrogen atoms is substituted by a $C_1$-$C_6$-alkyl group. Particular example is a triazolyl group wherein one of the nitrogen atoms is substituted by methyl.

The term "$C_1$-$C_6$-alkyltriazolyl-$C_1$-$C_6$-alkyl" denotes an $C_1$-$C_6$-alkyl group wherein one of the H atom is replaced by an $C_1$-$C_6$-alkyltriazolyl group. Particular example is a methyl or a ethyl group wherein one of the hydrogen atoms is substituted by methyltriazolyl.

The term "amino" denotes a —$NH_2$ group.

The term "cyano" denotes a —C≡N group.

The term "$C_3$-$C_8$-cycloalkoxy" denotes a group of the formula —O—R', wherein R' is a $C_3$-$C_8$-cycloalkyl. Particular example is a group wherein R' is cyclopropyl.

The term "$C_3$-$C_8$-cycloalkoxy-$C_1$-$C_6$-alkyl" denotes a $C_1$-$C_6$-alkyl group wherein at least one of the hydrogen atoms of the $C_1$-$C_6$-alkyl group is replaced by a $C_3$-$C_8$-cycloalkoxy group. Particular example is a methyl or ethyl group wherein the $C_3$-$C_8$-cycloalkoxy group is cyclopropoxy.

The term "$C_3$-$C_8$-cycloalkyl" denotes a monovalent saturated monocyclic or bicyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic $C_3$-$C_8$-cycloalkyl are bicyclo[2.2.1]heptanyl or bicyclo[2.2.2]octanyl. Particular $C_{3-8}$-cycloalkyl group is cyclopropyl.

The term "$C_3$-$C_8$-cycloalkyl-$C_1$-$C_6$-alkoxy" denotes a $C_1$-$C_6$-alkoxy group wherein at least one of the hydrogen atoms of the $C_1$-$C_6$-alkoxy group is replaced by a $C_3$-$C_8$-cycloalkyl group. Particular examples are methoxy or ethoxy groups wherein at least one of the hydrogen atoms of is replaced by a cyclopropyl.

The term "$C_3$-$C_8$-cycloalkyl-$C_1$-$C_6$-alkyl" denotes a $C_1$-$C_6$-alkyl group wherein at least one of the hydrogen atoms of the $C_1$-$C_6$-alkyl group is replaced by a $C_3$-$C_8$-cycloalkyl group. Particular examples are methyl or ethyl groups wherein at least one of the hydrogen atoms of is replaced by a cyclopropyl.

The term "$C_3$-$C_8$-cycloalkylcarbonyl" denotes a group of the formula —C(O)—R', wherein R' is a $C_3$-$C_8$-cycloalkyl group. Examples of $C_3$-$C_8$-cycloalkylcarbonyl are groups wherein R' is cyclopropyl.

The term "$C_3$-$C_8$-cycloalkylcarbonylamino" denotes an amino group wherein the nitrogen atom is substituted by one H atom and by a $C_3$-$C_8$-cycloalkylcarbonyl group. Particular example is an amino group wherein the nitrogen atom is substituted by a H and a cyclopropyl.

The term "halo-$C_1$-$C_6$-alkoxy" denotes a $C_1$-$C_6$-alkoxy group wherein at least one of the hydrogen atoms of the $C_1$-$C_6$-alkoxy group has been replaced by the same or different halogen atoms. Particular examples are difluoromethoxy, trifluoromethoxy, difluoroethoxy and trifluoroethoxy. More particular example is trifluoromethoxy.

The term "halogen" and "halo" are used interchangeably herein and denote fluoro, chloro, bromo or iodo. Particular halogen is chloro.

The term "halo-$C_1$-$C_6$-alkyl" denotes a $C_1$-$C_6$-alkyl group wherein at least one of the hydrogen atoms of the $C_1$-$C_6$-alkyl group has been replaced by the same or different halogen atoms. Particular examples are difluoromethyl, trifluoromethyl, difluoroethyl and trifluoroethyl. More particular example is trifluoromethyl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular example is tetrahydropyranyl.

The term "heterocycloalkyl-$C_1$-$C_6$-alkoxy" denotes a $C_1$-$C_6$-alkoxy group wherein at least one of the hydrogen atoms of the alkoxy group is replaced by a heterocycloalkyl group. Particular examples are tetrahydropyranylmethoxy.

The term "hydroxy" denotes a —OH group.

The term "hydroxy-$C_1$-$C_6$-alkoxy" denotes a $C_1$-$C_6$-alkoxy group wherein one of the hydrogen atoms of the $C_1$-$C_6$-alkoxy is replaced by a hydroxy group. Particular examples are hydroxyethoxy and hydroxypropoxy.

The term "hydroxy-$C_1$-$C_6$-alkyl" denotes a $C_1$-$C_6$-alkyl group wherein one of the hydrogen atoms of the $C_1$-$C_6$-alkyl group is replaced by a hydroxy group. Particular examples are hydroxymethyl and hydroxyethyl.

The term "phenyl-$C_1$-$C_6$-alkyl" denotes a $C_1$-$C_6$-alkyl group wherein one of the hydrogen atoms of the $C_1$-$C_6$-alkyl group is replaced by a phenyl group. Particular example is phenylmethyl.

The term "pyrazolyl-$C_1$-$C_6$-alkyl" denotes an $C_1$-$C_6$-alkyl group wherein one of the H atom is replaced by an pyrazolyl group. Particular example is a methyl or a ethyl group wherein one of the hydrogen atoms is substituted by pyrazolyl.

The term "tetrazolyl-$C_1$-$C_6$-alkyl" denotes an $C_1$-$C_6$-alkyl group wherein one of the H atom is replaced by an tetrazolyl group. Particular example is a methyl or a ethyl group wherein one of the hydrogen atoms is substituted by tetrazolyl.

The term "triazolyl-$C_1$-$C_6$-alkyl" denotes an $C_1$-$C_6$-alkyl group wherein one of the H atom is replaced by an triazolyl group. Particular example is a methyl or a ethyl group wherein one of the hydrogen atoms is substituted by triazolyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
$R^1$ is selected from
  i) phenyl substituted by $R^3$, $R^4$ and $R^5$, and
  ii) pyridinyl substituted by $R^3$, $R^4$ and $R^5$;
X is selected from
  iii) N, and
  iv) CH;
Y is selected from
  v) —$CH_2$—OC(O)—, and
  vi) —$(CH_2)_q$C(O)—;
W is selected from
  vii) —$(CR^9R^{10})_p$—,
  viii) —$(CR^9R^{10})_p$—C(O)—,
  ix) —$(CR^9R^{10})_p$—O—,
  x) —$(CR^9R^{10})_p$—S—,
  xi) —$(CR^9R^{10})_p$—S(O)—, and
  xii) —$(CR^9R^{10})_p$—S(O)$_2$—;
$R^2$ is selected from
  xiii) substituted phenyl, wherein the phenyl ring is substituted by $R^6$, $R^7$ and $R^8$,
  xiv) substituted pyridinyl, wherein the pyridinyl ring is substituted by $R^6$, $R^7$ and $R^8$,
  xv) substituted thiophenyl, wherein the thiophenyl ring is substituted by $R^6$, $R^7$ and $R^8$, and
  xvi) substituted thiazolyl, wherein the thiazolyl ring is substituted by $R^6$, $R^7$ and $R^8$;
$R^3$ is selected from
  xvii) halo-$C_{1-6}$-alkoxy,
  xviii) cyano,
  xix) $C_{3-8}$-cycloalkyl-$C_{1-6}$-alkoxy,
  xx) $C_{3-8}$-cycloalkoxy,
  xxi) $C_{1-6}$-alkyltetrazolylmethyl, and
  xxii) tetrahydropyranyl-$C_{1-6}$-alkoxy;
$R^4$ is selected from
  xxiii) halogen,
  xxiv) cyano,
  xxv) halo-$C_{1-6}$-alkoxy,
  xxvi) halo-$C_{1-6}$-alkyl,
  xxvii) $C_{3-8}$-cycloalkyl, and
  xxviii) $C_{1-6}$-alkylcarbonylamino;
$R^5$ is H;
$R^6$ is aminosulfonyl;
$R^7$ and $R^8$ are independently selected from
  xxix) H, and
  xxx) halogen;
$R^9$ and $R^{10}$ are both H;
m is selected from zero, 1 and 2 and n is selected from 1, 2 and 3, with the proviso that the sum of m and n is 2, 3, 4 or 5;
p is selected from zero, 1 and 2;
q is selected from zero and 2;
or pharmaceutically acceptable salts.

A particular embodiment of the present invention are compounds according to formula (I) as described herein, wherein $R^1$ is selected from
  xxxi) phenyl substituted by $R^3$, $R^4$ and $R^5$, and
  xxxii) pyridinyl substituted by $R^3$, $R^4$ and $R^5$.

A further particular embodiment of the present invention are compounds according to formula (I) as described herein, wherein $R^1$ is phenyl substituted by $R^3$, $R^4$ and $R^5$.

A particular embodiment of the present invention are compounds according to formula (I) as described herein, wherein Y is selected from
  xxxiii) —$CH_2$—OC(O)—, and
  xxxiv) —$(CH_2)_q$C(O)—.

A particular embodiment of the present invention are compounds according to formula (I) as described herein, wherein Y is —$(CH_2)_q$C(O)—.

A particular embodiment of the present invention are compounds according to formula (I) as described herein, wherein W is selected from
  xxxv) —$(CR^9R^{10})_p$—,
  xxxvi) —$(CR^9R^{10})_p$—S—, and
  xxxvii) —$(CR^9R^{10})_p$—S(O)$_2$—.

A further particular embodiment of the present invention are compounds according to formula (I) as described herein, wherein $R^2$ is selected from
  xxxviii) substituted phenyl, wherein the phenyl ring is substituted by $R^6$, $R^7$ and $R^8$, and
  xxxix) substituted pyridinyl, wherein the pyridinyl ring is substituted by $R^6$, $R^7$ and $R^8$.

A particular embodiment of the present invention are compounds according to formula (I) as described herein, wherein $R^3$ is selected from
  xl) halo-$C_{1-6}$-alkoxy,
  xli) cyano,
  xlii) $C_{3-8}$-cycloalkyl-$C_{1-6}$-alkoxy,
  xliii) $C_{3-8}$-cycloalkoxy,
  xliv) $C_{1-6}$-alkyltetrazolylmethyl, and
  xlv) tetrahydropyranyl-$C_{1-6}$-alkoxy.

A further particular embodiment of the present invention are compounds according to formula (I) as described herein, wherein $R^3$ is selected from
  xlvi) $C_{1-6}$-alkyltetrazolylmethyl, and
  xlvii) tetrahydropyranyl-$C_{1-6}$-alkoxy.

A particular embodiment of the present invention are compounds according to formula (I) as described herein, wherein $R^4$ is selected from
  xlviii) halogen,
  xlix) cyano,
  l) halo-$C_{1-6}$-alkoxy,
  li) halo-$C_{1-6}$-alkyl,
  lii) $C_{3-8}$-cycloalkyl, and
  liii) $C_{1-6}$-alkylcarbonylamino.

A particular embodiment of the present invention are compounds according to formula (I) as described herein, wherein $R^4$ is selected from
  liv) halo-$C_{1-6}$-alkyl, and
  lv) $C_{3-8}$-cycloalkyl.

A further particular embodiment of the present invention are compounds according to formula (I) as described herein, wherein $R^5$ is H.

A further particular embodiment of the present invention are compounds according to formula (I) as described herein, wherein $R^7$ and $R^8$ are independently selected from
  lvi) H, and
  lvii) halogen.

A particular embodiment of the present invention are compounds according to formula (I) as described herein, wherein R' is halogen.

A particular embodiment of the present invention are compounds according to formula (I) as described herein, wherein $R^8$ is selected from
  lviii) H, and
  lix) halogen.

A more particular embodiment of the present invention are compounds according to formula (I) as described herein, wherein $R^9$ and $R^{10}$ are both H.

A particular embodiment of the present invention are compounds according to formula I(a) as described herein, wherein m is selected from zero, 1 and 2 and n is selected from 1, 2 and 3, with the proviso that the sum of m and n is 2, 3, 4 or 5.

A particular embodiment of the present invention are compounds according to formula I(a) as described herein, wherein p is selected from zero and 1.

A particular embodiment of the present invention are compounds according to formula I(a) as described herein, wherein p is zero.

A particular embodiment of the present invention are compounds according to formula I(a) as described herein, wherein q is 2.

A particular embodiment of the present invention are compounds according to formula I(a) as described herein, wherein
  $R^1$ is selected from
    i) phenyl substituted by $R^3$, $R^4$ and $R^5$, and
    ii) pyridinyl substituted by $R^3$, $R^4$ and $R^5$;
  X is selected from
    iii) N, and
    iv) CH;
  Y is selected from
    v) —$CH_2$—OC(O)—, and
    vi) —$(CH_2)_q$C(O)—;
  W is selected from
    vii) —$(CR^9R^{10})_p$—,
    viii) —$(CR^9R^{10})_p$—C(O)—,
    ix) —$(CR^9R^{10})_p$—O—,
    x) —$(CR^9R^{10})_p$—S—,
    xi) —$(CR^9R^{10})_p$—S(O)—, and
    xii) —$(CR^9R^{10})_p$—S(O)$_2$—;
  $R^2$ is selected from
    xiii) substituted phenyl, wherein the phenyl ring is substituted by $R^6$, $R^7$ and $R^8$,
    xiv) substituted pyridinyl, wherein the pyridinyl ring is substituted by $R^6$, $R^7$ and $R^8$,
    xv) substituted thiophenyl, wherein the thiophenyl ring is substituted by $R^6$, $R^7$ and $R^8$, and
    xvi) substituted thiazolyl, wherein the thiazolyl ring is substituted by $R^6$, $R^7$ and $R^8$;
  $R^3$ is selected from
    xvii) halo-$C_{1-6}$-alkoxy,
    xviii) cyano,
    xix) $C_{3-8}$-cycloalkyl-$C_{1-6}$-alkoxy,
    xx) $C_{3-8}$-cycloalkoxy,
    xxi) $C_{1-6}$-alkyltetrazolylmethyl, and
    xxii) tetrahydropyranyl-$C_{1-6}$-alkoxy;
  $R^4$ is selected from
    xxiii) halogen,
    xxiv) cyano,
    xxv) halo-$C_{1-6}$-alkoxy,
    xxvi) halo-$C_{1-6}$-alkyl,
    xxvii) $C_{3-8}$-cycloalkyl, and
    xxviii) $C_{1-6}$-alkylcarbonylamino;

R⁵ is H;
R⁶ is aminosulfonyl;
R⁷ and R⁸ are independently selected from
  xxix) H, and
  xxx) halogen;
R⁹ and R¹⁰ are both H;
m is selected from zero, 1 and 2 and n is selected from 1, 2 and 3, with the proviso that the sum of m and n is 2, 3, 4 or 5;
p is selected from zero, 1 and 2;
q is selected from zero and 2;
or pharmaceutically acceptable salts.

Particular examples of compounds of formula (I) as described herein are selected from 2-((5-methyl-2H-tetrazol-2-yl)methyl)-4-(trifluoromethyl) benzyl 4-(2-fluoro-4-sulfamoylphenyl)piperazine-1-carboxylate;

[2-cyclopropyl-6-(oxan-4-ylmethoxy)pyridin-4-yl]methyl 4-[(4-sulfamoylphenyl)methyl]piperidine-1-carboxylate;

[5-cyano-3-(2,2-dimethylpropanoylamino)pyridin-2-yl] methyl 4-[(4-sulfamoylphenyl)methyl]piperidine-1-carboxylate;

[5-chloro-3-[(5-methyltetrazol-2-yl)methyl]pyridin-2-yl] methyl 4-(2-fluoro-4-sulfamoylphenyl)sulfonylpiperidine-1-carboxylate;

[2-[(5-methyltetrazol-2-yl)methyl]-4-(trifluoromethyl)phenyl]methyl 4-(2-fluoro-4-sulfamoylphenyl)sulfonylpiperidine-1-carboxylate;

2-fluoro-4-[[4-[3-[2-[(5-methyltetrazol-2-yl)methyl]-4-(trifluoromethyl)phenyl]propanoyl]piperazin-1-yl]methyl]benzenesulfonamide;

3-fluoro-4-[[4-[3-[2-[(5-methyltetrazol-2-yl)methyl]-4-(trifluoromethyl)phenyl]propanoyl]piperazin-1-yl]methyl]benzenesulfonamide;

4-[[4-[2-cyclopropyl-6-(oxan-4-ylmethoxy)pyridine-4-carbonyl]piperazin-1-yl]methyl]-3-fluorobenzenesulfonamide;

3-fluoro-4-[4-[3-[2-[(5-methyltetrazol-2-yl)methyl]-4-(trifluoromethyl)phenyl]propanoyl]piperazine-1-carbonyl]benzenesulfonamide;

2-fluoro-4-[4-[3-[2-[(5-methyltetrazol-2-yl)methyl]-4-(trifluoromethyl)phenyl]propanoyl]piperazine-1-carbonyl]benzenesulfonamide;

3,5-difluoro-4-[4-[3-[2-[(5-methyltetrazol-2-yl)methyl]-4-(trifluoromethyl)phenyl]propanoyl]piperazine-1-carbonyl]benzenesulfonamide;

3-fluoro-4-[4-[3-[2-[(5-methyltetrazol-2-yl)methyl]-4-(trifluoromethyl)phenyl]propanoyl]piperazine-1-carbonyl]benzenesulfonamide;

4-(4-(3-(2-((5-methyl-2H-tetrazol-2-yl)methyl)-4-(trifluoromethyl)phenyl)propanoyl)piperazine-1-carbonyl)benzenesulfonamide;

3-[[1-[2-cyclopropyl-6-(oxan-4-ylmethoxy)pyridine-4-carbonyl]piperidin-4-yl]methyl]-4-fluorobenzenesulfonamide;

3-fluoro-4-[1-[3-[2-[(5-methyltetrazol-2-yl)methyl]-4-(trifluoromethyl)phenyl]propanoyl]piperidin-4-yl]sulfanylbenzenesulfonamide;

3-fluoro-4-(4-(3-(2-((5-methyl-2H-tetrazol-2-yl)methyl)-4-(trifluoromethyl)phenyl)propanoyl)piperazin-1-yl)benzenesulfonamide;

4-[[1-[2-cyclopropyl-6-(oxan-4-ylmethoxy)pyridine-4-carbonyl]piperidin-4-yl]methyl]benzenesulfonamide;

4-[[1-[3-[2-[(5-methyltetrazol-2-yl)methyl]-4-(trifluoromethyl)phenyl]propanoyl]piperidin-4-yl]methyl]benzenesulfonamide;

4-[[1-[3-[2-[(5-methyltetrazol-2-yl)methyl]-4-(trifluoromethyl)phenyl]propanoyl]pyrrolidin-2-yl]methoxy]benzenesulfonamide;

4-[[1-[3-[2-[(5-methyltetrazol-2-yl)methyl]-4-(trifluoromethyl)phenyl]propanoyl]pyrrolidin-3-yl]methoxy]benzenesulfonamide;

4-(1-(3-(2-((5-methyl-2H-tetrazol-2-yl)methyl)-4-(trifluoromethyl)phenyl)propanoyl)piperidin-4-yl)benzenesulfonamide;

4-(4-(3-(2-((5-methyl-2H-tetrazol-2-yl)methyl)-4-(trifluoromethyl)phenyl)propanoyl)piperazin-1-yl)benzenesulfonamide;

4-fluoro-3-[[1-[3-[2-[(5-methyltetrazol-2-yl)methyl]-4-(trifluoromethyl)phenyl]propanoyl]piperidin-4-yl]methyl]benzenesulfonamide;

2,3-difluoro-4-[1-[3-[2-[(5-methyltetrazol-2-yl)methyl]-4-(trifluoromethyl)phenyl]propanoyl]piperidin-4-yl]sulfanylbenzenesulfonamide;

2,3-difluoro-4-[1-[3-[2-[(5-methyltetrazol-2-yl)methyl]-4-(trifluoromethyl)phenyl]propanoyl]piperidin-4-yl]sulfinylbenzenesulfonamide;

2,3-difluoro-4-[1-[3-[2-[(5-methyltetrazol-2-yl)methyl]-4-(trifluoromethyl)phenyl]propanoyl]piperidin-4-yl]sulfonylbenzenesulfonamide;

2,3-difluoro-4-[2-[1-[3-[2-[(5-methyltetrazol-2-yl)methyl]-4-(trifluoromethyl)phenyl]propanoyl]piperidin-4-yl]ethylsulfonyl]benzenesulfonamide;

2-[1-[3-[2-[(5-methyltetrazol-2-yl)methyl]-4-(trifluoromethyl)phenyl]propanoyl]piperidin-4-yl]sulfanyl-1,3-thiazole-5-sulfonamide;

2-[1-[3-[2-[(5-methyltetrazol-2-yl)methyl]-4-(trifluoromethyl)phenyl]propanoyl]piperidin-4-yl]sulfonyl-1,3-thiazole-5-sulfonamide;

2-[2-[1-[3-[2-[(5-methyltetrazol-2-yl)methyl]-4-(trifluoromethyl)phenyl]propanoyl]piperidin-4-yl]ethylsulfinyl]-1,3-thiazole-5-sulfonamide;

3-fluoro-4-[[1-[3-[2-[(5-methyltetrazol-2-yl)methyl]-4-(trifluoromethyl)phenyl]propanoyl]piperidin-4-yl]methylsulfanyl]benzenesulfonamide;

3-fluoro-4-[[1-[3-[2-[(5-methyltetrazol-2-yl)methyl]-4-(trifluoromethyl)phenyl]propanoyl]piperidin-4-yl]methylsulfinyl]benzenesulfonamide;

3-fluoro-4-[[1-[3-[2-[(5-methyltetrazol-2-yl)methyl]-4-(trifluoromethyl)phenyl]propanoyl]piperidin-4-yl]methylsulfonyl]benzenesulfonamide;

3-fluoro-4-[1-[3-[2-[(5-methyltetrazol-2-yl)methyl]-4-(trifluoromethyl)phenyl]propanoyl]azetidin-3-yl]sulfanylbenzenesulfonamide;

3-fluoro-4-[1-[3-[2-[(5-methyltetrazol-2-yl)methyl]-4-(trifluoromethyl)phenyl]propanoyl]azetidin-3-yl]sulfinylbenzenesulfonamide;

3-fluoro-4-[1-[3-[2-[(5-methyltetrazol-2-yl)methyl]-4-(trifluoromethyl)phenyl]propanoyl]azetidin-3-yl]sulfonylbenzenesulfonamide;

3-fluoro-4-[1-[3-[2-[(5-methyltetrazol-2-yl)methyl]-4-(trifluoromethyl)phenyl]propanoyl]piperidin-4-yl]sulfinylbenzenesulfonamide;

3-fluoro-4-[1-[3-[2-[(5-methyltetrazol-2-yl)methyl]-4-(trifluoromethyl)phenyl]propanoyl]piperidin-4-yl]sulfonylbenzenesulfonamide;

3-fluoro-4-[2-[1-[3-[2-[(5-methyltetrazol-2-yl)methyl]-4-(trifluoromethyl)phenyl]propanoyl]piperidin-4-yl]ethylsulfanyl]benzenesulfonamide;

3-fluoro-4-[2-[1-[3-[2-[(5-methyltetrazol-2-yl)methyl]-4-(trifluoromethyl)phenyl]propanoyl]piperidin-4-yl]ethylsulfinyl]benzenesulfonamide;

3-fluoro-4-[2-[1-[3-[2-[(5-methyltetrazol-2-yl)methyl]-4-(trifluoromethyl)phenyl]propanoyl]piperidin-4-yl]ethylsulfonyl]benzenesulfonamide;
3-fluoro-4-[2-[1-[6-(2,2,2-trifluoroethoxy)-5-(trifluoromethyl)pyridine-3-carbonyl]piperidin-4-yl]ethylsulfonyl]benzenesulfonamide;
3-fluoro-4-[4-[3-[2-[(5-methyltetrazol-2-yl)methyl]-4-(trifluoromethyl)phenyl]propanoyl]piperazin-1-yl]sulfonyl-benzenesulfonamide;
4-[[1-[2-cyclopropyl-6-(oxan-4-ylmethoxy)pyridine-4-carbonyl]piperidin-4-yl]methylsulfanyl]-3-fluorobenzenesulfonamide;
4-[[1-[2-cyclopropyl-6-(oxan-4-ylmethoxy)pyridine-4-carbonyl]piperidin-4-yl]methylsulfinyl]-3-fluorobenzenesulfonamide;
4-[[1-[2-cyclopropyl-6-(oxan-4-ylmethoxy)pyridine-4-carbonyl]piperidin-4-yl]methylsulfonyl]-3-fluorobenzenesulfonamide;
4-[1-(6-cyclobutyloxy-5-cyclopropylpyridine-3-carbonyl)piperidin-4-yl]sulfonyl-3-fluorobenzenesulfonamide;
4-[1-[2-cyclopropyl-6-(oxan-4-ylmethoxy)pyridine-4-carbonyl]azetidin-3-yl]sulfanyl-3-fluorobenzenesulfonamide;
4-[1-[2-cyclopropyl-6-(oxan-4-ylmethoxy)pyridine-4-carbonyl]azetidin-3-yl]sulfinyl-3-fluorobenzenesulfonamide;
4-[1-[2-cyclopropyl-6-(oxan-4-ylmethoxy)pyridine-4-carbonyl]azetidin-3-yl]sulfonyl-3-fluorobenzenesulfonamide;
4-[1-[2-cyclopropyl-6-(oxan-4-ylmethoxy)pyridine-4-carbonyl]piperidin-4-yl]sulfonyl-2,3-difluorobenzenesulfonamide;
4-[1-[2-cyclopropyl-6-(oxan-4-ylmethoxy)pyridine-4-carbonyl]piperidin-4-yl]sulfonyl-3-fluorobenzenesulfonamide;
4-[1-[3-[4-chloro-2-[(5-methyltetrazol-2-yl)methyl]phenyl]propanoyl]piperidin-4-yl]sulfonyl-3-fluorobenzenesulfonamide;
4-[1-[3-[4-cyano-2-[(5-methyltetrazol-2-yl)methyl]phenyl]propanoyl]piperidin-4-yl]sulfonyl-3-fluorobenzenesulfonamide;
4-[2-[1-[2-cyclopropyl-6-(oxan-4-ylmethoxy)pyridine-4-carbonyl]piperidin-4-yl]ethylsulfanyl]-3-fluorobenzenesulfonamide;
4-[2-[1-[2-cyclopropyl-6-(oxan-4-ylmethoxy)pyridine-4-carbonyl]piperidin-4-yl]ethylsulfinyl]-3-fluorobenzenesulfonamide;
4-[2-[1-[2-cyclopropyl-6-(oxan-4-ylmethoxy)pyridine-4-carbonyl]piperidin-4-yl]ethylsulfonyl]-3-fluorobenzenesulfonamide;
4-[2-[1-[5-cyclopropyl-6-(cyclopropylmethoxy)pyridine-3-carbonyl]piperidin-4-yl]ethylsulfonyl]-3-fluorobenzenesulfonamide;
4-[4-[2-cyclopropyl-6-(oxan-4-ylmethoxy)pyridine-4-carbonyl]piperazin-1-yl]sulfonyl-3-fluorobenzenesulfonamide;
4-[4-[3-[2-[(5-methyltetrazol-2-yl)methyl]-4-(trifluoromethyl)phenyl]propanoyl]piperazin-1-yl]sulfonylbenzenesulfonamide;
5-[1-[3-[2-[(5-methyltetrazol-2-yl)methyl]-4-(trifluoromethyl)phenyl]propanoyl]piperidin-4-yl]sulfanylthiophene-2-sulfonamide;
5-[2-[1-[3-[2-[(5-methyltetrazol-2-yl)methyl]-4-(trifluoromethyl)phenyl]propanoyl]piperidin-4-yl]ethylsulfonyl]thiophene-2-sulfonamide;
5-fluoro-6-[1-[3-[2-[(5-methyltetrazol-2-yl)methyl]-4-(trifluoromethyl)phenyl]propanoyl]piperidin-4-yl]sulfanylpyridine-3-sulfonamide;
6-[1-[2-cyclopropyl-6-(oxan-4-ylmethoxy)pyridine-4-carbonyl]piperidin-4-yl]sulfanyl-5-fluoropyridine-3-sulfonamide;
4-[1-[3-[4-(difluoromethoxy)-2-[(5-methyltetrazol-2-yl)methyl]phenyl]propanoyl]piperidin-4-yl]sulfonyl-3-fluorobenzenesulfonamide;
4-[2-[1-[3-[4-(difluoromethoxy)-2-[(5-methyltetrazol-2-yl)methyl]phenyl]propanoyl]piperidin-4-yl]ethylsulfinyl]-2,3-difluorobenzenesulfonamide;
2,3-difluoro-4-[2-[1-[3-[2-[(5-methyltetrazol-2-yl)methyl]-4-(trifluoromethyl)phenyl]propanoyl]piperidin-4-yl]ethylsulfinyl]benzenesulfonamide;
2-[2-[1-[3-[4-(difluoromethoxy)-2-[(5-methyltetrazol-2-yl)methyl]phenyl]propanoyl]piperidin-4-yl]ethylsulfinyl]-1,3-thiazole-5-sulfonamide;
2-[2-[1-[3-[2-[(5-methyltetrazol-2-yl)methyl]-4-(trifluoromethyl)phenyl]propanoyl]piperidin-4-yl]ethylsulfonyl]-1,3-thiazole-5-sulfonamide;
(+)-3-fluoro-4-[[1-[3-[2-[(5-methyltetrazol-2-yl)methyl]-4-(trifluoromethyl)phenyl]propanoyl]piperidin-4-yl]sulfinyl]benzenesulfonamide;
(+)-4-[[1-[3-[2-[(5-methyltetrazol-2-yl)methyl]-4-(trifluoromethyl)phenyl]propanoyl]pyrrolidin-2-yl]methoxy]benzenesulfonamide;
(+)-4-[[1-[3-[2-[(5-methyltetrazol-2-yl)methyl]-4-(trifluoromethyl)phenyl]propanoyl]pyrrolidin-3-yl]methoxy]benzenesulfonamide;
(−)-3-fluoro-4-[[1-[3-[2-[(5-methyltetrazol-2-yl)methyl]-4-(trifluoromethyl)phenyl]propanoyl]piperidin-4-yl]sulfinyl]benzenesulfonamide;
(−)-4-[[1-[3-[2-[(5-methyltetrazol-2-yl)methyl]-4-(trifluoromethyl)phenyl]propanoyl]pyrrolidin-2-yl]methoxy]benzenesulfonamide;
(−)-4-[[1-[3-[2-[(5-methyltetrazol-2-yl)methyl]-4-(trifluoromethyl)phenyl]propanoyl]pyrrolidin-3-yl]methoxy]benzenesulfonamide;
4-((4-(3-(2-((5-methyl-2H-tetrazol-2-yl)methyl)-4-(trifluoromethyl)phenyl)propanoyl)piperazin-1-yl)methyl)benzenesulfonamide;
and pharmaceutically acceptable salts thereof.

Further particular examples of compounds of formula (I) as described herein are selected from
3-fluoro-4-[[4-[3-[2-[(5-methyltetrazol-2-yl)methyl]-4-(trifluoromethyl)phenyl]propanoyl]piperazin-1-yl]methyl]benzenesulfonamide;
2,3-difluoro-4-[1-[3-[2-[(5-methyltetrazol-2-yl)methyl]-4-(trifluoromethyl)phenyl]propanoyl]piperidin-4-yl]sulfonylbenzenesulfonamide;
3-fluoro-4-[1-[3-[2-[(5-methyltetrazol-2-yl)methyl]-4-(trifluoromethyl)phenyl]propanoyl]piperidin-4-yl]sulfonyl-benzenesulfonamide;
3-fluoro-4-[4-[3-[2-[(5-methyltetrazol-2-yl)methyl]-4-(trifluoromethyl)phenyl]propanoyl]piperazin-1-yl]sulfonyl-benzenesulfonamide;
4-[1-[2-cyclopropyl-6-(oxan-4-ylmethoxy)pyridine-4-carbonyl]piperidin-4-yl]sulfonyl-2,3-difluorobenzenesulfonamide;
4-[1-[2-cyclopropyl-6-(oxan-4-ylmethoxy)pyridine-4-carbonyl]piperidin-4-yl]sulfonyl-3-fluorobenzenesulfonamide;
5-fluoro-6-[1-[3-[2-[(5-methyltetrazol-2-yl)methyl]-4-(trifluoromethyl)phenyl]propanoyl]piperidin-4-yl]sulfanylpyridine-3-sulfonamide;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

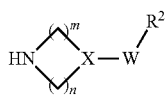

1

For instance, amine 1 is reacted with a suitable carboxylic acid of formula $R^1$—Y—OH (2) leading to a compound of formula (I), wherein Y is —$(CH_2)_q$C(O)—, —(CH=CH)$_r$—C(O)—, or —(CH≡CH)$_r$—C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$—Y—Cl (3) to lead to compounds of formula (I), wherein Y is —$(CH_2)_q$C(O)—, —(CH=CH)$_r$—C(O)—, or —(CH≡CH)$_r$—C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 1 is reacted with a suitable chloroformate ester of formula $R^1$—$CH_2$—O—C(O)—Cl (4), or with an imidazole-1-carboxylate ester of formula (5), leading to a compound of formula (I) wherein Y is —$CH_2$—OC(O)—.

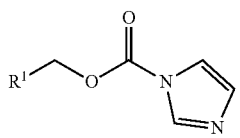

5

The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Chloroformate esters 4 are commercially available or can be synthesised from the corresponding alcohol of formula $R^1$—$CH_2$—OH (6), by reaction with phosgene or a phosgene equivalent (e. g., diphosgene, triphosgene), as described in the literature.

Imidazole-1-carboxylate esters 5 are synthesised from the corresponding alcohols of formula $R^1$—$CH_2$—OH (6), by reaction with 1,1'-carbonyldiimidazole. The reaction is performed at room temperature, in a solvent such as dichloromethane, tetrahydrofuran or acetonitrile. The imidazole-1-carboxylate esters 5 are typically not isolated but directly reacted with amines 1 as described above.

Alcohols of formula $R^1$—$CH_2$—OH (6), are commercially available or can be produced by methods described herein or known in the art.

Carboxylic acids (2) and acyl halides (3) are commercially available or can be prepared as described herein or in the literature.

Amines of general formula 1 are synthesised from suitably protected precursors 7.

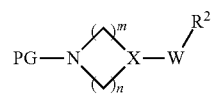

7

Suitable protective groups (PG) are tert-butoxycarbonyl, benzyloxycarbonyl, or acetyl. The deprotection of intermediates 7 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Alternatively, in the case where PG is acetyl, the deprotection may be performed in the presence of a suitable acid, e. g, aqueous hydrochloric acid in at temperatures between 0° C. and 100° C.

Intermediates 7 wherein X is N, W is —$(CR^9R^{10})_p$—C(O)— and p is zero can be represented by general structure 7A. PG is a suitable protective group, e. g., tert-butoxycarbonyl, benzyloxycarbonyl, or acetyl, $R^2$, m and n are as defined above.

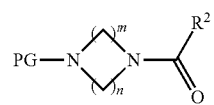

7A

Amides 7A can be produced from amine precursors of general formula 8 by reaction with appropriate reagents, using methods known in the art.

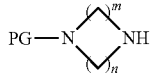

8

For instance, amine 8 is reacted with a suitable carboxylic acid of formula $R^2$—COOH (9), leading to compounds of formula 8A. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Intermediates 7 wherein X is N, W is —$(CR^9R^{10})_p$—S$(O)_2$— and p is zero can be represented by general structure 7B. PG is a suitable protective group, e. g., tert-butoxycarbonyl, benzyloxycarbonyl, or acetyl, $R^2$, m and n are as defined above.

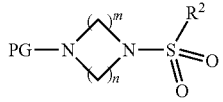

7B

Sulfonamides 7B can be produced from amine precursors of general formula 8 by reaction with appropriate reagents, using methods known in the art. For instance, amine 8 is reacted with a suitable sulfonyl chloride of formula $R^2$—$SO_2Cl$ (10), leading to compounds of formula 7B. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Amines 8, carboxylic acids 9, and sulfonyl chlorides 10 are commercially available or can be synthesised as described herein or in the literature.

Intermediates 7 wherein W is —$(CR^9R^{10})_p$— can be represented by general structure 7C. Intermediates 7C are commercially available or can be produced as described herein or using methods known in the art. PG is a suitable protective group, e. g., tert-butoxycarbonyl, benzyloxycarbonyl, or acetyl, $R^2$, $R^9$, $R^{10}$, m, n and p are as defined above.

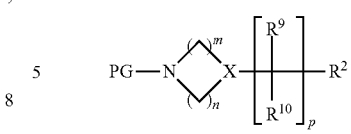

7C

Intermediates 7C wherein $R^2$ is substituted phenyl can be represented by general structure 7CA. and can be represented by general structure 7CA. PG is a suitable protective group, e. g., tert-butoxycarbonyl, benzyloxycarbonyl, or acetyl, $R^2$, $R^7$, $R^8$, $R^9$, $R^{10}$, m, n and p are as defined above.

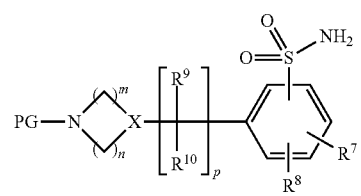

7CA

Intermediates 7CA can be produced from compounds 11 using methods known in the art.

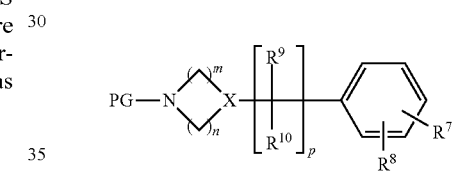

11

For instance, compound chlorosulfonation of 11 leads to sulfonyl chloride 12. The reaction can be performed with an appropriate reagent, e. g., chlorosulfonic acid, without solvent or in a suitable solvent, e. g., dichloromethane, at temperatures between 0° C. and 100° C.

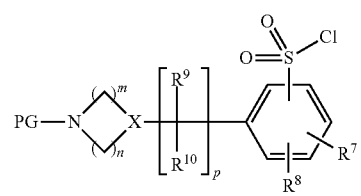

12

In a second step, reaction of sulfonyl chloride 12 with ammonia leads to 7CA. This reaction can be performed in a suitable solvent, e. g., water, ethanol, tetrahydrofuran, or mixtures thereof, at temperatures between 0° C. and the 50° C.

Compounds 11 are commercially available or can be synthesised as described herein or in the literature.

Intermediates 7 wherein X is CH and W is —$(CR^9R^{10})$—S— or —$(CR^9R^{10})_p$—O— can be represented by general structure 7D. V is oxygen or sulfur, $R^2$, $R^9$, $R^{10}$, m, n and p are as described above, PG is a protective group, e. g., benzyloxycarbonyl, tert-butoxycarbonyl, or acetyl.

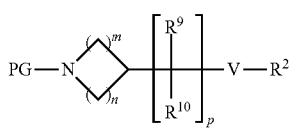

7D

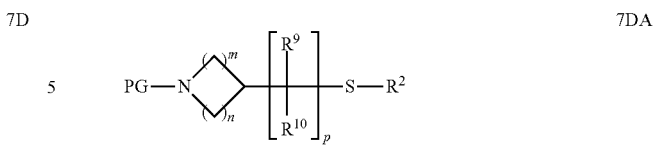

7DA

Compounds of formula 7D can be synthesised from alcohol or thiol 13 using methods and reagents known in the art.

Intermediates 7 wherein X is CH and W is —(CR$^9$R$^{10}$)$_p$—S(O)— can be represented by general structure 7E. R$^2$, R$^9$, R$^{10}$, m, n and p are as described above, PG is a protective group, e. g., benzyloxycarbonyl, tert-butoxycarbonyl, or acetyl.

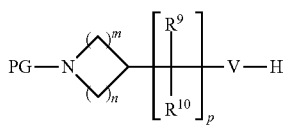

13

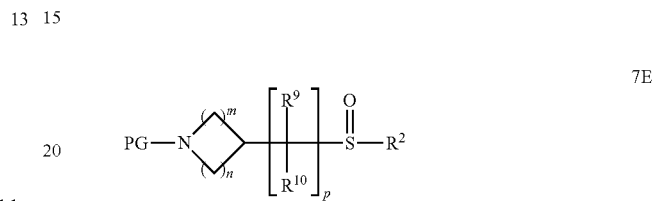

7E

For instance, alcohol or thiol 13 is reacted with a suitable halide, R$^2$-Hal (14). Hal is F (preferred), Cl, Br, or I. The reaction is performed in the presence of a base, e. g., sodium hydride, cesium carbonate, or potassium carbonate, in a suitable solvent, e. g., tetrahydrofuran or N,N-dimethylacetamide, at temperatures between −78° C. and +100° C. It may be necessary to protect the aminosulfonyl group in halide 14. A suitable sulfonamide protective group is the sulfonylformamidine group, which can be obtained by reaction of the primary sulfonamide with dimethylamide dimethyl acetal, as described herein or in the literature.

Alternatively, compounds of formula 7D can be synthesised from alcohol 13A and phenol R$^2$—OH (15) or thiophenol R$^2$—SH (16), using reagents and methods known in the art.

Sulfoxides 7E can be produced from sulfides 7DA using methods and reagents known in the art. For instance, the reaction can be performed in the presence of a peroxide reagent, e. g., hydrogen peroxide or 3-chloroperbenzoic acid, in a solvent, e. g., dichloromethane, acetic acid or formic acid, at temperatures between 0° C. and +50° C.—

Intermediates 7 wherein X is CH and W is —(CR$^9$R$^{10}$)$_p$—S(O)$_2$— can be represented by general structure 7F. R$^2$, R$^9$, R$^{10}$, m, n and p are as described above, PG is a protective group, e. g., benzyloxycarbonyl, tert-butoxycarbonyl, or acetyl.

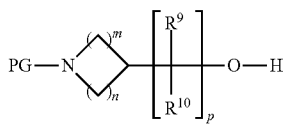

13A

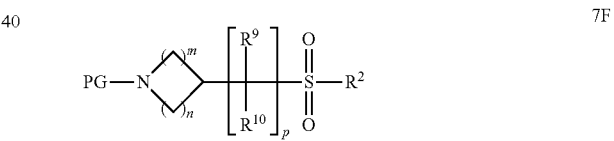

7F

This reaction can be performed using a phosphine, e. g., triphenylphosphine, an azodicarboxylate, e.g., diethyl azodicarboxylate or diisopropyl azodicarboxylate, in a solvent such as dichloromethane, toluene or tetrahydrofuran and at temperatures between 0° C. and 40° C. It may be necessary to protect the aminosulfonyl group in phenol 15 or thiophenol 16. A suitable sulfonamide protective group is the sulfonylformamidine group, which can be obtained by reaction of the primary sulfonamide with N,N-dimethylamide dimethyl acetal, as described herein or in the literature.

Alcohols and thiols 13 are commercially available can be produced as described herein or using methods known in the art.

Intermediates 7D wherein V is sulfur can be represented by general structure 7DA. R$^2$, R$^9$, R$^{10}$, m and n are as described above, PG is a protective group, e. g., benzyloxycarbonyl, tert-butoxycarbonyl, or acetyl.

Sulfones 7F can be produced from intermediates sulfides 7DA or sulfoxides 7D using a suitable peroxide reagent, e. g., hydrogen peroxide or 3-chloroperbenzoic acid in a solvent, e. g., dichloromethane, acetic acid or formic acid, at temperatures between 0° C. and +50° C.

Compounds of formula (I) wherein X is N, W is —(CR$^9$R$^{10}$)$_p$—C(O)— or —(CR$^9$R$^{10}$)$_p$—S(O)$_2$— and p is zero can be represented by general structure 17. Z is C(O) or S(O)$_2$, R$^1$, R$^2$, m and n are as described above.

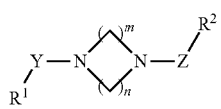

17

Compounds of formula 17 wherein Z is C(O) can be represented by general structure 17A. R$^1$, R$^2$, m and n are as described above.

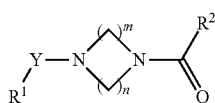

17A

Amides 17A can be produced from amine precursors of general formula 8 by reaction with appropriate reagents, using methods known in the art.

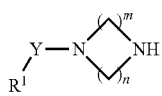

18

For instance, amine 18 is reacted with a suitable carboxylic acid of formula $R^2$—COOH (9), leading to compounds of formula 17A. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Compounds of formula 17 wherein Z is $S(O)_2$ can be represented by general structure 17B. $R^1$, $R^2$, m and n are as described above.

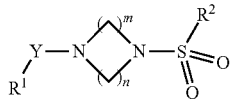

17B

Sulfonamides 17B can be produced from amine precursors of general formula 18 by reaction with appropriate reagents, using methods known in the art. For instance, amine 18 is reacted with a suitable sulfonyl chloride of formula $R^2$—$SO_2Cl$ (10), leading to compounds of formula 17B. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Compounds of formula (I) wherein X is N W is —$(CR^9R^{10})_p$—, $R^{10}$ is H and p is 1 can be represented by general structure 17C. $R^1$, $R^2$, m and n are as described above.

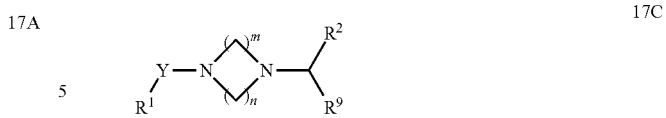

17C

Compounds of formula 17C can be produced from amine precursors 18 by reaction with appropriate reagents, using methods known in the art.

For instance, amine 18 is reacted with aldehyde or ketone, $R^2$—C(O)—$R^9$ (21) in the presence of a suitable reducing agent, e. g., sodium triacetoxyborohydride, sodium borohydride, or sodium cyanoborohydride. The reaction is performed in a suitable solvent, e. g., dichloromethane, 1,2-dichloroethane, acetic acid, methanol, or mixtures thereof, at temperatures between 0° C. and the boiling point of the solvent.

Alternatively, amine 18 is reacted with halide, $R^2$—CH($R^9$)-Hal (22) (Hal is Cl, Br, or I) in the presence of a suitable base, e. g., potassium carbonate, cesium carbonate, or triethylamine. The reaction is performed in a suitable solvent, e. g., methanol, acetone, acetonitrile, or N,N,dimethylfomamide, at temperatures between 0° C. and the boiling point of the solvent.

Aldehydes or ketones (21) and halides (22) are commercially available or can be produced as described herein or in the literature.

Amines of formula 18 can be prepared from the suitably protected precursors 19.

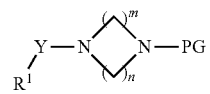

19

Suitable protective groups (PG) are tert-butoxycarbonyl or benzyloxycarbonyl. The deprotection of intermediates 19 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Compounds of formula 19 can be synthesised from amine precursors 20 and appropriate reagents, using methods well known in the art.

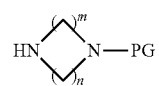

20

For instance, amine 20 is reacted with a suitable carboxylic acid of formula $R^1$—Y—OH (2) leading to a compound of formula (I), wherein Y is —$(CH_2)_qC(O)$—, —(CH=

CH)$_r$—C(O)—, or —(CH≡CH)$_r$—C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 20 can also be reacted with suitable acylating reagents such as acyl chlorides of formula R$^1$—Y—Cl (3) to lead to compounds of formula (I), wherein Y is —(CH$_2$)$_q$C(O)—, —(CH═CH)$_r$—C(O)—, or —(CH≡CH)$_r$—C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 20 is reacted with a suitable chloroformate ester of formula R$^1$—CH$_2$—O—C(O)—Cl (4), or with an imidazole-1-carboxylate ester of formula (5), leading to a compound of formula (I) wherein Y is —CH$_2$—OC(O)—. The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Amines 20 are commercially available or can be prepared as described herein or in the literature.

Also an embodiment of the present invention is a process to prepare a compound of formula (I) as defined above comprising the reaction of a compound of formula (II) in the presence of a compound of formula (III);

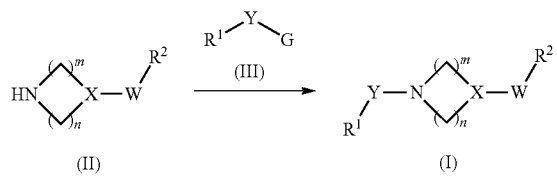

wherein R$^1$, R$^2$, Y, W, X, m and n are as defined herein and in case Y is —(CH$_2$)$_q$C(O)—, —(CH═CH)$_r$—C(O)— or —(CH≡CH)$_r$—C(O)—, then G is halogen or hydroxy and in case Y is —OC(O)—, then G is chloro.

In particular, in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, particularly O-(7-azabenzotriazol-1-yl)-N,N,N',N'-tetramethyluronium hexafluoro-phosphate, in an aprotic solvent such as dichloromethane, tetrahydrofuran, N,N-dimethylformamide, N-methylpyrrolidinone and mixtures thereof, particularly N,N-dimethylformamide, in the presence or absence of a base such as triethylamine, diisopropylethylamine, 4-methylmorpholine and/or 4-(dimethylamino)pyridine, particularly in the presence of 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

Also an object of the invention is a method for the treatment or prophylaxis of ocular conditions, particularly glaucoma, which method comprises administering an effective amount of a compound according to formula (I) as described herein.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

Also an embodiment of the present invention are compounds of formula (I) as described herein, when manufactured according to any one of the described processes.

Assay Procedures
Production of Human Full Length ATX, with and without His Tag
Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 µm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxypropyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:
Assay buffer (50 mM Tris-HCl, 140 mM NaCl, 5 mM KCl, 1 mM $CaCl_2$, 1 mM $MgCl_2$, 0.01% Triton-X-100, pH 8.0;
ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;
MR121 substrate solution: MR121 substrate stock solution (800 µM MR121 substrate in DMSO), diluted to 2-5× final concentration in assay buffer.

Test compounds (10 mM stock in DMSO, 8 µL) were obtained in 384 well sample plates (Corning Costar #3655) and diluted with 8 µL DMSO. Row-wise serial dilutions were made by transferring 8 µL cpd solution to the next row up to row O. The compound and control solutions were mixed five times and 2 µL were transferred to 384 well assay plates (Corning Costar #3702). Then, 15 µL of 41.7 nM ATX solution was added (30 nM final concentration), mixed five times and then incubated for 15 minutes at 30° C. 10 µL of MR121 substrate solution was added (1 µM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

Human Carbonic Anhydrase-II Inhibition Assay

Human carbonic anhydrase II (hCA-II) inhibition was measured by an absorbance method using 4-nitrophenyl acetate (4-NPA) as its substrate. 4-NPA can be catalyzed by active hCA II via a zinc-hydroxide mechanism. The nitrophenolate in the products can be ionized to generate a bright yellow anion with high absorbance at 348 to 400 nm, as reported in the literature (Armstrong et al., J. Biol. Chem. 1966, 241, 5137-5149). OD340 nm was chosen for detecting hCA II substrate conversion.

Assay working solutions were made as follows:
Assay buffer: 50 mM MOPS, 33 mM $Na_2SO_4$, 1 mM EDTA, 0.5 mg/mL BSA, pH 7.5;
Enzyme solution: hCA-II (human, full length) stock solution (1.0 mg/mL in 20 mM HEPES, 50 mM NaCl, pH 7.4), diluted to 2133× final concentration in assay buffer;
4-NPA substrate solution: 4-NPA substrate stock solution (250 mM in DMSO, stored at −20° C.), diluted to 50× final concentration in deionized water.

Test compounds (10 mM stock in DMSO, 100 µL) were obtained in 96-well sample plates (Corning Costar #3655)

and diluted to 0.5 mM. Column-wise serial dilutions were made by transferring 20 µL compound solutions to the next column, from column 3 up to 22. After this, 1.2 µL were transferred to 384 well assay plates (Corning Costar #3701). Then 30 µL of 16 nM hCA II solution was added (8 nM final concentration), mixed five times. 30 µL of 4-NPA substrate solution was added (2.5 mM final concentration), mixed five times. Absorbance at 340 nm was then measured immediately as time zero. The assay plates were incubated at room temperature for 1 hour and then measured as time 1 hour (Perkin Elmer EnVision 2103; Filter: Photometric 340; Light intensity 60%; Number of flashes: 10). $IC_{50}$ values and $K_i$ values were calculated from these readouts.

| Ex | ATX IC50 (µM) | CA-II IC50 (µM) |
|---|---|---|
| 1.00 | 0.023 | 0.0096 |
| 1.01 | 0.018 | 0.2925 |
| 1.02 | 0.312 | 0.072 |
| 1.03 | 0.073 | |
| 1.04 | 0.008 | |
| 2.00 | 0.008 | 0.0344 |
| 2.01 | 0.002 | 0.0013 |
| 2.02 | 0.007 | 0.0155 |
| 3.00 | 0.002 | 0.0211 |
| 3.00 | 0.009 | 0.0094 |
| 4.00 | 0.001 | 0.0176 |
| 4.01 | 0.002 | 0.0342 |
| 4.02 | 0.013 | 0.0343 |
| 5.00 | 0.014 | 1.0986 |
| 5.01 | 0.004 | 0.0207 |
| 5.02 | 0.005 | 0.0271 |
| 5.03 | 0.001 | 0.1089 |
| 5.04 | 0.005 | 0.0133 |
| 5.05 | 0.067 | |
| 5.06 | 0.027 | |
| 5.07 | 0.024 | 0.1344 |
| 5.08 | 0.014 | 0.1118 |
| 5.09 | 0.009 | 0.0685 |
| 6.00 | 0.001 | 0.0067 |
| 6.01 | 0.004 | 0.0063 |
| 6.02 | 0.005 | 0.0018 |
| 6.03 | 0.001 | 0.007 |
| 6.04 | 0.005 | 0.0113 |
| 6.05 | 0.006 | 0.01 |
| 6.06 | 0.004 | 0.014 |
| 6.07 | 0.003 | 0.0131 |
| 6.08 | 0.01 | 0.017 |
| 6.09 | 0.012 | 0.0172 |
| 6.10 | 0.002 | 0.0095 |
| 6.11 | 0.01 | 0.0062 |
| 6.12 | 0.008 | 0.0013 |
| 6.13 | 0.001 | 0.0175 |
| 6.14 | 0.005 | 0.0008 |
| 6.15 | 0.013 | 0.0079 |
| 6.16 | 0.004 | 0.0123 |
| 6.17 | 0.002 | 0.0071 |
| 6.18 | 0.001 | 0.0129 |
| 6.19 | 0.002 | 0.0178 |
| 6.20 | 0.019 | 0.0206 |
| 6.21 | 0.068 | 0.015 |
| 6.22 | 0.011 | 0.0072 |
| 6.23 | 0.004 | 0.0029 |
| 6.24 | 0.009 | 0.0089 |
| 6.25 | 0.01 | 0.0062 |
| 6.26 | 0.008 | 0.0124 |
| 6.27 | 0.001 | 0.0092 |
| 6.28 | 0.004 | 0.0102 |
| 6.29 | 0.009 | 0.0084 |
| 6.30 | 0.015 | 0.0024 |
| 6.31 | 0.01 | 0.0178 |
| 6.32 | 0.003 | 0.0041 |
| 6.33 | 0.003 | 0.02 |
| 6.34 | 0.012 | 0.0079 |
| 6.35 | 0.014 | 0.0198 |
| 6.36 | 0.062 | 0.0606 |
| 6.37 | 0.006 | 0.0163 |
| 6.38 | 0.001 | 0.0073 |
| 6.39 | 0.001 | 0.008 |
| 6.40 | 0.007 | 0.009 |
| 6.41 | 0.001 | 0.0025 |
| 6.42 | 0.003 | |
| 6.43 | 0.006 | |
| 6.44 | 0.007 | |
| 6.45 | 0.001 | 0.0051 |
| 7.00 | 0.003 | |
| 7.01 | 0.072 | 0.0207 |
| 7.02 | 0.024 | 0.1174 |
| 8.00 | 0.005 | |
| 8.01 | 0.01 | 0.2393 |
| 8.02 | 0.006 | 0.1463 |
| 9.00 | 0.027 | |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; PS-BEMP=polystyrene-bound 2-tert-butylimino-2-diethylamino-1,3-dimethylperhydro-1,3,2-diazaphosphorine; sat.=saturated Example 1

[2-[(5-Methyltetrazol-2-yl)methyl]-4-(trifluoromethyl)phenyl]methyl 4-(2-fluoro-4-sulfamoylphenyl)piperazine-1-carboxylate

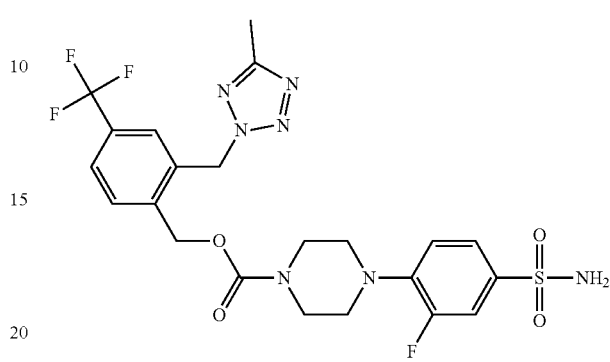

To a solution of [2-[(5-methyltetrazol-2-yl)methyl]-4-(trifluoromethyl)phenyl]methanol (intermediate 1; 30 mg, 110 μmol) in acetonitrile (2 mL) was added 1,1'-carbonyldiimidazole (17.9 mg, 110 μmol) at room temperature. The reaction mixture was heated to 50° C. and stirred for 2 h, then a suspension of 3-fluoro-4-piperazin-1-ylbenzenesulfonamide (CAS-RN 847971-84-0; 28.6 mg, 110 μmol) and triethylamine (55.8 mg, 551 μmol) in acetonitrile (2 mL) was added and the reaction mixture was heated to reflux. After 15 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (15 mg, 24%). White solid, MS: 558.1 (M+H)$^+$.

The following examples were prepared according to example 1, replacing 3-fluoro-4-piperazin-1-ylbenzenesulfonamide by the appropriate amine or carbamate and [2-[(5-methyltetrazol-2-yl)methyl]-4-(trifluoromethyl)phenyl]methanol by the appropriate alcohol. In the cases where the tert-butyl carbamate derivatives of the amines are used as starting materials (examples 1.03 and 1.04), the carbamates were first deprotected with trifluoroacetic acid in analogy to example 6.

| Ex. | Systematic Name | Amine or carbamate/Alcohol | MS, m/e |
|---|---|---|---|
| 1.01 | [2-cyclopropyl-6-(oxan-4-ylmethoxy)pyridin-4-yl]methyl 4-[(4-sulfamoylphenyl)methyl]piperidine-1-carboxylate | 4-(piperidin-4-ylmethyl)benzenesulfonamide hydrochloride (CAS-RN 333986-77-9)/[2-cyclopropyl-6-(oxan-4-ylmethoxy)pyridin-4-yl]methanol (intermediate 6) | 544.4 (M + H)$^+$ |

-continued

| Ex. | Systematic Name | Amine or carbamate/Alcohol | MS, m/e |
| --- | --- | --- | --- |
| 1.02 | [5-cyano-3-(2,2-dimethylpropanoylamino)pyridin-2-yl]methyl 4-[(4-sulfamoylphenyl)methyl]piperidine-1-carboxylate | 4-(piperidin-4-ylmethyl)benzenesulfonamide hydrochloride (CAS-RN 333986-77-9)/(N-[5-cyano-2-(hydroxymethyl)pyridin-3-yl]-2,2-dimethylpropanamide (intermediate 12) | 512.4 (M − H)⁻ |
| 1.03 | [5-chloro-3-[(5-methyltetrazol-2-yl)methyl]pyridin-2-yl]methyl 4-(2-fluoro-4-sulfamoylphenyl)sulfonylpiperidine-1-carboxylate | tert-butyl 4-(2-fluoro-4-sulfamoylphenyl)sulfonyl-piperidine-1-carboxylate (intermediate 11)/[5-chloro-3-[(5-methyltetrazol-2-yl)methyl]pyridin-2-yl]methanol (intermediate 14) | 588.2 (M + H)⁺ |
| 1.04 | [2-[(5-methyltetrazol-2-yl)methyl]-4-(trifluoromethyl)phenyl]methyl 4-(2-fluoro-4-sulfamoylphenyl)sulfonylpiperidine-1-carboxylate | (tert-butyl 4-((2-fluoro-4-sulfamoylphenyl)sulfonyl)-piperidine-1-carboxylate/2-((5-methyl-2H-tetrazol-2-yl)methyl)-4-(trifluoromethyl)phenyl)methanol (intermediate 1) | 619.3 (M − H)⁻ |

Example 2

2-Fluoro-4-[[4-[3-[2-[(5-methyltetrazol-2-yl)methyl]-4-(trifluoromethyl)phenyl]propanoyl]piperazin-1-yl]methyl]benzenesulfonamide

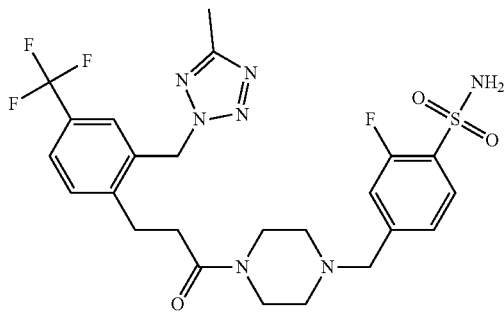 [SMILES: Cc1nnn(Cc2cc(C(F)(F)F)ccc2CCC(=O)N2CCN(Cc3ccc(S(N)(=O)=O)c(F)c3)CC2)n1]

To a solution of tert-butyl 4-(3-fluoro-4-sulfamoylbenzoyl)piperazine-1-carboxylate (CAS-RN 1395398-34-1; 150 mg, 387 µmol) in tetrahydrofuran (3 mL) was added borane tetrahydrofuran complex (1 M in tetrahydrofuran; 1.16 mL, 1.16 mmol) at room temperature, then after 14 h the reaction mixture was heated to 60° C. for 4 h, then 2 M aq, hydrochloric acid solution (2 mL) and additionally hydrochloric acid (25% in water; 1.0 mL, 8.2 mmol) were added dropwise. The mixture was stirred at 60° C. for 45 min, then the mixture was directly evaporated at high vacuum and the residue was combined with N,N-dimethylformamide (3 mL) and N-methylmorpholine (392 ng, 3.87 mmol), 3-[2-[(5-methyltetrazol-2-yl)methyl]-4-(trifluoroethyl)phenyl]propanoic acid (CAS-RN 1646783-83-6; 122 mg, 387 µmol) and O-(7-azabenzotriazol-1-yl)-N,N,N',N'-tetramethyluronium hexafluoro-phosphate (147 ng, 387 µmol), then after 48 h at room temperature the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane/methanol to dichloromethane/methanol/25% aq. ammonia solution 90:10:0.25) produced the title compound (87 mg, 40%). Colourless gum, MS: 570.3 (M+H)$^+$.

The following examples were prepared according to example 2, replacing tert-butyl 4-(3-fluoro-4-sulfamoylbenzoyl)piperazine-1-carboxylate by the appropriate carbamate and 3-[2-[(5-methyltetrazol-2-yl)methyl]-4-(trifluoromethyl)phenyl]propanoic acid by the appropriate carboxylic acid.

| Ex. | Systematic Name | Carbamate/Carboxylic acid | MS, m/e |
|---|---|---|---|
| 2.01 | 3-fluoro-4-[[4-[3-[2-[(5-methyltetrazol-2-yl)methyl]-4-(trifluoromethyl)phenyl]-propanoyl]piperazin-1-yl]methyl]benzenesulfonamide | tert-butyl 4-(2-fluoro-4-sulfamoylbenzoyl)piperazine-1-carboxylate (intermediate 5)/3-[2-[(5-methyltetrazol-2-yl)methyl]-4-(trifluoromethyl)phenyl]propanoic acid (CAS-RN 1646783-83-6) | 570.4 (M + H)$^+$ |
| 2.02 | 4-[[4-[2-cyclopropyl-6-(oxan-4-ylmethoxy)pyridine-4-carbonyl]piperazin-1-yl]methyl]-3-fluorobenzenesulfonamide | tert-butyl 4-(2-fluoro-4-sulfamoylbenzoyl)piperazine-1-carboxylate (intermediate 5)/2-cyclopropyl-6-(oxan-4-ylmethoxy)pyridine-4-carboxylic acid (CAS-RN 1810776-23-8) | 533.3 (M + H)$^+$ |

Example 3

2-Fluoro-4-[4-[3-[2-[(5-methyltetrazol-2-yl)methyl]-4-(trifluoromethyl)phenyl]propanoyl]piperazine-1-carbonyl]benzenesulfonamide

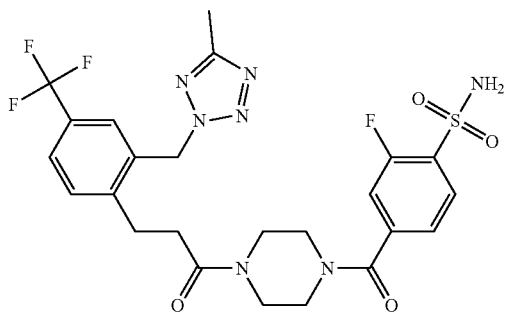 [SMILES: Cc1nnn(Cc2cc(C(F)(F)F)ccc2CCC(=O)N2CCN(C(=O)c3ccc(S(N)(=O)=O)c(F)c3)CC2)n1]

The title compound was obtained as a side product in the preparation of example 2 (48 mg, 21%). White solid, MS: 584.3 (M+H)+.

Example 4

3,5-Difluoro-4-[4-[3-[2-[(5-methyltetrazol-2-yl)methyl]-4-(trifluoromethyl)phenyl]propanoyl]piperazine-1-carbonyl]benzenesulfonamide

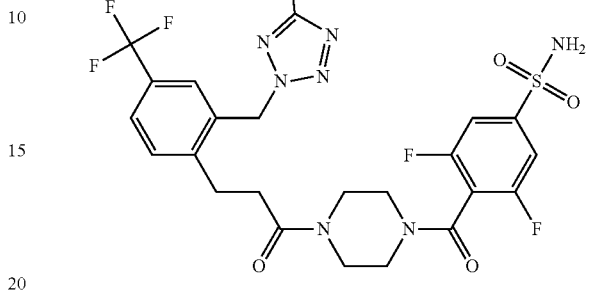

To a solution of 3-[2-[(5-methyltetrazol-2-yl)methyl]-4-(trifluoromethyl)phenyl]-1-piperazin-1-ylpropan-1-one (intermediate 2; 40 mg, 100 μmol) in N,N-dimethylformamide (3 mL) was added N-methylmorpholine (40.6 mg, 402 μmol), 2,6-difluoro-4-sulfamoylbenzoic acid (intermediate 3; 26.2 mg, 110 μmol) and O-(7-azabenzotriazol-1-yl)-N,N,N',N'-tetramethyluronium hexafluoro-phosphate (42 mg, 110 μmol), then after 18 h at room temperature the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (51 mg, 84%). White solid, MS: 602.3 (M+H)+.

The following examples were prepared according to example 4, replacing 2,6-difluoro-4-sulfamoylbenzoic acid (intermediate 3) by the appropriate carboxylic acid.

| Ex. | Systematic Name | Carboxylic acid | MS, m/e |
| --- | --- | --- | --- |
| 4.01 | 3-fluoro-4-[4-[3-[2-[(5-methyltetrazol-2-yl)methyl]-4-(trifluoromethyl)phenyl]-propanoyl]piperazine-1-carbonyl]benzenesulfonamide | 2-fluoro-4-sulfamoylbenzoic acid (CAS-RN 714968-42-0) | 584.3 (M + H)+ |

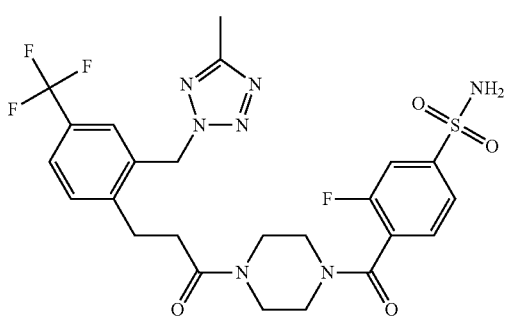 [SMILES: Cc1nnn(Cc2cc(C(F)(F)F)ccc2CCC(=O)N2CCN(C(=O)c3c(F)cc(S(N)(=O)=O)cc3F)CC2)n1]

-continued

| Ex. | Systematic Name | Carboxylic acid | MS, m/e |
|---|---|---|---|
| 4.02 | 4-[4-[3-[2-[(5-methyltetrazol-2-yl)methyl]-4-(trifluoromethyl)phenyl]-propanoyl]piperazine-1-carbonyl]benzenesulfonamide | 4-sulfamoylbenzoic acid (CAS-RN 138-41-0) | 566.2 (M + H)+ |

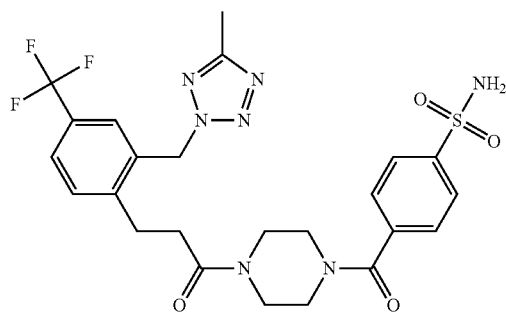

Example 5

3-[[1-[2-Cyclopropyl-6-(oxan-4-ylmethoxy)pyridine-4-carbonyl]piperidin-4-yl]methyl]-4-fluorobenzenesulfonamide

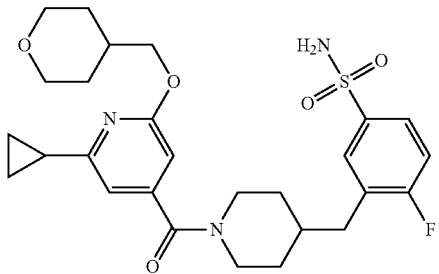 [SMILES: NS(=O)(=O)c1ccc(F)c(CC2CCN(C(=O)c3cc(OCC4CCOCC4)nc(C4CC4)c3)CC2)c1]

To a solution of 4-fluoro-3-(piperidin-4-ylmethyl)benzenesulfonamide hydrochloride (intermediate 7; 51.6 mg, 159 μmol) in N,N-dimethylformamide (3 mL) was added N-methylmorpholine (72.9 mg, 721 μmol), 2-cyclopropyl-6-(oxan-4-ylmethoxy)pyridine-4-carboxylic acid (CAS-RN 1810776-23-8; 40 mg, 144 μmol) and O-(7-azabenzotriazol-1-yl)-N,N,N',N'-tetramethyluronium hexafluoro-phosphate (60.3 mg, 159 μmol), then after 18 h at room temperature the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (75 mg, 98%). White solid, MS: 532.3 (M+H)+.

The following examples were prepared according to example 5, replacing 4-fluoro-3-(piperidin-4-ylmethyl)benzenesulfonamide hydrochloride by the appropriate amine and 2-cyclopropyl-6-(oxan-4-ylmethoxy)pyridine-4-carboxylic acid by the appropriate carboxylic acid.

| Ex. | Systematic Name | Amine/Carboxylic acid | MS, m/e |
|---|---|---|---|
| 5.01 | 3-fluoro-4-[1-[3-[2-[(5-methyltetrazol-2-yl)methyl]-4-(trifluoromethyl)phenyl]propanoyl]piperidin-4-yl]sulfanylbenzenesulfonamide | 3-fluoro-4-piperidin-4-ylsulfanylbenzenesulfonamide hydrochloride (intermediate 8)/ 3-[2-[(5-methyltetrazol-2-yl)methyl]-4-(trifluoromethyl)-phenyl]propanoic acid (CAS-RN 1646783-83-6) | 587.3 (M + H)+ |

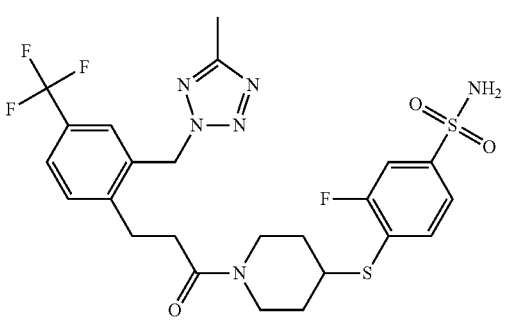

| Ex. | Systematic Name | Amine/Carboxylic acid | MS, m/e |
|---|---|---|---|
| 5.02 | 3-fluoro-4-[4-[3-[2-[(5-methyltetrazol-2-yl)methyl]-4-(trifluoromethyl)phenyl]-propanoyl]piperazin-1-yl]benzenesulfonamide | 3-fluoro-4-piperazin-1-ylbenzenesulfonamide (CAS-RN 847971-84-0)/3-[2-[(5-methyltetrazol-2-yl)methyl]-4-(trifluoromethyl)phenyl]-propanoic acid (CAS-RN 1646783-83-6) | 556.2 (M + H)⁺ |
| 5.03 | 4-[[1-[2-cyclopropyl-6-(oxan-4-ylmethoxy)pyridine-4-carbonyl]piperidin-4-yl]methyl]benzenesulfonamide | 4-(piperidin-4-ylmethyl)benzenesulfonamide hydrochloride (CAS-RN 333986-77-9)/2-cyclopropyl-6-(oxan-4-ylmethoxy)pyridine-4-carboxylic acid (CAS-RN 1810776-23-8) | 514.4 (M + H)⁺ |
| 5.04 | 4-[[1-[3-[2-[(5-methyltetrazol-2-yl)methyl]-4-(trifluoromethyl)phenyl]-propanoyl]piperidin-4-yl]methyl]benzenesulfonamide | 4-(piperidin-4-ylmethyl)benzenesulfonamide hydrochloride (CAS-RN 333986-77-9)/3-[2-[(5-methyltetrazol-2-yl)methyl]-4-(trifluoromethyl)phenyl]-propanoic acid (CAS-RN 1646783-83-6) | 551.3 (M + H)⁺ |

| Ex. | Systematic Name | Amine/Carboxylic acid | MS, m/e |
|---|---|---|---|
| 5.05 | 4-[[1-[3-[2-[(5-methyltetrazol-2-yl)methyl]-4-(trifluoromethyl)phenyl]-propanoyl]pyrrolidin-2-yl]methoxy]benzenesulfonamide | 4-(pyrrolidin-2-ylmethoxy)benzenesulfonamide hydrochloride (CAS-RN 1803591-06-1)/3-[2-[(5-methyltetrazol-2-yl)methyl]-4-(trifluoromethyl)phenyl]-propanoic acid (CAS-RN 1646783-83-6) | 553.2 $(M + H)^+$ |
| 5.06 | 4-[[1-[3-[2-[(5-methyltetrazol-2-yl)methyl]-4-(trifluoromethyl)phenyl]-propanoyl]pyrrolidin-3-yl]methoxy]benzenesulfonamide | 4-(pyrrolidin-3-ylmethoxy)benzenesulfonamide hydrochloride (CAS-RN 1803590-92-92)/3-[2-[(5-methyltetrazol-2-yl)methyl]-4-(trifluoromethyl)phenyl]-propanoic acid (CAS-RN 1646783-83-6) | 553.2 $(M + H)^+$ |
| 5.07 | 4-[1-[3-[2-[(5-methyltetrazol-2-yl)methyl]-4-(trifluoromethyl)phenyl]propanoyl]-piperidin-4-yl]benzenesulfonamide | 4-piperidin-4-ylbenzenesulfonamide (CAS-RN 119737-31-4)/3-[2-[(5-methyltetrazol-2-yl)methyl]-4-(trifluoromethyl)phenyl]-propanoic acid (CAS-RN 1646783-83-6) | 537.2 $(M + H)^+$ |

| Ex. | Systematic Name | Amine/Carboxylic acid | MS, m/e |
|---|---|---|---|
| 5.08 | 4-[4-[3-[2-[(5-methyltetrazol-2-yl)methyl]-4-(trifluoromethyl)phenyl]-propanoyl]piperazin-1-yl]benzenesulfonamide | 4-piperazin-1-ylbenzenesulfonamide (CAS-RN 170856-87-8)/3-[2-[(5-methyltetrazol-2-yl)methyl]-4-(trifluoromethyl)phenyl]-propanoic acid (CAS-RN 1646783-83-6) | 538.2 (M + H)+ |
| 5.09 | 4-fluoro-3-[[1-[3-[2-[(5-methyltetrazol-2-yl)methyl]-4-(trifluoromethyl)phenyl]-propanoyl]piperidin-4-yl]methyl]benzenesulfonamide | 4-fluoro-3-(piperidin-4-ylmethyl)benzenesulfonamide hydrochloride (intermediate 7)/3-[2-[(5-methyltetrazol-2-yl)methyl]-4-(trifluoromethyl)phenyl]-propanoic acid (CAS-RN 1646783-83-6) | 569.3 (M + H)+ |

Example 6

2,3-Difluoro-4-[1-[3-[2-[(5-methyltetrazol-2-yl)methyl]-4-(trifluoromethyl)phenyl]propanoyl]piperidin-4-yl]sulfanylbenzenesulfonamide

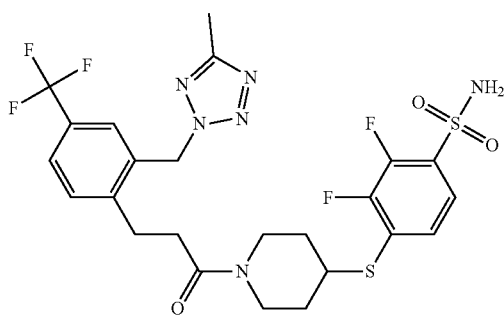 [SMILES: Cc1nnn(Cc2cc(C(F)(F)F)ccc2CCC(=O)N2CCC(Sc3ccc(S(N)(=O)=O)c(F)c3F)CC2)n1]

To a solution of tert-butyl 4-(2,3-difluoro-4-sulfamoylphenyl)sulfanylpiperidine-1-carboxylate (intermediate 9.2; 31 mg, 60 μmol) in dichloromethane (3 mL) was added trifluoroacetic acid (137 mg, 1.2 mmol) at room temperature. The reaction mixture was stirred at 40° C. for 80 min, then the mixture was directly evaporated and the residue was taken up in N,N-dimethylformamide (3 mL) and N-methylmorpholine (61.9 mg, 600 μmol), 3-[2-[(5-methyltetrazol-2-yl)methyl]-4-(trifluoromethyl)phenyl]propanoic acid (CAS-RN 1646783-83-6; 20.7 mg, 65.9 μmol) and O-(7-azabenzotriazol-1-yl)-N,N,N',N'-tetramethyluronium hexafluoro-phosphate (25.3 mg, 65.9 μmol) were added, After 18 h at room temperature the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (27 mg, 74%). White solid, MS: 605.2 (M+H)+.

The following examples were prepared according to example 6, replacing tert-butyl 4-(2,3-difluoro-4-sulfamoylphenyl)sulfanylpiperidine-1-carboxylate (intermediate 9.2) by the appropriate carbamate and 3-[2-[(5-methyltetrazol-2-yl)methyl]-4-(trifluoromethyl)phenyl]propanoic acid (CAS-RN 1646783-83-6) by the appropriate carboxylic acid.

| Ex. | Systematic Name | Carbamate/Carboxylic acid | MS, m/e |
|---|---|---|---|
| 6.01 | 2,3-difluoro-4-[1-[3-[2-[(5-methyltetrazol-2-yl)methyl]-4-(trifluoromethyl)phenyl]propanoyl]-piperidin-4-yl]sulfinylbenzenesulfonamide | tert-butyl 4-(2,3-difluoro-4-sulfamoylphenyl)sulfinyl-piperidine-1-carboxylate (intermediate 10.2)/3-[2-[(5-methyltetrazol-2-yl)methyl]-4-(trifluoromethyl)phenyl]-propanoic acid (CAS-RN 1646783-83-6) | 621.2 (M + H)+ |
| | 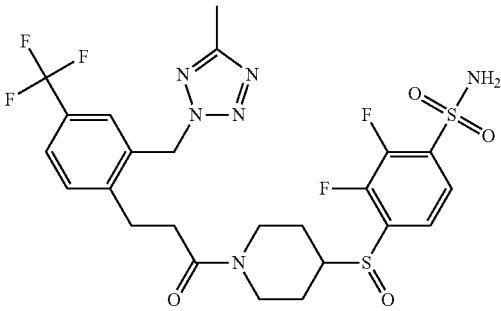 | | |
| 6.02 | 2,3-difluoro-4-[1-[3-[2-[(5-methyl-tetrazol-2-yl)methyl]-4-(trifluoromethyl)-phenyl]propanoyl]piperidin-4-yl]sulfonylbenzenesulfonamide | tert-butyl 4-(2,3-difluoro-4-sulfamoylphenyl)sulfonyl-piperidine-1-carboxylate (intermediate 15)/3-[2-[(5-methyltetrazol-2-yl)methyl]-4-(trifluoromethyl)phenyl]-propanoic acid (CAS-RN 1646783-83-6) | 637.2 (M + H)+ |
| | 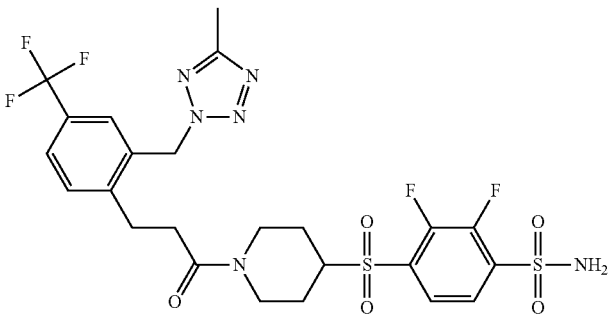 | | |
| 6.03 | 2,3-difluoro-4-[2-[1-[3-[2-[(5-methyltetrazol-2-yl)methyl]-4-(trifluoromethyl)phenyl]propanoyl]-piperidin-4-yl]ethylsulfonyl]benzenesulfonamide | tert-butyl 4-[2-(2,3-difluoro-4-sulfamoylphenyl)sulfonylethyl]-piperidine-1-carboxylate (intermediate 15.3)/2-cyclopropyl-6-(oxan-4-ylmethoxy)pyridine-4-carboxylic acid (CAS-RN 1810776-23-8) | 665.2 (M + H)+ |
| | 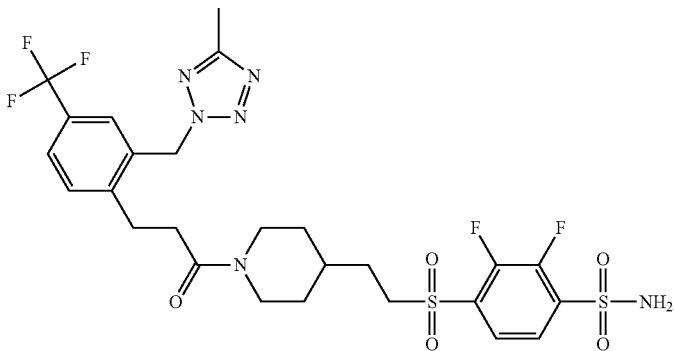 | | |

| Ex. | Systematic Name | Carbamate/Carboxylic acid | MS, m/e |
|---|---|---|---|
| 6.04 | 2-[1-[3-[2-[(5-methyltetrazol-2-yl)methyl]-4-(trifluoromethyl)phenyl]propanoyl]-piperidin-4-yl]sulfanyl-1,3-thiazole-5-sulfonamide | tert-butyl 4-[(5-sulfamoyl-1,3-thiazol-2-yl)sulfamoyl]piperidine-1-carboxylate (intermediate 9.5)/3-[2-[(5-methyltetrazol-2-yl)methyl]-4-(trifluoromethyl)phenyl]propanoic acid (CAS-RN 1646783-83-6) | 576.1 (M + H)+ |
| 6.05 | 2-[1-[3-[2-[(5-methyltetrazol-2-yl)methyl]-4-(trifluoromethyl)phenyl]-propanoyl]piperidin-4-yl]sulfonyl-1,3-thiazole-5-sulfonamide | tert-butyl 4-[(5-sulfamoyl-1,3-thiazol-2-yl)sulfonyl]piperidine-1-carboxylate (intermediate 15.2)/3-[2-[(5-methyltetrazol-2-yl)methyl]-4-(trifluoromethyl)phenyl]propanoic acid (CAS-RN 1646783-83-6) | 608.1 (M + H)+ |
| 6.06 | 2-[2-[1-[3-[2-[(5-methyltetrazol-2-yl)methyl]-4-(trifluoromethyl)phenyl]propanoyl]-piperidin-4-yl]ethylsulfinyl]-1,3-thiazole-5-sulfonamide | tert-butyl 4-[2-[(5-sulfamoyl-1,3-thiazol-2-yl)sulfinyl]ethyl]piperidine-1-carboxylate (intermediate 10.5)/2-cyclopropyl-6-(oxan-4-ylmethoxy)pyridine-4-carboxylic acid (CAS-RN 1810776-23-8) | 620.2 (M + H)+ |

-continued

| Ex. | Systematic Name | Carbamate/Carboxylic acid | MS, m/e |
|---|---|---|---|
| 6.07 | 3-[2-[(5-methyltetrazol-2-yl)methyl]-4-(trifluoromethyl)phenyl]propanoic acid (CAS-RN 1646783-83-6) | tert-butyl 4-[(2-fluoro-4-sulfamoylphenyl)sulfanylmethyl]-piperidine-1-carboxylate (intermediate 9)/3-[2-[(5-methyltetrazol-2-yl)methyl]-4-(trifluoromethyl)phenyl]propanoic acid (CAS-RN 1646783-83-6) | 601.3 (M + H)+ |
| 6.08 | 3-fluoro-4-[[1-[3-[2-[(5-methyltetrazol-2-yl)methyl]-4-(trifluoromethyl)phenyl]propanoyl]-piperidin-4-yl]methylsulfinyl]-benzenesulfonamide | tert-butyl 4-[(2-fluoro-4-sulfamoylphenyl)sulfinylmethyl]-piperidine-1-carboxylate (intermediate 10.1)/3-[2-[(5-methyltetrazol-2-yl)methyl]-4-(trifluoromethyl)phenyl]propanoic acid (CAS-RN 1646783-83-6) | 617.3 (M + H)+ |
| 6.09 | 3-fluoro-4-[[1-[3-[2-[(5-methyltetrazol-2-yl)methyl]-4-(trifluoromethyl)phenyl]propanoyl]-piperidin-4-yl]methylsulfonyl]-benzenesulfonamide | tert-butyl 4-[(2-fluoro-4-sulfamoylphenyl)sulfonylmethyl]-piperidine-1-carboxylate (intermediate 11.1)/2-cyclopropyl-6-(oxan-4-ylmethoxy)pyridine-4-carboxylic acid (CAS-RN 1810776-23-8) | 633.2 (M + H)+ |

-continued

| Ex. | Systematic Name | Carbamate/Carboxylic acid | MS, m/e |
|---|---|---|---|
| 6.10 | 3-fluoro-4-[1-[3-[2-[(5-methyltetrazol-2-yl)methyl]-4-(trifluoromethyl)phenyl]propanoyl]-azetidin-3-yl]sulfanylbenzenesulfonamide 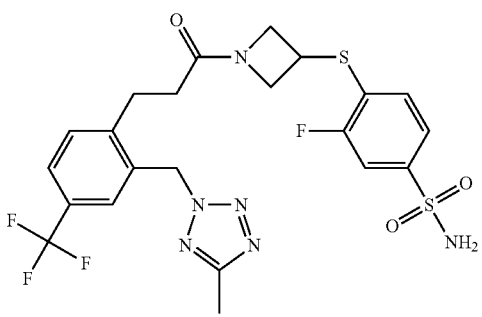 | tert-butyl 3-(2-fluoro-4-sulfamoylphenyl)sulfanylazetidine-1-carboxylate (intermediate 9.3)/3-[2-[(5-methyltetrazol-2-yl)methyl]-4-(trifluoromethyl)phenyl]propanoic acid (CAS-RN 1646783-83-6) | 559.2 (M + H)⁺ |
| 6.11 | 3-fluoro-4-[1-[3-[2-[(5-methyltetrazol-2-yl)methyl]-4-(trifluoromethyl)phenyl]propanoyl]-azetidin-3-yl]sulfinylbenzenesulfonamide 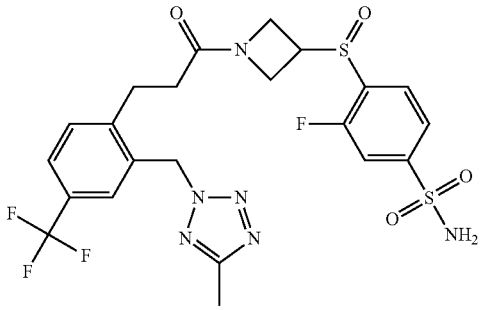 | tert-butyl 3-(2-fluoro-4-sulfamoylphenyl)sulfinylazetidine-1-carboxylate (intermediate 10.3)/ 3-[2-[(5-methyltetrazol-2-yl)methyl]-4-(trifluoromethyl)phenyl]propanoic acid (CAS-RN 1646783-83-6) | 573.2 (M − H)⁻ |
| 6.12 | 3-fluoro-4-[1-[3-[2-[(5-methyltetrazol-2-yl)methyl]-4-(trifluoromethyl)phenyl]propanoyl]-azetidin-3-yl]sulfonylbenzenesulfonamide 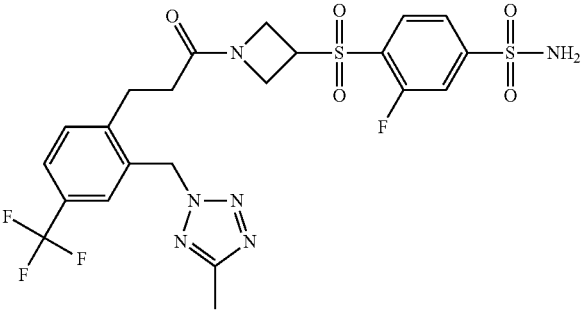 | tert-butyl 3-(2-fluoro-4-sulfamoylphenyl)sulfonylazetidine-1-carboxylate (intermediate 15.1)/ 2-cyclopropyl-6-(oxan-4-ylmethoxy)pyridine-4-carboxylic acid (CAS-RN 1810776-23-8) | 589.2 (M − H)⁻ |

-continued

| Ex. | Systematic Name | Carbamate/Carboxylic acid | MS, m/e |
|---|---|---|---|
| 6.13 | 3-fluoro-4-[1-[3-[2-[(5-methyltetrazol-2-yl)methyl]-4-(trifluoromethyl)phenyl]propanoyl]-piperidin-4-yl]sulfinylbenzenesulfonamide | tert-butyl 4-(2-fluoro-4-sulfamoylphenyl)sulfinylpiperidine-1-carboxylate (intermediate 10)/3-[2-[(5-methyltetrazol-2-yl)methyl]-4-(trifluoromethyl)phenyl]propanoic acid (CAS-RN 1646783-83-6) | 603.2 (M + H)+ |
| 6.14 | 3-fluoro-4-[1-[3-[2-[(5-methyltetrazol-2-yl)methyl]-4-(trifluoromethyl)phenyl]propanoyl]-piperidin-4-yl]sulfonylbenzenesulfonamide | tert-butyl 4-(2-fluoro-4-sulfamoylphenyl)sulfonylpiperidine-1-carboxylate (intermediate 11)/3-[2-[(5-methyltetrazol-2-yl)methyl]-4-(trifluoromethyl)phenyl]propanoic acid (CAS-RN 1646783-83-6) | 619.2 (M + H)+ |
| 6.15 | 3-fluoro-4-[2-[1-[3-[2-[(5-methyltetrazol-2-yl)methyl]-4-(trifluoromethyl)phenyl]propanoyl]-piperidin-4-yl]ethylsulfanyl]benzenesulfonamide | tert-butyl 4-[2-(2-fluoro-4-sulfamoylphenyl)sulfamoylethyl]-piperidine-1-carboxylate (intermediate 9.4)/2-cyclopropyl-6-(oxan-4-ylmethoxy)pyridine-4-carboxylic acid (CAS-RN 1810776-23-8) | 613.3 (M − H)− |

-continued

| Ex. | Systematic Name | Carbamate/Carboxylic acid | MS, m/e |
|---|---|---|---|
| 6.16 | 3-fluoro-4-[2-[1-[3-[2-[(5-methyltetrazol-2-yl)methyl]-4-(trifluoromethyl)phenyl]propanoyl]-piperidin-4-yl]ethylsulfinyl]benzenesulfonamide 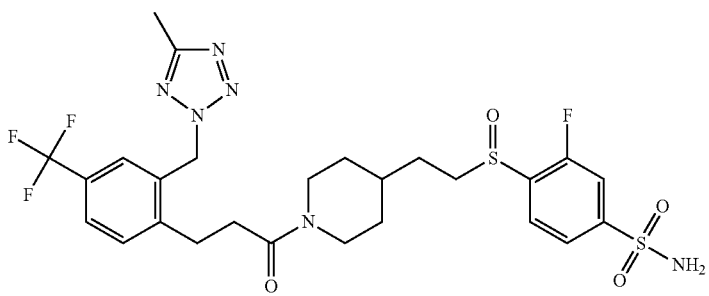 | tert-butyl 4-[2-(2-fluoro-4-sulfamoylphenyl)sulfinylethyl]-piperidine-1-carboxylate (intermediate 10.4)/3-[2-[(5-methyltetrazol-2-yl)methyl]-4-(trifluoromethyl)phenyl]propanoic acid (CAS-RN 1646783-83-6) | 631.3 (M + H)+ |
| 6.17 | 3-fluoro-4-[2-[1-[3-[2-[(5-methyltetrazol-2-yl)methyl]-4-(trifluoromethyl)phenyl]propanoyl]-piperidin-4-yl]ethylsulfonyl]benzenesulfonamide 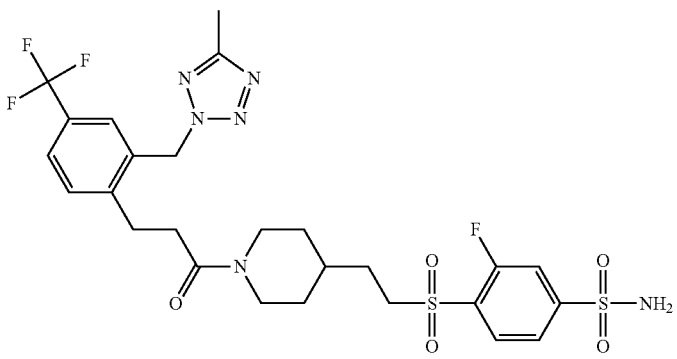 | tert-butyl 4-[2-(2-fluoro-4-sulfamoylphenyl)sulfonylethyl]-piperidine-1-carboxylate (intermediate 16)/3-[2-[(5-methyltetrazol-2-yl)methyl]-4-(trifluoromethyl)phenyl]propanoic acid (CAS-RN 1646783-83-6) | 647.2 (M + H)+ |
| 6.18 | 3-fluoro-4-[2-[1-[6-(2,2,2-trifluoroethoxy)-5-(trifluoromethyl)pyridin-3-carbonyl]piperidin-4-yl]ethylsulfonyl]benzenesulfonamide 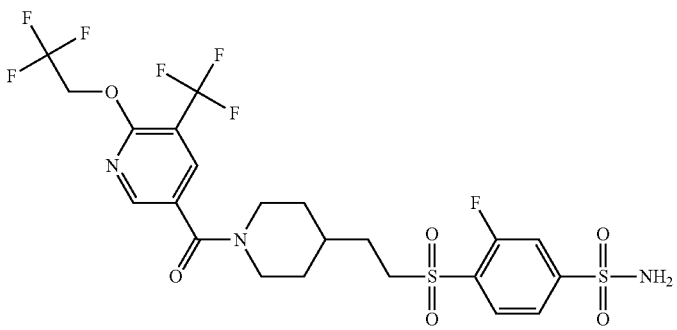 | tert-butyl 4-[2-(2-fluoro-4-sulfamoylphenyl)sulfonylethyl]-piperidine-1-carboxylate (intermediate 16)/6-(2,2,2-trifluoroethoxy)-5-(trifluoromethyl)pyridine-3-carboxylic acid (CAS-RN 1588507-32-7) | 622.1 (M + H)+ |

-continued

| Ex. | Systematic Name | Carbamate/Carboxylic acid | MS, m/e |
|---|---|---|---|
| 6.19 | 3-fluoro-4-[4-[3-[2-[(5-methyltetrazol-2-yl)methyl]-4-(trifluoromethyl)phenyl]propanoyl]-piperazin-1-yl]sulfonylbenzenesulfonamide | tert-butyl 4-(2-fluoro-4-sulfamoylphenyl)sulfonylpiperazine-1-carboxylate (intermediate 4.1)/ 3-[2-[(5-methyltetrazol-2-yl)methyl]-4-(trifluoromethyl)phenyl]propanoic acid (CAS-RN 1646783-83-6) | 618.4 (M − H)$^-$ |
| 6.20 | 4-[[1-[2-cyclopropyl-6-(oxa-4-ylmethoxy)pyridine-4-carbonyl]piperidin-4-yl]methylsulfanyl]-3-fluorobenzenesulfonamide | tert-butyl 4-[(2-fluoro-4-sulfamoylphenyl)sulfanylmethyl]-piperidine-1-carboxylate (intermediate 9)/2-cyclopropyl-6-(oxan-4-ylmethoxy)pyridine-4-carboxylic acid (CAS-RN 1810776-23-8) | 564.3 (M + H)$^+$ |
| 6.21 | 4-[[1-[2-cyclopropyl-6-(oxan-4-ylmethoxy)pyridine-4-carbonyl]piperidin-4-yl]methylsulfinyl]-3-fluorobenzenesulfonamide | tert-butyl 4-[(2-fluoro-4-sulfamoylphenyl)sulfinylmethyl]-piperidine-1-carboxylate (intermediate 10.1)/2-cyclopropyl-6-(oxan-4-ylmethoxy)pyridine-4-carboxylic acid (CAS-RN 1810776-23-8) | 580.3 (M + H)$^+$ |

-continued

| Ex. | Systematic Name | Carbamate/Carboxylic acid | MS, m/e |
|---|---|---|---|
| 6.22 | 4-[[1-[2-cyclopropyl-6-(oxan-4-ylmethoxy)pyridine-4-carbonyl]piperidin-4-yl]methylsulfonyl]-3-fluorobenzenesulfonamide 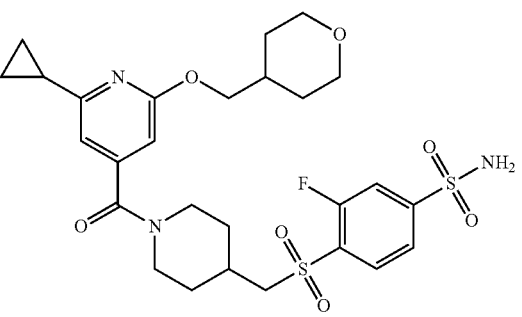 | tert-butyl 4-[(2-fluoro-4-sulfamoylphenyl)sulfonylmethyl]-piperidine-1-carboxylate (intermediate 11.1)/2-cyclopropyl-6-(oxan-4-ylmethoxy)pyridine-4-carboxylic acid (CAS-RN 1810776-23-8) | 596.3 (M + H)+ |
| 6.23 | 4-[1-(6-cyclobutyloxy-5-cyclopropylpyridine-3-carbonyl)piperidin-4-yl]sulfonyl-3-fluorobenzenesulfonamide 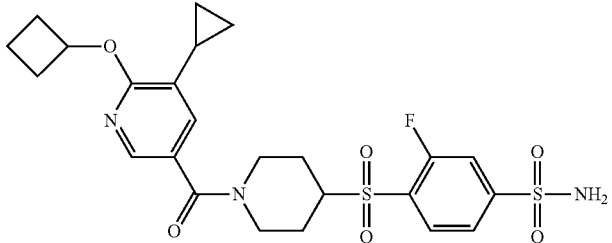 | tert-butyl 4-(2-fluoro-4-sulfamoylphenyl)sulfonylpiperidine-1-carboxylate (intermediate 11)/6-cyclobutyloxy-5-cyclopropylpyridine-3-carboxylic acid (intermediate 17) | 536.0 (M − H)− |
| 6.24 | 4-[1-[2-cyclopropyl-6-(oxan-4-ylmethoxy)pyridine-4-carbonyl]azetidin-3-yl]sulfanyl-3-fluorobenzenesulfonamide 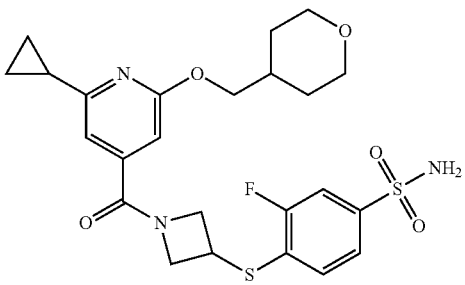 | tert-butyl 3-(2-fluoro-4-sulfamoylphenyl)sulfanylazetidine-1-carboxylate (intermediate 9.3)/2-cyclopropyl-6-(oxan-4-ylmethoxy)pyridine-4-carboxylic acid (CAS-RN 1810776-23-8 | 520.5 (M − H)− |

-continued

| Ex. | Systematic Name | Carbamate/Carboxylic acid | MS, m/e |
|---|---|---|---|
| 6.25 | 4-[1-[2-cyclopropyl-6-(oxan-4-ylmethoxy)pyridine-4-carbonyl]azetidin-3-yl]sulfinyl-3-fluorobenzenesulfonamide 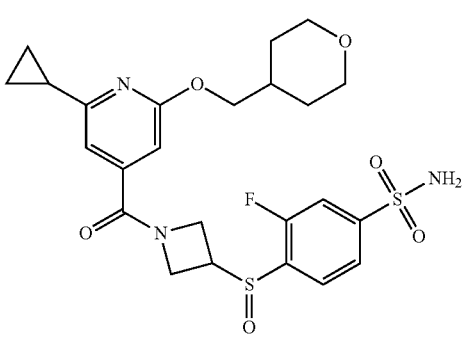 | tert-butyl 3-(2-fluoro-4-sulfamoylphenyl)sulfinylazetidine-1-carboxylate (intermediate 10.3)/ 2-cyclopropyl-6-(oxan-4-ylmethoxy)pyridine-4-carboxylic acid (CAS-RN 1810776-23-8) | 536.2 (M − H)⁻ |
| 6.26 | 4-[1-[2-cyclopropyl-6-(oxan-4-ylmethoxy)pyridine-4-carbonyl]azetidin-3-yl]sulfonyl-3-fluorobenzenesulfonamide 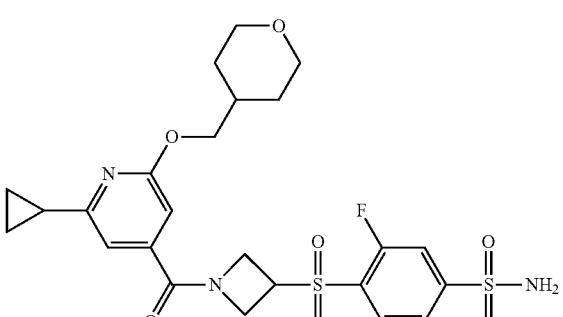 | tert-butyl 3-(2-fluoro-4-sulfamoylphenyl)sulfonylazetidine-1-carboxylate (intermediate 15.1)/ 2-cyclopropyl-6-(oxan-4-ylmethoxy)pyridine-4-carboxylic acid (CAS-RN 1810776-23-8) | 553.3 (M − H)⁻ |
| 6.27 | 4-[1-[2-cyclopropyl-6-(oxan-4-ylmethoxy)pyridine-4-carbonyl]piperidin-4-yl]sulfonyl-2,3-difluorobenzenesulfonamide 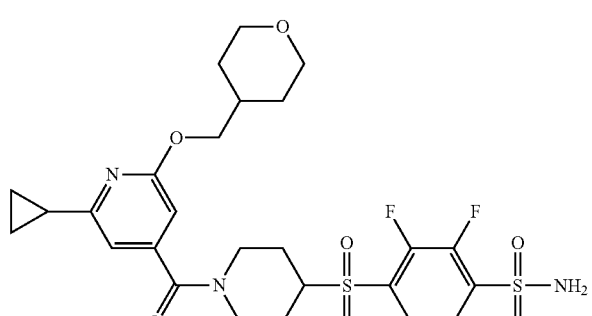 | tert-butyl 4-(2,3-difluoro-4-sulfamoylphenyl)sulfonylpiperidine-1-carboxylate (intermediate 15)/2-cyclopropyl-6-(oxan-4-ylmethoxy)pyridine-4-carboxylic acid (CAS-RN 1810776-23-8) | 600.2 (M + H)⁺ |

-continued

| Ex. | Systematic Name | Carbamate/Carboxylic acid | MS, m/e |
|---|---|---|---|
| 6.28 | 4-[1-[2-cyclopropyl-6-(oxan-4-ylmethoxy)pyridine-4-carbonyl]piperidin-4-yl]sulfonyl-3-fluorobenzenesulfonamide 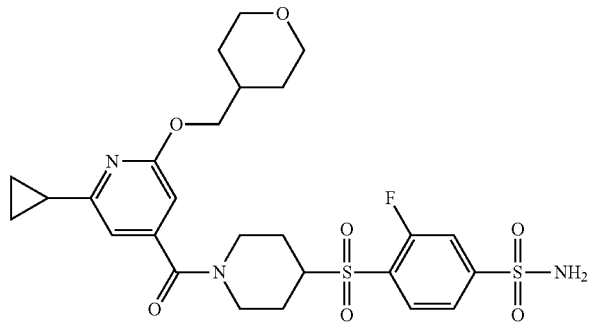 | tert-butyl 4-(2-fluoro-4-sulfamoylphenyl)sulfonylpiperidine-1-carboxylate (intermediate 11)/2-cyclopropyl-6-(oxan-4-ylmethoxy)pyridine-4-carboxylic acid (CAS-RN 1810776-23-8) | 582.2 (M + H)+ |
| 6.29 | 4-[1-[3-[4-chloro-2-[(5-methyltetrazol-2-yl)methyl]phenyl]propanoyl]-piperidin-4-yl]sulfonyl-3-fluorobenzenesulfonamide 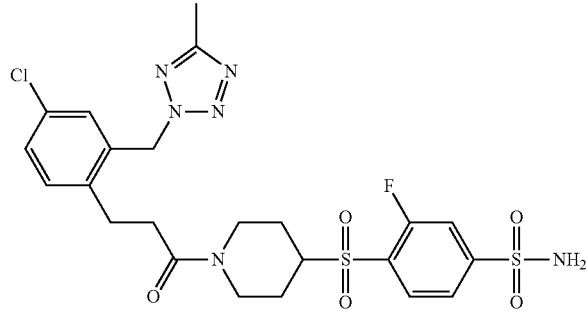 | tert-butyl 4-(2-fluoro-4-sulfamoylphenyl)sulfonylpiperidine-1-carboxylate (intermediate 11)/3-[4-chloro-2-[(5-methyltetrazol-2-yl)methyl]phenyl]propanoic acid (intermediate 13.1) | 585.2 (M + H)+ |
| 6.30 | 4-[1-[3-[4-cyano-2-[(5-methyltetrazol-2-yl)methyl]phenyl]propanoyl]piperidin-4-yl]sulfonyl-3-fluorobenzenesulfonamide 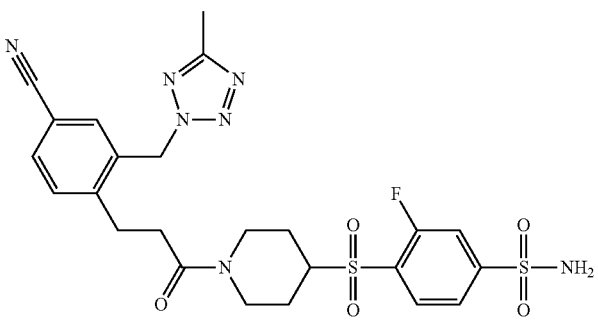 | tert-butyl 4-(2-fluoro-4-sulfamoylphenyl)sulfonylpiperidine-1-carboxylate (intermediate 11)/3-[4-cyano-2-[(5-methyltetrazol-2-yl)methyl]phenyl]propanoic acid (intermediate 13) | 576.3 (M + H)+ |

-continued

| Ex. | Systematic Name | Carbamate/Carboxylic acid | MS, m/e |
|---|---|---|---|
| 6.31 | 4-[2-[1-[2-cyclopropyl-6-(oxan-4-ylmethoxy)pyridine-4-carbonyl]piperidin-4-yl]ethylsulfanyl]-3-fluorobenzenesulfonamide | tert-butyl 4-[2-(2-fluoro-4-sulfamoylphenyl)sulfanylethyl]-piperidine-1-carboxylate (intermediate 9.4)/2-cyclopropyl-6-(oxan-4-ylmethoxy)pyridine-4-carboxylic acid (CAS-RN 1810776-23-8) | 576.4 (M − H)− |

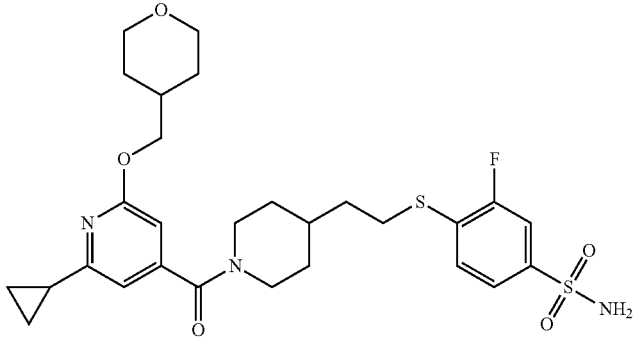

| 6.32 | 4-[2-[1-[2-cyclopropyl-6-(oxan-4-ylmethoxy)pyridine-4-carbonyl]piperidin-4-yl]ethylsulfinyl]-3-fluorobenzenesulfonamide | tert-butyl 4-[2-(2-fluoro-4-sulfamoylphenyl)sulfinylethyl]piper-idine-1-carboxylate (intermediate 10.4)/2-cyclopropyl-6-(oxan-4-ylmethoxy)pyridine-4-carboxylic acid (CAS-RN 1810776-23-8) | 594.2 (M + H)+ |

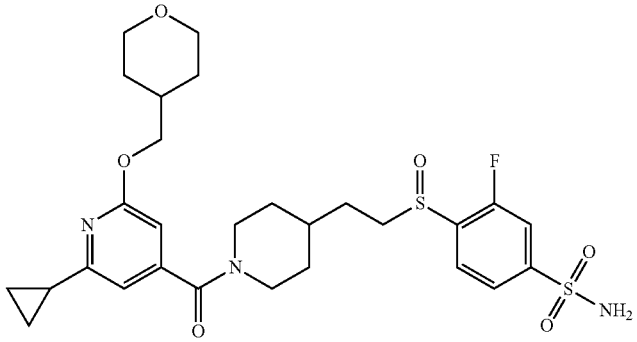

| 6.33 | 4-[2-[1-[2-cyclopropyl-6-(oxan-4-ylmethoxy)pyridine-4-carbonyl]piperidin-4-yl]ethylsulfonyl]-3-fluorobenzenesulfonamide | tert-butyl 4-[2-(2-fluoro-4-sulfamoylphenyl)sulfonylethyl]-piperidine-1-carboxylate (intermediate 16)/2-cyclopropyl-6-(oxan-4-ylmethoxy)pyridine-4-carboxylic acid (CAS-RN 1810776-23-8) | 610.3 (M + H)+ |

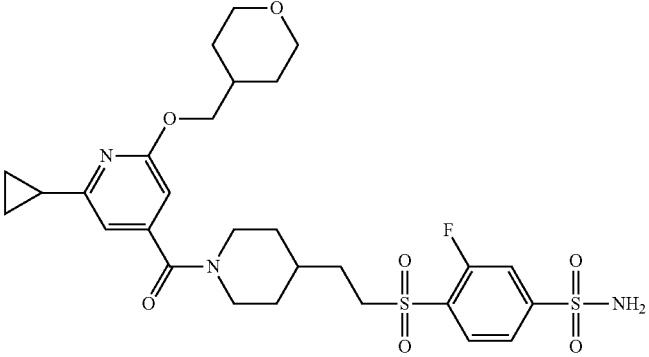

-continued

| Ex. | Systematic Name | Carbamate/Carboxylic acid | MS, m/e |
|---|---|---|---|
| 6.34 | 4-[2-[1-[5-cyclopropyl-6-(cyclopropylmethoxy)pyridine-3-carbonyl]piperidin-4-yl]ethylsulfonyl]-3-fluorobenzenesulfonamide | tert-butyl 4-[2-(2-fluoro-4-sulfamoylphenyl)sulfonylethyl]-piperidine-1-carboxylate (intermediate 16)/5-cyclopropyl-6-(cyclopropylmethoxy)pyridine-3-carboxylic acid (CAS-RN 1427064-97-8) | 566.2 (M + H)+ |
| 6.35 | 4-[4-[2-cyclopropyl-6-(oxan-4-ylmethoxy)pyridine-4-carbonyl]piperazin-1-yl]sulfonyl-3-fluorobenzenesulfonamide | tert-butyl 4-(2-fluoro-4-sulfamoylphenyl)sulfonylpiperazine-1-carboxylate (intermediate 4.1)/ 2-cyclopropyl-6-(oxan-4-ylmethoxy)pyridine-4-carboxylic acid (CAS-RN 1810776-23-8) | 583.3 (M + H)+ |
| 6.36 | 4-[4-[3-[2-[(5-methyltetrazol-2-yl)methyl]-4-(trifluoromethyl)phenyl]-propanoyl]piperazin-1-yl]sulfonylbenzenesulfonamide | tert-butyl 4-(4-sulfamoylphenyl)sulfonylpiperazine-1-carboyxlate (intermediate 4)/3-[2-[(5-methyltetrazol-2-yl)methyl]-4-(trifluoromethyl)phenyl]propanoic acid (CAS-RN 1646783-83-6) | 602.3 (M + H)+ |

| Ex. | Systematic Name | Carbamate/Carboxylic acid | MS, m/e |
|---|---|---|---|
| 6.37 | 5-[1-[3-[2-[(5-methyltetrazol-2-yl)methyl]-4-(trifluoromethyl)phenyl]propanoyl]-piperidin-4-yl]sulfanylthiophene-2-sulfonamide 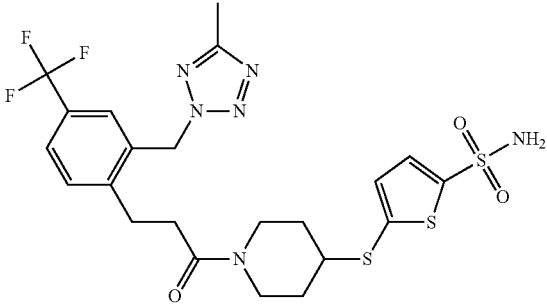 | tert-butyl 4-[(5-sulfamoyl-1,3-thiazol-2-yl)sulfamoyl]piperidine-1-carboxylate (intermediate 9.5)/3-[2-[(5-methyltetrazol-2-yl)methyl]-4-(trifluoromethyl)phenyl]propanoic acid (CAS-RN 1646783-83-6) | 575.1 (M + H)+ |
| 6.38 | 5-[2-[1-[3-[2-[(5-methyltetrazol-2-yl)methyl]-4-(trifluoromethyl)phenyl]-propanoyl]piperidin-4-yl]ethylsulfonyl]thiophene-2-sulfonamide 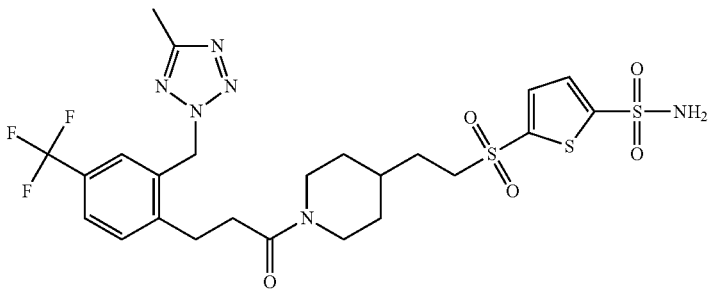 | tert-butyl 4-[2-(5-sulfamoylthiophen-2-yl)sulfonylethyl]piperidine-1-carboxylate (intermediate 15.4)/3-[2-[(5-methyltetrazol-2-yl)methyl]-4-(trifluoromethyl)phenyl]propanoic acid (CAS-RN 1646783-83-6) | 635.2 (M + H)+ |
| 6.39 | 5-fluoro-6-[1-[3-[2-[(5-methyltetrazol-2-yl)methyl]-4-(trifluoromethyl)phenyl]propanoyl]-piperidin-4-yl]sulfanylpyridine-3-sulfonamide 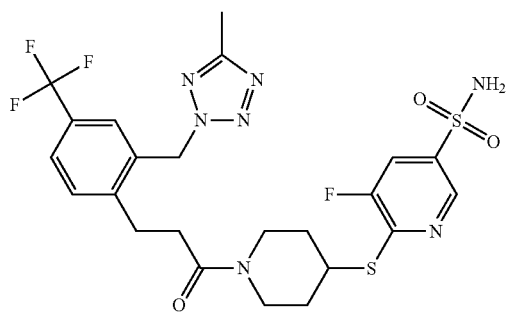 | tert-butyl 4-(3-fluoro-5-sulfamoylpyridin-2-yl)sulfanylpiperidine-1-carboxylate (intermediate 9.1)/3-[2-[(5-methyltetrazol-2-yl)methyl]-4-(trifluoromethyl)phenyl]propanoic acid (CAS-RN 1646783-83-6) | 588.2 (M + H)+ |

-continued

| Ex. | Systematic Name | Carbamate/Carboxylic acid | MS, m/e |
|---|---|---|---|
| 6.40 | 6-[1-[2-cyclopropyl-6-(oxan-4-ylmethoxy)pyridine-4-carbonyl]piperidin-4-yl]sulfanyl-5-fluoropyridine-3-sulfonamide | tert-butyl 4-(3-fluoro-5-sulfamoylpyridin-2-yl)sulfanylpiperidine-1-carboxylate (intermediate 9.1)/2-cyclopropyl-6-(oxan-4-ylmethoxy)pyridine-4-carboxylic acid (CAS-RN 1810776-23-8) | 551.2 (M + H)+ |
| 6.41 | 4-[1-[3-[4-(difluoromethoxy)-2-[(5-methyltetrazol-2-yl)methyl]phenyl]propanoyl]piperidin-4-yl]sulfonyl-3-fluorobenzenesulfonamide | tert-butyl 4-(2-fluoro-4-sulfamoylphenyl)sulfonylpiperidine-1-carboxylate (intermediate 11)/3-[4-(difluoromethoxy)-2-[(5-methyltetrazol-2-yl)methyl]phenyl]propanoic acid (intermediate 13.2) | 617.2 (M + H)+ |
| 6.42 | 4-[2-[1-[3-[4-(difluoromethoxy)-2-[(5-methyltetrazol-2-yl)methyl]phenyl]propanoyl]piperidin-4-yl]ethylsulfinyl]-2,3-difluorobenzenesulfonamide | tert-butyl 4-[2-(2,3-difluoro-4-sulfamoylphenyl)sulfinylethyl]-piperidine-1-carboxylate (intermediate 10.6)/3-[4-(difluoromethoxy)-2-[(5-methyltetrazol-2-yl)methyl]phenyl]propanoic acid (intermediate 13.2) | 647.3 (M + H)+ |

-continued

| Ex. | Systematic Name | Carbamate/Carboxylic acid | MS, m/e |
|---|---|---|---|
| 6.43 | 2,3-difluoro-4-[2-[1-[3-[2-[(5-methyltetrazol-2-yl)methyl]-4-(trifluoromethyl)phenyl]propanoyl]-piperidin-4-yl]ethylsulfinyl]benzenesulfonamide | tert-butyl 4-[2-(2,3-difluoro-4-sulfamoylphenyl)sulfinylethyl]-piperidine-1-carboxylate (intermediate 10.6)/3-[2-[(5-methyltetrazol-2-yl)methyl]-4-(trifluoromethyl)phenyl]propanoic acid (CAS-RN 1646783-83-6) | 649.3 (M + H)+ |
| | 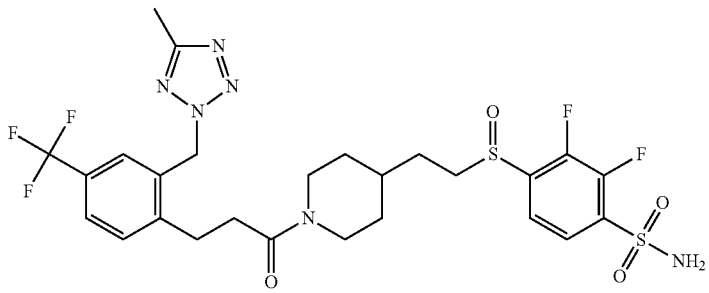 | | |
| 6.44 | 2-[2-[1-[3-[4-(difluoromethoxy)-2-[(5-methyltetrazol-2-yl)methyl]phenyl]-propanoyl]piperidin-4-yl]ethylsulfinyl]-1,3-thiazole-5-sulfonamide | tert-butyl 4-[2-[(5-sulfamoyl-1,3-thiazol-2-yl)sulfinyl]ethyl]piperidine-1-carboxylate (intermediate 10.5)/3-[4-(difluoromethoxy)-2-[(5-methyltetrazol-2-yl)methyl]phenyl]propanoic acid (intermediate 13.2) | 618.2 (M + H)+ |
| | 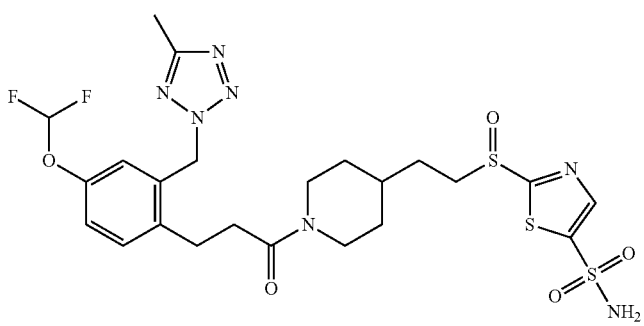 | | |
| 6.45 | 2-[2-[1-[3-[2-[(5-methyltetrazol-2-yl)methyl]-4-(trifluoromethyl)phenyl]propanoyl]piperidin-4-yl]ethylsulfonyl]-1,3-thiazole-5-sulfonamide | tert-butyl 4-[2-[(5-sulfamoyl-1,3-thiazol-2-yl)sulfonyl]ethyl]piperidine-1-carboxylate (intermediate 11.2)/3-[2-[(5-methyltetrazol-2-yl)methyl]-4-(trifluoromethyl)phenyl]propanoic acid (CAS-RN 1646783-83-6) | |
| | 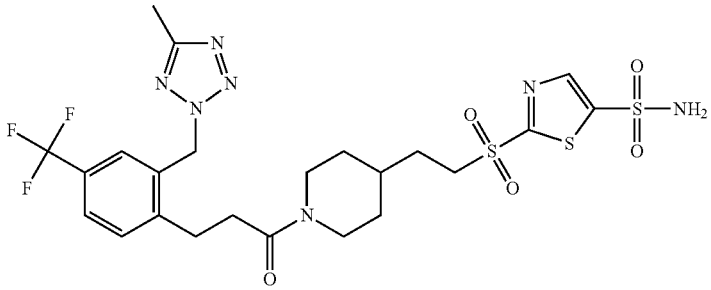 | | |

Example 7 and 8

3-Fluoro-4-[1-[3-[2-[(5-methyltetrazol-2-yl)methyl]-4-(trifluoromethyl)phenyl]propanoyl]piperidin-4-yl]sulfinylbenzenesulfonamide Enantiomer 1 and Enantiomer 2

Racemic 3-fluoro-4-[1-[3-[2-[(5-methyltetrazol-2-yl)methyl]-4-(trifluoromethyl)phenyl]propanoyl]piperidin-4-yl]sulfinylbenzenesulfonamide (example 6.13; 40 mg, 66.4 µmol) was separated by preparative HPLC using a Reprosil Chiral-NR column as the stationary phase and heptane/ethanol 3:2 as the mobile phase. This produced the faster eluting (+)-enantiomer 1 (example 7; 17 mg, 43%; white gum, MS: 601.3 (M−H)⁻) and the slower eluting (−)-enantiomer 2 (example 8; 14 mg, 35%; white solid, MS: 601.4 (M−H)⁻).

The following examples were produced in analogy to examples 7 and 8 by chiral HPLC separation of their racemates.

| Ex. | Starting material (racemic) | Optical rotation sign | Stationary phase; eluent | MS, m/e |
|---|---|---|---|---|
| 7.01 | 4-[[1-[3-[2-[(5-methyltetrazol-2-yl)methyl]-4-(trifluoromethyl)phenyl]propanoyl]pyrrolidin-2-yl]methoxy]benzenesulfonamide (example 5.05) | (+) (faster eluting enantiomer) | Reprosil Chiral-NR; heptane/ethanol 3:2 | 553.3 (M + H)⁺ |
| 8.01 | | (−) (slower eluting enantiomer) | | 553.3 (M + H)⁺ |
| 7.02 | 4-[[1-[3-[2-[(5-methyltetrazol-2-yl)methyl]-4-(trifluoromethyl)phenyl]propanoyl]pyrrolidin-3-yl]methoxy]benzenesulfonamide (example 5.06) | (+) | Reprosil Chiral-NR; heptane/ethanol 3:2 | 553.3 (M + H)⁺ |
| 8.02 | | (−) | | 553.4 (M + H)⁺ |

Example 9

4-[[4-[3-[2-[(5-Methyltetrazol-2-yl)methyl]-4-(trifluoromethyl)phenyl]propanoyl]piperazin-1-yl]methyl]benzenesulfonamide

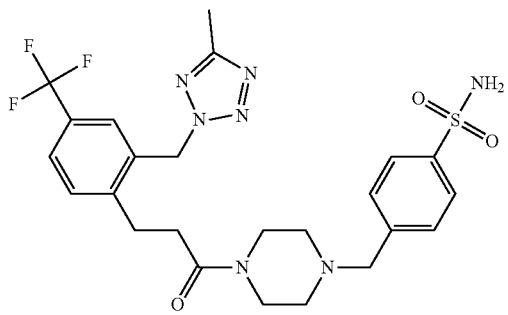 [SMILES: Cc1nnn(Cc2cc(C(F)(F)F)ccc2CCC(=O)N2CCN(Cc3ccc(S(N)(=O)=O)cc3)CC2)n1]

To a solution of 3-[2-[(5-methyltetrazol-2-yl)methyl]-4-(trifluoromethyl)phenyl]-1-piperazin-1-ylpropan-1-one (intermediate 2; 40 mg, 105 µmol) in dichloromethane (2 mL) were added 4-formylbenzenesulfonamide (CAS-RN 3240-35-5; 23.2 mg, 126 µmol), sodium triacetoxyborohydride (28.8 mg, 136 µmol) and acetic acid (12.6 mg, 209 µmol) at room temperature. The mixture was stirred at room temperature for 16 h and then at 50° C. for 24 h, then the reaction mixture was partitioned between sat. aq. sodium hydrogencarbonate solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (6 mg, 10%). White solid, MS: 552.2 (M+H)⁺.

INTERMEDIATES

Intermediate 1

[2-[(5-Methyltetrazol-2-yl)methyl]-4-(trifluoromethyl)phenyl]methanol

Step 1: Ethyl 2-[(5-methyltetrazol-2-yl)methyl]-4-(trifluoromethyl)benzoate

To a solution of 2-[[2-bromo-5-(trifluoromethyl)phenyl]methyl]-5-methyltetrazole (CAS-RN 1646389-14-1; 209 mg, 651 µmol) min ethanol (3 mL) were added 1,1-bis(diphenylphosphino)ferrocenedichloropalladium(I) (CAS-RN 95464-05-4; 21.3 mg, 26 mol), triethylamine (98.8 mg, 976 µmol) and put into a carbon monoxide atmosphere. The reaction mixture was stirred for 18 h under a carbon monoxide atmosphere (70 bar) at 110° C. The reaction mixture was filtered and directly evaporated. Chromatography (silica gel, gradient heptane pure to heptane:ethyl acetate=2:1) produced the title compound (186 mg, 91%), Colourless oil, MS: 315.1 (M+H)⁺.

Step 2: [2-[(5-Methyltetrazol-2-yl)methyl]-4-(trifluoromethyl)phenyl]methanol

To a light yellow solution of ethyl 2-[(5-methyltetrazol-2-yl)methyl]-4-(trifluoromethyl)benzoate (182 mg, 579 µmol) in tetrahydrofuran (5 mL) was added a solution of calcium chloride (129 mg, 1.16 mmol) in ethanol (5 mL). Sodium borohydride (CAS-RN 16940-66-2; 65.7 mg, 1.74 mmol) was added in 3 portions over a period of 30 min to get a white suspension. After 3 h at room temperature the reaction mixture was partitioned between sat. aq. ammonium chloride solution and ethyl acetate. The organic layer was washed with brine, dried over magnesium sulfate, filtered and evaporate to produce the title compound with a purity of 96% (NMR) (164 mg, quant.). Light yellow oil, MS: 273.1 (M+H)⁺.

Intermediate 2

3-[2-[(5-Methyltetrazol-2-yl)methyl]-4-(trifluoromethyl)phenyl]-1-piperazin-1-ylpropan-1-one Step 1: tert-Butyl 4-[3-[2-[(5-methyltetrazol-2-yl)methyl]-4-(trifluoromethyl)phenyl]propanoyl]piperazine-1-carboxylate To a colourless solution of 3-[2-[(5-methyltetrazol-2-yl)methyl]-4-(trifluoromethyl)phenyl]propanoic acid (101 mg, 309 µmol), 4-methylmorpholine (156 mg, 1.54 mmol) tert-butyl piperazine-1-carboxylate (57.5 mg, 309 µmol) in N,N-dimethylformamide (3 mL) was added O-(7-azabenzotriazol-1-yl)-N,N,N',N'-tetramethyluronium hexafluorophosphate (117 mg, 309 µmol) at room temperature, then after 18 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (149 mg, quant.). Colourless oil, MS: 483.2 (M+H)$^+$.

Step 2: 3-[2-[(5-Methyltetrazol-2-yl)methyl]-4-(trifluoromethyl)phenyl]-1-piperazin-1-ylpropan-1-one To a solution of tert-butyl 4-[3-[2-[(5-methyltetrazol-2-yl)methyl]-4-(trifluoromethyl)phenyl]propanoyl]piperazine-1-carboxylate (140 mg, 290 µmol) in dichloromethane (3 mL) trifluoroacetic acid (496 mg, 4.35 mmol) was added. The reaction mixture was stirred at room temperature for 18 h. The mixture was directly evaporated and the residue was partioned between 2 M aq. sodium hydroxide solution and dichloromethane. The aqueous phase was washed two more times with dichloromethane, then the organic phase was dried over magnesium sulfate, filtered and evaporated to give the title compound (90 mg, 81%). White solid, MS: 383.2 (M+H)$^+$.

Intermediate 3

2,6-Difluoro-4-sulfamoylbenzoic Acid

To a stirring suspension of 3,5-difluoro-4-methyl-benzenesulfonamide (CAS-RN 1239964-24-9; 500 mg, 2.41 mmol) in water (25 mL) at reflux was added portionwise potassium permanganate (1.72 g, 10.9 mmol) over 1 h, then the suspension was filtered and washed with water. The mother liquor was extracted twice with ethyl acetate to separate impurities. The aqueous layer was acidified to pH 1 with conc. hydrochloric acid solution and extracted 3 times with ethyl acetate. The combined organic layers were dried over magnesium sulfate and evaporated to dryness to afford the title compound (356 mg, 62%). Light yellow solid, MS: 235.9 (M−H)$^-$.

Intermediate 4 tert-Butyl 4-(4-sulfamoylphenyl)sulfonylpiperazine-1-carboxylate

To a yellow solution of tert-butyl piperazine-1-carboxylate (CAS-RN 57260-71-6; 50 mg, 263 mol) in pyridine (208 mg, 2.63 mmol) and tetrahydrofuran (1 mL) was added a solution of 4-sulfamoylbenzenesulfonyl chloride (CAS-RN 46249-41-6; 80.7 mg, 316 µmol) in tetrahydrofuran (1 mL) at room temperature. The reaction mixture was stirred at room temperature for 18 h and turned into a white suspension, then partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (64 mg, 60%). White solid, MS: 404.3 (M−H)$^-$.

Intermediate 4.1 tert-Butyl 4-(2-fluoro-4-sulfamoylphenyl)sulfonylpiperazine-1-carboxylate

The title compound was produced in analogy to intermediate 4, replacing 4-sulfamoylbenzenesulfonyl chloride by 2-fluoro-4-sulfamoylbenzenesulfonyl chloride (CAS-RN 52295-72-4). White solid, MS: 422.3 (M−H)$^-$.

Intermediate 5 tert-Butyl 4-(2-fluoro-4-sulfamoylbenzoyl)piperazine-1-carboxylate

To a colourless solution of 2-fluoro-4-sulfamoylbenzoic acid (CAS-RN 714968-42-0; 69.4 mg, 301 µmol) in N,N-dimethylformamide (3 mL) was added 4-methylmorpholine (111 mg, 1.09 mmol), tert-butyl piperazine-1-carboxylate (CAS-RN 57260-71-6; 52 mg, 274 µmol) and O-(7-azabenzotriazol-1-yl)-N,N,N',N'-tetramethyluronium hexafluorophosphate (114 mg, 301 µmol) at room temperature, then after 18 h the reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (107 mg, quant.). White foam, MS: 386.3 (M−H)$^-$.

Intermediate 6

[2-Cyclopropyl-6-(oxan-4-ylmethoxy)pyridin-4-yl]methanol

To a solution of 2-cyclopropyl-6-(oxan-4-ylmethoxy)pyridine-4-carboxylic acid (CAS-RN 1810776-23-8; 300 mg, 1.08 mmol) in tetrahydrofuran (5 mL) was added slowly borane tetrahydrofuran complex solution (CAS-RN 14044-65-6; 1 M in tetrahydrofuran; 2.7 mL, 2.7 mmol) at room temperature. The reaction mixture was stirred at room temperature for 18 h. More borane tetrahydrofuran complex solution (1.62 mL, 1.62 mmol) was added and stirring was continued for 6 h. The reaction was carefully treated with 3 mL methanol, let stir for 10 min at room temperature and then totally evaporated. The residue was partitioned between ethyl acetate and 1 M aq. sodium hydroxide solution. The organic layer was washed with brine, dried over magnesium sulfate, filtered and evaporated to produce the title compound (239 mg, 84%). Colourless oil, MS: 264.3 (M+H)$^+$.

Intermediate 7

4-Fluoro-3-(piperidin-4-ylmethyl)benzenesulfonamide hydrochloride

Step 1: 1-[4-[(2-Fluorophenyl)methyl]-1-piperidyl]ethanone

4-[(2-fluorophenyl)methyl]piperidine hydrochloride (CAS-RN 193357-26-5; 350 mg, 1.48 mmol) was combined with dichloromethane (5 mL) and N-methylmorpholine (149 mg, 162 µl, 1.48 mmol was added, then acetic anhydride (317 mg, 3.1 mmol) was added dropwise at 0° C. under stirring, and the mixture was stirred at room temperature for 1 h. The mixture was directly concentrated in vacuo. The residue was partitioned between ethyl acetate and sat. aq. sodium bicarbonate solution. The organic layer was washed with brine, dried over magnesium sulfate, filtered and evaporated to give the title compound with a purity of approximately 90% (NMR) (388 mg, quant.). Light yellow oil, MS: 236.2 (M+H)$^+$.

Step 2: 3-[(1-Acetyl-4-piperidyl)methyl]-4-fluoro-benzenesulfonamide

A solution of 1-[4-[(2-fluorophenyl)methyl]-1-piperidyl]ethanone (384 mg, 1.47 mmol) in dichloromethane (5 mL) was added dropwise to sulfurochloridic acid (856 mg, 7.34 mmol) at 0° C. under stirring, then stirred at 0° C. for 30 min and at room temperature for 2 h. The reaction mixture was directly evaporated at high vacuum. The residue was combined with tetrahydrofuran (5 mL) and cooled down to 0° C., then 25% aq. ammonia solution (3 mL) was added dropwise. The reaction mixture was stirred at 0° C. for 30 min and then at room temperature for 18 h, then directly evaporated to remove tetrahydrofuran. The aqueous residue was partitioned between ethyl acetate and 1 M aq. hydrochloric acid solution. The organic layer was washed with brine, dried over magnesium sulfate, filtered and evaporated. Chromatography (silica gel, gradient heptane:ethyl acetate=4:1 to 9:1 then ethyl acetate pure and finally gradient ethyl acetate pure to methanol pure) produced the title compound (353 mg, 76%). White foam, MS: 315.2 (M+H)$^+$.

Step 3: 4-Fluoro-3-(piperidin-4-ylmethyl)benzenesulfonamide hydrochloride

3-[(1-acetyl-4-piperidyl)methyl]-4-fluoro-benzenesulfonamide (345 mg, 1.1 mmol) was combined with aq. hydrochloric acid (25% in water; 4.8 g, 32.9 mmol) and stirred at reflux for 6 h. The reaction mixture was directly evaporated and dried at high vacuum to give the title compound with a purity of approximately 95% (NMR) (305 mg, 86%). White foam, MS: 273.2 (M+H)$^+$.

Intermediate 8

3-Fluoro-4-piperidin-4-ylsulfanylbenzenesulfonamide Hydrochloride

Step 1: N'-(4-Bromo-3-fluoro-phenyl)sulfonyl-N,N-dimethyl-formamidine

A solution of 1,1-dimethoxy-N,N-dimethyl-methanamine (CAS-RN 4637-24-5; 170 mg, 1.38 mmol) in acetonitrile (1 mL) was added dropwise at room temperature to a stirring solution of 4-bromo-3-fluorobenzenesulfonamide (CAS-RN 263349-73-1; 302 mg, 1.15 mmol) in acetonitrile (3 mL). After 1 h the mixture was directly evaporated at high vacuum to give the title compound (369 mg, quant.). White solid, MS: 309.0 (M+H)$^+$.

Step 2: 3-Fluoro-4-piperidin-4-ylsulfanylbenzenesulfonamide hydrochloride

A solution of tert-butyl 4-sulfanylpiperidine-1-carboxylate (CAS-RN 134464-79-2; 244 mg, 1.1 mmol) in N,N-dimethylformamide (2 mL) was added dropwise to a stirring mixture of sodium hydride (50% oil dispersion; 52.9 mg, 1.1 mmol) and N,N-dimethylformamide (2 mL). After 30 min at room temperature gas evolution was complete and another solution of N'-(4-bromo-3-fluoro-phenyl)sulfonyl-N,N-dimethyl-formamidine (351 mg, 1.1 mmol) in N,N-dimethylformamide (2 mL) was added dropwise. The reaction mixture was stirred at 60° C. for 3 h and then directly evaporated to remove N,N-dimethylformamide. The residue was combined with methanol (4 mL) and 2.5 M aq. sodium hydroxide solution (4.4 mL, 11 mmol) and then stirred at 100° C. for 1 h. The mixture was directly evaporated again to remove methanol, then hydrochloric acid solution (5 M in isopropanol; 4.4 mL, 22 mmol) was added and stirred at 50° C. for 1.5 h. The white suspension was filtered off, and the mother liquor was evaporated to give the title compound as a mixture of approximately 1:1 (bromide isomer) with a purity of 80% (440 mg, 49%). Off-white foam, MS: 291.1 (M+H)$^+$.

Intermediate 9 tert-Butyl 4-[(2-fluoro-4-sulfamoylphenyl)sulfanylmethyl]piperidine-1-carboxylate

Step 1: N'-(3,4-Difluorophenyl)sulfonyl-N,N-dimethyl-formamidine

The title compound was produced in analogy to intermediate 8, step 1 from 3,4-difluorobenzenesulfonamide (CAS-RN 108966-71-8) and 1,1-dimethoxy-N,N-dimethyl-methanamine (CAS-RN 4637-24-5). White solid, MS: 249.1.0 (M+H)$^+$.

Step 2: tert-Butyl 4-[(2-fluoro-4-sulfamoylphenyl)sulfanylmethyl]piperidine-1-carboxylate N'-(3,4-difluorophenyl)sulfonyl-N,N-dimethyl-formamidine (315 mg, 1.27 mmol) was added to a stirring mixture of sodium hydride (50% oil dispersion; 60.9 mg, 1.27 mmol) and N,N-dimethylformamide (2 mL) at room temperature. 5 min later tert-butyl 4-(sulfanylmethyl)piperidine-1-carboxylate (CAS-RN 581060-27-7; 281 mg, 1.27 mmol) was added. A strong gas evolution and exothermic reaction could be observed. The reaction mixture was stirred at room temperature for 1 h and then directly evaporated to remove N,N-dimethylformamide. The residue was combined with methanol (4 mL) and 2.5 M aq. sodium hydroxide solution (5.08 mL, 12.7 mmol) and the white suspension was stirred at room temperature for 3 h. The mixture was partitioned between ice and 1 M aq. hydrochloric acid solution and ethyl acetate. The organic layer was washed with brine, dried over magnesium sulfate, filtered and evaporated. Chromatography of the residue (silica gel, gradient dichloromethane to dichloromethane/methanol/25% aq. ammonia solution 90:10:0.25) produced the title compound with a purity of approximately 95% (NMR) (463 mg, 89%). Colourless gum, MS: 389.3 (M–H)$^-$.

The following intermediates were prepared according to intermediate 9, replacing tert-butyl 4-(sulfanylmethyl)piperidine-1-carboxylate (CAS-RN 581060-27-7) by the appropriate thiol 3,4-difluorobenzenesulfonamide (CAS-RN 108966-71-8) by the appropriate sulfon amide.

| No. | Systematic Name | Thiol/Sulfonamide | MS, m/e |
|---|---|---|---|
| 9.1 | tert-butyl 4-(3-fluoro-5-sulfamoylpyridin-2-yl)sulfanylpiperidine-1-carboxylate | tert-butyl 4-sulfanylpiperidine-1-carboxylate (CAS-RN 134464-79-2)/ 6-chloro-5-fluoropyridine-3-sulfonamide (CAS-RN 1803571-80-3) | 390.2 (M − H)⁻ |
| 9.2 | tert-butyl 4-(2,3-difluoro-4-sulfamoylphenyl)sulfanylpiperidine-1-carboxylate | tert-butyl 4-sulfanylpiperidine-1-carboxylate (CAS-RN 134464-79-2)/ 2,3,4-trifluorobenzenesulfonamide (CAS-RN 518070-13-8) | 407.2 (M − H)⁻ |
| 9.3 | tert-butyl 3-(2-fluoro-4-sulfamoylphenyl)sulfanylazetidine-1-carboxylate | tert-butyl 3-sulfanylazetidine-1-carboxylate (CAS-RN 941585-25-7)/ 3,4-difluorobenzenesulfonamide (CAS-RN 108966-71-8) | 361.2 (M − H)⁻ |
| 9.4 | tert-butyl 4-[2-(2-fluoro-4-sulfamoylphenyl)sulfanylethyl]piperidine-1-carboxylate | tert-butyl 4-(2-sulfanylethyl)piperidine-1-carboxylate (CAS-RN 1420841-79-7)/3,4-difluorobenzenesulfonamide (CAS-RN 108966-71-8) | 417.3 (M − H)⁻ |
| 9.5 | tert-butyl 4-[(5-sulfamoyl-1,3-thiazol-2-yl)sulfanyl]piperidine-1-carboxylate | tert-butyl 4-sulfanylpiperidine-1-carboxylate (CAS-RN 134464-79-2)/ 2-chloro-1,3-thiazole-5-sulfonamide (CAS-RN 848362-00-5) | 378.2 (M − H)⁻ |
| 9.6 | tert-butyl 4-[2-(2,3-difluoro-4-sulfamoylphenyl)sulfanylethyl]piperidine-1-carboxylate | tert-butyl 4-(2-sulfanylethyl)piperidine-1-carboxylate (CAS-RN 1420841-79-7)/2,3,4-trifluorobenzenesulfonamide (CAS-RN 518070-13-8) | 435.2 (M − H)⁻ |
| 9.7 | tert-butyl 4-[2-[(5-sulfamoyl-1,3-thiazol-2-yl)sulfanyl]ethyl]piperidine-1-carboxylate | tert-butyl 4-(2-sulfanylethyl)piperidine-1-carboxylate (CAS-RN 1420841-79-7)/2-chloro-1,3-thiazole-5-sulfonamide (CAS-RN 848362-00-5) | 406.2 (M − H)⁻ |
| 9.8 | tert-butyl 4-[2-(5-sulfamoylthiophen-2-yl)sulfanylethyl]piperidine-1-carboxylate | tert-butyl 4-(2-sulfanylethyl)piperidine-1-carboxylate (CAS-RN 1420841-79-7)/5-bromothiophene-2-sulfonamide (CAS-RN 53595-65-6) | 405.3 (M − H)⁻ |
| 9.9 | tert-butyl 4-(2-fluoro-4-sulfamoyl-phenyl)sulfanylpiperidine-1-carboxylate | tert-butyl 4-sulfanylpiperidine-1-carboxylate (CAS-RN 134464-79-2)/ 3,4-difluorobenzenesulfonamide (CAS-RN 108966-71-8) | 389.3 (M − H)⁻ |
| 9.10 | tert-butyl 4-(2-((5-sulfamoylthiazol-2-yl)thio)ethyl)piperidine-1-carboxylate | tert-butyl 4-(2-sulfanylethyl)piperidine-1-carboxylate (CAS-RN 1420841-79-7)/2-chloro-1,3-thiazole-5-sulfonamide (CAS-RN 848362-00-5) | 406.2 (M − H)⁻ |

Intermediate 10 tert-Butyl 4-(2-fluoro-4-sulfamoylphenyl)sulfinylpiperidine-1-carboxylate

To a solution of tert-butyl 4-(2-fluoro-4-sulfamoylphenyl)sulfanylpiperidine-1-carboxylate (intermediate 9.9; 459 mg, 1.12 mmol) in glacial acetic acid (2 mL) was added hydrogen peroxide (35% in water; 369 mg, 3.8 mmol). The resulting solution was stirred at room temperature for 4 h. and then partitioned between ice and ethyl acetate. The organic layer was washed with water and brine, dried over magnesium sulfate, filtered and evaporated at high vacuum to give the title compound (428 mg, 94%). White foam, MS: 405.3 (M−H)⁻.

The following intermediates were prepared according to intermediate 10, replacing tert-butyl 4-(2-fluoro-4-sulfamoylphenyl)sulfanylpiperidine-1-carboxylate (intermediate 9.9) by the appropriate thioether.

| No. | Systematic Name | Thioether | MS, m/e |
|---|---|---|---|
| 10.1 | tert-butyl 4-[(2-fluoro-4-sulfamoylphenyl)sulfinylmethyl]piperidine-1-carboxylate | tert-butyl 4-[(2-fluoro-4-sulfamoylphenyl)sulfanylmethyl]piperidine-1-carboxylate (intermediate 9) | 419.3 (M − H)⁻ |
| 10.2 | tert-butyl 4-(2,3-difluoro-4-sulfamoylphenyl)sulfinylpiperidine-1-carboxylate | tert-butyl 4-(2,3-difluoro-4-sulfamoylphenyl)sulfanylpiperidine-1-carboxylate (intermediate 9.2) | 423.2 (M − H)⁻ |
| 10.3 | tert-butyl 3-(2-fluoro-4-sulfamoylphenyl)sulfinylazetidine-1-carboxylate | tert-butyl 3-(2-fluoro-4-sulfamoylphenyl)sulfanylazetidine-1-carboxylate (intermediate 9.3) | 377.3 (M − H)⁻ |
| 10.4 | tert-butyl 4-[2-(2-fluoro-4-sulfamoylphenyl)sulfinylethyl]piperidine-1-carboxylate | tert-butyl 4-[2-(2-fluoro-4-sulfamoylphenyl)sulfanylethyl]piperidine-1-carboxylate (intermediate 9.4) | 433.3 (M − H)⁻ |
| 10.5 | tert-butyl 4-[2-[(5-sulfamoyl-1,3-thiazol-2-yl)sulfinyl]ethyl]piperidine-1-carboxylate | tert-butyl 4-[2-[(5-sulfamoyl-1,3-thiazol-2-yl)sulfanyl]ethyl]piperidine-1-carboxylate (intermediate 9.7) | 422.2 (M − H)⁻ |

-continued

| No. | Systematic Name | Thioether | MS, m/e |
|---|---|---|---|
| 10.6 | tert-butyl 4-[2-(2,3-difluoro-4-sulfamoylphenyl)sulfinylethyl]piperidine-1-carboxylate | tert-butyl 4-[2-(2,3-difluoro-4-sulfamoylphenyl)sulfanylethyl]piperidine-1-carboxylate (intermediate 9.6) | 451.2 (M − H)⁻ |
| 10.7 | tert-butyl 4-(2((5-sulfamoylthiazol-2-yl)sulfinyl)ethyl)piperidine-1-carboxylate | tert-butyl 4-(2-((5-sulfamoylthiazol-2-yl)thio)ethyl)piperidine-1-carboxylate | 422.2 (M − H)⁻ |

Intermediate 11 tert-Butyl 4-(2-fluoro-4-sulfamoylphenyl)sulfonylpiperidine-1-carboxylate

To a colourless solution of tert-butyl 4-(2-fluoro-4-sulfamoylphenyl)sulfinylpiperidine-1-carboxylate (intermediate 10; 374 mg, 920 µmol) in dichloromethane (4 mL) was added 3-chlorobenzenecarboperoxoic acid (CAS-RN 937-14-4; 318 mg, 1.84 mmol) at room temperature. The reaction mixture was stirred at room temperature for 18 h and then partitioned between ice and 1 M aq. sodium carbonate solution and ethyl acetate. The organic layer was washed with brine, dried over magnesium sulfate, filtered and evaporated to give the title compound with e purity of approximately 90% (NMR).

This material was precipitated from 2 mL of dichloromethane (286 mg, 74%). White solid, MS: 421.3 (M−H)⁻.

The following intermediates were produced according to intermediate 11, replacing tert-butyl 4-(2-fluoro-4-sulfamoylphenyl)sulfinylpiperidine-1-carboxylate by the appropriate sulfoxide.

| No. | Systematic Name | Sulfoxide | MS, m/e |
|---|---|---|---|
| 11.1 | tert-butyl 4-[(2-fluoro-4-sulfamoylphenyl)-sulfonylmethyl]piperidine-1-carboxylate | tert-butyl 4-[(2-fluoro-4-sulfamoylphenyl)-sulfinylmethyl]piperidine-1-carboxylate (intermediate 10.1) | 435.3 (M − H)⁻ |
| 11.2 | tert-butyl 4-[2-[(5-sulfamoyl-1,3-thiazol-2-yl)sulfonyl]ethyl]piperidine-1-carboxylate | tert-butyl 4-(2-((5-sulfamoylthiazol-2-yl)sulfinyl)ethyl)piperidine-1-carboxylate (intermediate 10.7) | 438.2 (M − H)⁻ |

Intermediate 12

N-[5-Cyano-2-(hydroxymethyl)pyridin-3-yl]-2,2-dimethylpropanamide

Step 1: Methyl 5-bromo-3-(2,2-dimethylpropanoylamino)pyridine-2-carboxylate

To a light yellow suspension of methyl 3-amino-5-bromopyridine-2-carboxylate (CAS-RN 1072448-08-8; 900 mg, 3.7 mmol) in pyridine (15 mL) was added 2,2-dimethylpropanoyl chloride (CAS-RN 3282-30-2; 546 mg, 4.44 mmol). The colour turned to light red. More 2,2-dimethylpropanoyl chloride (1.092 g, 8.88 mmol) was added and the reaction was stirred at room temperature for 18 h, then partitioned between ice and 1 M aq. hydrochloric acid solution and ethyl acetate. The organic layer was washed with brine, dried over magnesium sulfate, filtered and evaporated. Chromatography (silica gel, gradient dichloromethane/heptane 1:1 to dichloromethane) produced the title compound (385 mg, 99%). White solid, MS: 317.0 (M+H)⁺.

Step 2: Methyl 5-cyano-3-(2,2-dimethylpropanoylamino)pyridine-2-carboxylate

To a microwave vial containing a solution of methyl 5-bromo-3-(2,2-dimethylpropanoylamino)pyridine-2-carboxylate (1.13 g, 3.59 mmol) in N,N-dimethylformamide (14.9 mL) and water (119 µl) was added Tris(dibenzylideneacetone)dipalladium (CAS-RN 51364-51-3; 32.8 mg, 35.9 µmol), 1,1'-bis(diphenylphosphino)ferrocene (CAS-RN 12150-46-8; 59.6 mg, 108 µmol), zinc cyanide (CAS-RN 557-21-1; 232 mg, 1.97 mmol), zinc (CAS-RN 7440-66-6; 9.38 mg, 143 µmol) and zinc acetate (CAS-RN 557-34-6; 26.3 mg, 143 µmol). The vial was capped and heated in the microwave at 140° C. for 30 min. The reaction mixture was filtered and the mother liquor was evaporated. The residue was diluted with 50% aq. sodium hydrogencarbonate solution and extracted with ethyl acetate. The organic layer was washed with water and brine, dried over magnesium sulfate, filtered and evaporated. Chromatography (silica gel, gradient dichloromethane to dichloromethane/methanol 50:1) produced the title compound (468 mg, 50%). Yellow solid, MS: 262.2 (M+H)⁺.

Step 3: N-[5-Cyano-2-(hydroxymethyl)pyridin-3-yl]-2,2-dimethylpropanamide

To a clear yellow solution of methyl 5-cyano-3-(2,2-dimethylpropanoylamino)pyridine-2-carboxylate (453 mg, 1.73 mmol) in tetrahydrofuran (5 mL) and ethanol (5 mL) was added sodium borohydride (262 mg, 6.94 mmol) in 3 portions over a period of 30 min. The reaction mixture was partitioned between sat. aq. ammonium chloride solution and ethyl acetate. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (378 mg, 94%). Light yellow viscous oil, MS: 234.2 (M+H)⁺.

Intermediate 13

3-[4-Cyano-2-[(5-methyltetrazol-2-yl)methyl]phenyl]propanoic Acid

Step 1: Ethyl (E)-3-[4-cyano-2-[(5-methyltetrazol-2-yl)methyl]phenyl]prop-2-enoate To a colourless solution of 4-bromo-3-[(5-methyltetrazol-2-yl)methyl]benzonitrile (CAS-RN 1646784-84-0; 450 mg, 1.62 mmol) in N,N-dimethylformamide (6 mL) was added ethyl acrylate (194 mg, 1.94 mmol), triethylamine (491 mg, 4.85 mmol), palladium(II) acetate (7.27 mg, 32.4 µmol) and tri-O-tolylphosphine (39.4 mg, 129 µmol). The reaction was aerated with argon and stirred at 120° C. for 18 h, then partitioned between sat. aq. ammonium chloride solution and dichloromethane. The organic layer was washed with brine, dried over magnesium sulfate, filtered and evaporated. Chromatography (silica gel, gradient dichloromethane to dichloromethane/methanol/25% aq. ammonia solution 90:10:0.25) produced the title compound (431 mg, 90%). Light brown solid. MS: 296.2 (M+H)$^+$.

Step 2: Ethyl 3-[4-cyano-2-[(5-methyltetrazol-2-yl)methyl]phenyl]propanoate To a light brown suspension of ethyl (E)-3-[4-cyano-2-[(5-methyltetrazol-2-yl)methyl]phenyl]prop-2-enoate (431 mg, 1.45 mmol) in methanol (6 mL) was added palladium (CAS-RN 7440-05-3; 89.4 mg, 840 µmol) and an atmosphere of hydrogen was introduced. After 17 h at room temperature the reaction was aerated with argon, filtered over diatomaceous filter-aid and rinsed with methanol. The mother liquor was totally evaporated to afforded the crude title product (286 mg, 66%). Grey viscous oil, MS: 300.2 (M+H)$^+$.

Step 3: 3-[4-Cyano-2-[(5-methyltetrazol-2-yl)methyl]phenyl]propanoic Acid

To a colourless solution of ethyl 3-[4-cyano-2-[(5-methyltetrazol-2-yl)methyl]phenyl]propanoate (79.1 mg, 264 µmol) in tetrahydrofuran (1 mL) and ethanol (0.5 mL) was added a 1 M aq. lithium hydroxide monohydrate solution (CAS-RN 1310-66-3; 793 µl, 793 µmol). The reaction was stirred at room temperature for 4 h, then poured onto ice and acidified with 2 M aq. hydrochloric acid solution to pH 1. The aqueous phase was extracted with ethyl acetate, then the organic phase was washed with brine, dried over magnesium sulfate, filtered and evaporated to produce the title compound (66 mg, 92%). White solid. MS: 270.3 (M−H)$^-$.

The following intermediates were prepared according to intermediate 13, replacing 4-bromo-3-[(5-methyltetrazol-2-yl)methyl]benzonitrile by the appropriate starting material.

Intermediate 14

[5-Chloro-3-[(5-methyltetrazol-2-yl)methyl]pyridin-2-yl]methanol

Step 1: Methyl 5-chloro-3-[(5-methyltetrazol-2-yl)methyl]pyridine-2-carboxylate methyl 3-(bromomethyl)-5-chloropyridine-2-carboxylate (CAS-RN 1260667-62-6; 500 mg, 1.51 mmol) was dissolved in acetone (10 mL) and potassium carbonate (209 mg, 1.51 mmol) and 5-methyl-2H-tetrazole (CAS-RN 4076-36-2; 130 mg, 1.51 mmol) were added at room temperature. The resulting suspension was stirred for 2 h at reflux (60° C.) and then partitioned between ice-water and ethyl acetate. The organic layer was washed with brine, dried over magnesium sulfate, filtered and evaporated. Chromatography (silica gel, gradient heptane pure to heptane:ethyl acetate=2:1) produced the title compound (185 mg, 46%). White solid, MS: 268.1 (M+H)+.

Step 2: [5-Chloro-3-[(5-methyltetrazol-2-yl)methyl]pyridin-2-yl]methanol

The title compound was produced in analogy to intermediate 1, step 2 replacing ethyl 2-[(5-methyltetrazol-2-yl)methyl]-4-(trifluoromethyl)benzoate by methyl 5-chloro-3-[(5-methyltetrazol-2-yl)methyl]pyridine-2-carboxylate. Off-white semisolid, MS: 240.1 (M+H)$^+$.

Intermediate 15 tert-Butyl 4-(2,3-difluoro-4-sulfamoylphenyl)sulfonylpiperidine-1-carboxylate To a solution of tert-butyl 4-(2,3-difluoro-4-sulfamoylphenyl)sulfanylpiperidine-1-carboxylate (intermediate 9.2; 94 mg, 230 µmol) in glacial acetic acid (3 mL) was added hydrogen peroxide (35% in water; 76 mg, 782 µmol). The resulting solution was stirred at room temperature for 96 h and then partitioned between ice and ethyl acetate. The organic layer was washed with water and brine, dried over magnesium sulfate, filtered and evaporated. Chromatography (silica gel, gradient heptane pure to heptane:ethyl acetate=1:2) produced the title compound (94 mg, 74%). White solid, MS: 439.2 (M−H)$^-$.

The following intermediates were prepared according to intermediate 15, replacing tert-butyl 4-(2,3-difluoro-4-sulfamoylphenyl)sulfanylpiperidine-1-carboxylate (intermediate 9.2) by the appropriate thioether.

| No. | Systematic Name | Starting material | MS, m/e |
|---|---|---|---|
| 13.1 | 3-[4-chloro-2-[(5-methyltetrazol-2-yl)methyl]phenyl]propanoic acid | 2-[(2-bromo-5-chlorophenyl)methyl]-5-methyltetrazole (CAS-RN 1646389-12-9) | 279.2 (M − H)$^-$ |
| 13.2 | 3-[4-(difluoromethoxy)-2-[(5-methyltetrazol-2-yl)methyl]phenyl]propanoic acid | 2-[[2-bromo-5-(difluoromethoxy)phenyl]methyl]-5-methyltetrazole (CAS-RN 1646786-22-2) | 313.1 (M + H)$^+$ |

| No. | Systematic Name | Thioether | MS, m/e |
|---|---|---|---|
| 15.1 | tert-butyl 3-(2-fluoro-4-sulfamoylphenyl)sulfonylazetidine-1-carboxylate | tert-butyl 3-(2-fluoro-4-sulfamoylphenyl)sulfanylazetidine-1-carboxylate (intermediate 9.3) | 393.3 (M − H)⁻ |
| 15.2 | tert-butyl 4-[(5-sulfamoyl-1,3-thiazol-2-yl)sulfonyl]piperidine-1-carboxylate | tert-butyl 4-[(5-sulfamoyl-1,3-thiazol-2-yl)sulfanyl]piperidine-1-carboxylate (intermediate 9.5) | 410.1 (M − H)⁻ |
| 15.3 | tert-butyl 4-[2-(2,3-difluoro-4-sulfamoylphenyl)sulfonylethyl]piperidine-1-carboxylate | tert-butyl 4-[2-(2,3-difluoro-4-sulfamoylphenyl)sulfanylethyl]piperidine-1-carboxylate (intermediate 9.6) | 467.2 (M − H)⁻ |
| 15.4 | tert-butyl 4-[2-(5-sulfamoylthiophen-2-yl)sulfonylethyl]piperidine-1-carboxylate | tert-butyl 4-[2-(5-sulfamoylthiophen-2-yl)sulfanylethyl]piperidine-1-carboxylate (intermediate 9.8) | 437.1 (M − H)⁻ |

Intermediate 16 tert-Butyl 4-[2-(2-fluoro-4-sulfamoylphenyl)sulfonylethyl]piperidine-1-carboxylate The title compound was produced in analogy to intermediate 15, replacing tert-butyl 4-(2,3-difluoro-4-sulfamoylphenyl)sulfanylpiperidine-1-carboxylate (intermediate 9.2) by tert-butyl 4-[2-(2-fluoro-4-sulfamoylphenyl)sulfinylethyl]piperidine-1-carboxylate (intermediate 10.4). White solid, MS: 449.3 (M−H)⁻.

Intermediate 17

6-Cyclobutyloxy-5-cyclopropylpyridine-3-carboxylic Acid

To a colourless solution of 5-bromo-6-cyclobutyloxypyridine-3-carboxylic acid (CAS-RN 1364678-46-5; 1 g, 3.68 mmol) in toluene (25 mL) and water (2.8 mL) was added cesium carbonate (3.59 g, 11.0 mmol), palladium(II) acetate (16.5 mg, 73.5 µmol), potassium cyclopropyltrifluoroborate (CAS-RN 1065010-87-8; 598 mg, 4.04 mmol) and butyldi-1-adamantylphosphine (CAS-RN 321921-71-5; 79.1 mg, 221 µmol). The reaction mixture was degassed and aerated with argon three times and then stirred at 120° C. for 16 h. The mixture was partitioned between ice and 1 M aq. sodium hydroxide solution and dichloromethane. The organic layer was washed with brine, dried over magnesium sulfate, filtered and evaporated. Recrystallization from ethyl acetate produced the title compound (610 mg, 71%). Off-white solid, 234.4 (M+H)⁺.

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

What is claimed is:
1. A compound of formula (I):

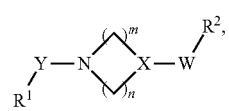

(I)

wherein:
R¹ is selected from
  i) phenyl substituted by R³, R⁴ and R⁵,
  ii) pyridinyl substituted by R³, R⁴ and R⁵, and
  iii) thiophenyl substituted by R³, R⁴ and R⁵;
X is selected from
  i) N, and
  ii) CH;
Y is selected from
  i) —CH₂—OC(O)—,
  ii) —(CH₂)_q C(O)—,
  iii) —(CH═CH)_r —C(O)—, and
  iv) —(CH≡CH)_r —C(O)—;
W is selected from
  i) —(CR⁹R¹⁰)_p —,
  ii) —(CR⁹R¹⁰)_p —C(O)—,
  iii) —(CR⁹R¹⁰)_p —O—,
  iv) —(CR⁹R¹⁰)_p —S—,
  v) —(CR⁹R¹⁰)_p —S(O)—, and
  vi) —(CR⁹R¹⁰)_p —S(O)₂—;
R² is selected from
  i) substituted phenyl, wherein the phenyl ring is substituted by R⁶, R⁷ and R⁸,
  ii) substituted pyridinyl, wherein the pyridinyl ring is substituted by R⁶, R⁷ and R⁸,
  iii) substituted thiophenyl, wherein the thiophenyl ring is substituted by R⁶, R⁷ and R⁸, and
  iv) substituted thiazolyl, wherein the thiazolyl ring is substituted by R⁶, R⁷ and R⁸;
R³ is selected from
  i) halo-C₁₋₆-alkoxy,
  ii) C₃₋₈-cycloalkyl, iii) $C_{3-8}$-cycloalkyl-$C_{1-6}$-alkyl,
iv) $C_{3-8}$-cycloalkyl-$C_{1-6}$-alkoxy,
v) $C_{3-8}$-cycloalkoxy,
vi) $C_{3-8}$-cycloalkoxy-$C_{1-6}$-alkyl,
vii) tetrazolylmethyl,
viii) triazolylmethyl,
ix) pyrazolylmethyl,
x) $C_{1-6}$-alkyltetrazolylmethyl,
xi) $C_{1-6}$-alkyltriazolylmethyl,
xii) $C_{1-6}$-alkylpyrazolylmethyl,
xiii) heterocycloalkyl-$C_{1-6}$-alkoxy, and
xiv) cyano;
$R^4$ is selected from
i) halogen,
ii) hydroxy,
iii) cyano,
iv) $C_{1-6}$-alkyl,
v) $C_{1-6}$-alkoxy,
vi) $C_{1-6}$-alkoxy-$C_{1-6}$-alkyl,
vii) halo-$C_{1-6}$-alkoxy,
viii) halo-$C_{1-6}$-alkyl,
ix) hydroxy-$C_{1-6}$-alkyl,
x) $C_{3-8}$-cycloalkyl,
xi) $C_{3-8}$-cycloalkyl-$C_{1-6}$-alkyl,
xii) $C_{3-8}$-cycloalkyl-$C_{1-6}$-alkoxy,
xiii) $C_{3-8}$-cycloalkoxy,
xiv) $C_{3-8}$-cycloalkoxy-$C_{1-6}$-alkyl,
xv) $C_{1-6}$-alkylcarbonylamino, and
xvi) $C_{3-8}$-cycloalkylcarbonylamino,
$R^5$ is selected from
i) H,
ii) halogen,
iii) hydroxy,
iv) cyano,
v) $C_{1-6}$-alkyl,
vi) $C_{1-6}$-alkoxy,
vii) $C_{1-6}$-alkoxy-$C_{1-6}$-alkyl,
viii) halo-$C_{1-6}$-alkoxy,
ix) halo-$C_{1-6}$-alkyl,
x) hydroxy-$C_{1-6}$-alkyl,
xi) $C_{3-8}$-cycloalkyl,
xii) $C_{3-8}$-cycloalkyl-$C_{1-6}$-alkyl,
xiii) $C_{3-8}$-cycloalkyl-$C_{1-6}$-alkoxy,
xiv) $C_{3-8}$-cycloalkoxy,
xv) $C_{3-8}$-cycloalkoxy-$C_{1-6}$-alkyl,
xvi) $C_{1-6}$-alkylcarbonylamino, and
xvii) $C_{3-8}$-cycloalkylcarbonylamino,
$R^6$ is aminosulfonyl;
$R^7$ and $R^8$ are independently selected from
i) H,
ii) halogen,
iii) hydroxy,
iv) cyano,
v) $C_{1-6}$-alkyl,
vi) $C_{1-6}$-alkoxy,
vii) $C_{1-6}$-alkoxy-$C_{1-6}$-alkyl,
viii) halo-$C_{1-6}$-alkoxy,
ix) halo-$C_{1-6}$-alkyl,
x) hydroxy-$C_{1-6}$-alkyl,
xi) $C_{3-8}$-cycloalkyl,
xii) $C_{3-8}$-cycloalkyl-$C_{1-6}$-alkyl,
xiii) $C_{3-8}$-cycloalkyl-$C_{1-6}$-alkoxy,
xiv) $C_{3-8}$-cycloalkoxy, and
xv) $C_{3-8}$-cycloalkoxy-$C_{1-6}$-alkyl;

$R^9$ and $R^{10}$ are independently selected from
i) H,
ii) $C_{1-6}$-alkyl, and
iii) $C_{3-8}$-cycloalkyl;
m and n are independently zero, 1, 2, 3, 4 or 5, with the proviso that the sum of m and n is 2, 3, 4 or 5;
p is zero, 1 or 2;
q is zero or 2; and
r is zero or 1;
or a pharmaceutically acceptable salt thereof.

2. The compound according to claim 1, wherein
$R^1$ is selected from
i) phenyl substituted by $R^3$, $R^4$ and $R^5$, and
ii) pyridinyl substituted by $R^3$, $R^4$ and $R^5$;
X is selected from
i) N, and
ii) CH;
Y is selected from
i) —CH$_2$—OC(O)—, and
ii) —(CH$_2$)$_q$C(O)—;
W is selected from
i) —(CR$^9$R$^{10}$)$_p$—,
ii) —(CR$^9$R$^{10}$)$_p$—C(O)—,
iii) —(CR$^9$R$^{10}$)$_p$—O—,
iv) —(CR$^9$R$^{10}$)$_p$—S—,
v) —(CR$^9$R$^{10}$)$_p$—S(O)—, and
vi) —(CR$^9$R$^{10}$)$_p$—S(O)$_2$—;
$R^2$ is selected from
i) substituted phenyl, wherein the phenyl ring is substituted by $R^6$, $R^7$ and $R^8$,
ii) substituted pyridinyl, wherein the pyridinyl ring is substituted by $R^6$, $R^7$ and $R^8$,
iii) substituted thiophenyl, wherein the thiophenyl ring is substituted by $R^6$, $R^7$ and $R^8$, and
iv) substituted thiazolyl, wherein the thiazolyl ring is substituted by $R^6$, $R^7$ and $R^8$;
$R^3$ is selected from
i) halo-$C_{1-6}$-alkoxy,
ii) cyano,
iii) $C_{3-8}$-cycloalkyl-$C_{1-6}$-alkoxy,
iv) $C_{3-8}$-cycloalkoxy,
v) $C_{1-6}$-alkyltetrazolylmethyl, and
vi) tetrahydropyranyl-$C_{1-6}$-alkoxy;
$R^4$ is selected from
i) halogen,
ii) cyano,
iii) halo-$C_{1-6}$-alkoxy,
iv) halo-$C_{1-6}$-alkyl,
v) $C_{3-8}$-cycloalkyl, and
vi) $C_{1-6}$-alkylcarbonylamino;
$R^5$ is H;
$R^6$ is aminosulfonyl;
$R^7$ and $R^8$ are independently selected from
i) H, and
ii) halogen;
$R^9$ and $R^{10}$ are both H;
m is selected from zero, 1 and 2, and n is selected from 1, 2 and 3, with the proviso that the sum of m and n is 2, 3, 4 or 5;
p is zero, 1 or 2; and
q is zero or 2;
or a pharmaceutically acceptable salt thereof.

3. The compound of claim 1, or a pharmaceutically acceptable salt thereof, wherein $R^1$ is selected from
i) phenyl substituted by $R^3$, $R^4$ and $R^5$, and
ii) pyridinyl substituted by $R^3$, $R^4$ and $R^5$.

4. The compound according to claim 1, or a pharmaceutically acceptable salt thereof, wherein $R^1$ is phenyl substituted by $R^3$, $R^4$ and $R^5$.

5. The compound according to claim 1, or a pharmaceutically acceptable salt thereof, wherein Y is selected from
   i) —$CH_2$—OC(O)—, and
   ii) —$(CH_2)_q$C(O)—.

6. The compound according to claim 1, or a pharmaceutically acceptable salt thereof, wherein Y is —$(CH_2)_q$C(O)—.

7. The compound according to claim 1, or a pharmaceutically acceptable salt thereof, wherein W is selected from
   i) —$(CR^9R^{10})_p$—,
   ii) —$(CR^9R^{10})_p$—S—, and
   iii) —$(CR^9R^{10})_p$—S(O)$_2$—.

8. The compound according to claim 1, or a pharmaceutically acceptable salt thereof, wherein $R^1$ is selected from
   i) substituted phenyl, wherein the phenyl ring is substituted by $R^6$, $R^7$ and $R^8$, and
   ii) substituted pyridinyl, wherein the pyridinyl ring is substituted by $R^6$, $R^7$ and $R^8$.

9. The compound according to claim 1, or a pharmaceutically acceptable salt thereof, wherein $R^3$ is selected from
   i) halo-$C_{1-6}$-alkoxy,
   ii) cyano,
   iii) $C_{3-8}$-cycloalkyl-$C_{1-6}$-alkoxy,
   iv) $C_{3-8}$-cycloalkoxy,
   v) $C_{1-6}$-alkyltetrazolylmethyl, and
   vi) tetrahydropyranyl-$C_{1-6}$-alkoxy.

10. The compound according to claim 1, or a pharmaceutically acceptable salt thereof, wherein $R^3$ is selected from
    i) $C_{1-6}$-alkyltetrazolylmethyl, and
    ii) tetrahydropyranyl-$C_{1-6}$-alkoxy.

11. The compound according to claim 1, or a pharmaceutically acceptable salt thereof, wherein $R^4$ is selected from
    i) halogen,
    ii) cyano,
    iii) halo-$C_{1-6}$-alkoxy,
    iv) halo-$C_{1-6}$-alkyl,
    v) $C_{3-8}$-cycloalkyl, and
    vi) $C_{1-6}$-alkylcarbonylamino.

12. The compound according to claim 1, or a pharmaceutically acceptable salt thereof, wherein $R^4$ is selected from
    i) halo-$C_{1-6}$-alkyl, and
    ii) $C_{3-8}$-cycloalkyl.

13. The compound according to claim 1, or a pharmaceutically acceptable salt thereof, wherein $R^5$ is H.

14. The compound according to claim 1, or a pharmaceutically acceptable salt thereof, wherein $R^7$ and $R^8$ are independently selected from
    i) H, and
    ii) halogen.

15. The compound according to claim 1, or a pharmaceutically acceptable salt thereof, wherein $R^7$ is halogen.

16. The compound according to claim 1, or a pharmaceutically acceptable salt thereof, wherein $R^8$ is selected from
    i) H, and
    ii) halogen.

17. The compound according to claim 1, or a pharmaceutically acceptable salt thereof, wherein $R^9$ and $R^{10}$ are both H.

18. The compound according to claim 1, or a pharmaceutically acceptable salt thereof, wherein m is selected from zero, 1 and 2; and n is selected from 1, 2 and 3 with the proviso that the sum of m and n is 2, 3, 4 or 5.

19. The compound according to claim 1, or a pharmaceutically acceptable salt thereof, wherein m and n are both 2.

20. The compound according to claim 1, or a pharmaceutically acceptable salt thereof, wherein p is zero or 1.

21. The compound according to claim 1, or a pharmaceutically acceptable salt thereof, wherein p is zero.

22. The compound according to claim 1, or a pharmaceutically acceptable salt thereof, wherein q is 2.

23. A compound selected from the group consisting of:
    2-((5-methyl-2H-tetrazol-2-yl)methyl)-4-(trifluoromethyl)benzyl 4-(2-fluoro-4-sulfamoylphenyl)piperazine-1-carboxylate;
    [2-cyclopropyl-6-(oxan-4-ylmethoxy)pyridin-4-yl] methyl 4-[(4-sulfamoylphenyl)methyl]piperidine-1-carboxylate;
    [5-cyano-3-(2,2-dimethylpropanoylamino)pyridin-2-yl] methyl 4-[(4-sulfamoylphenyl)methyl]piperidine-1-carboxylate;
    [5-chloro-3-[(5-methyltetrazol-2-yl)methyl]pyridin-2-yl] methyl 4-(2-fluoro-4-sulfamoylphenyl)sulfonylpiperidine-1-carboxylate;
    [2-[(5-methyltetrazol-2-yl)methyl]-4-(trifluoromethyl) phenyl]methyl 4-(2-fluoro-4-sulfamoylphenyl)sulfonylpiperidine-1-carboxylate;
    2-fluoro-4-[[4-[3-[2-[(5-methyltetrazol-2-yl)methyl]-4-(trifluoromethyl)phenyl]propanoyl]piperazin-1-yl] methyl]benzenesulfonamide;
    3-fluoro-4-[[4-[3-[2-[(5-methyltetrazol-2-yl)methyl]-4-(trifluoromethyl)phenyl]propanoyl]piperazin-1-yl] methyl]benzenesulfonamide;
    4-[[4-[2-cyclopropyl-6-(oxan-4-ylmethoxy)pyridine-4-carbonyl]piperazin-1-yl]methyl]-3-fluorobenzenesulfonamide;
    3-fluoro-4-[4-[3-[2-[(5-methyltetrazol-2-yl)methyl]-4-(trifluoromethyl)phenyl]propanoyl]piperazine-1-carbonyl]benzenesulfonamide;
    2-fluoro-4-[4-[3-[2-[(5-methyltetrazol-2-yl)methyl]-4-(trifluoromethyl)phenyl]propanoyl]piperazine-1-carbonyl]benzenesulfonamide;
    3,5-difluoro-4-[4-[3-[2-[(5-methyltetrazol-2-yl)methyl]-4-(trifluoromethyl)phenyl]propanoyl]piperazine-1-carbonyl]benzenesulfonamide;
    3-fluoro-4-[4-[3-[2-[(5-methyltetrazol-2-yl)methyl]-4-(trifluoromethyl)phenyl]propanoyl]piperazine-1-carbonyl]benzenesulfonamide;
    4-(4-(3-methyl-2H-tetrazol-2-yl)methyl)-4-(trifluoromethyl)phenyl)propanoyl)piperazine-1-carbonyl)benzenesulfonamide;
    3-[[1-[2-cyclopropyl-6-(oxan-4-ylmethoxy)pyridine-4-carbonyl]piperidin-4-yl]methyl]-4-fluorobenzenesulfonamide;
    3-fluoro-4-[1-[3-[2-[(5-methyltetrazol-2-yl)methyl]-4-(trifluoromethyl)phenyl]propanoyl]piperidin-4-yl]sulfanylbenzenesulfonamide;
    3-fluoro-4-(4-(3-methyl-2H-tetrazol-2-yl)methyl)-4-(trifluoromethyl)phenyl)propanoyl)piperazin-1-yl)benzenesulfonamide;
    4-[[1-[2-cyclopropyl-6-(oxan-4-ylmethoxy)pyridine-4-carbonyl]piperidin-4-yl]methyl]benzenesulfonamide;
    4-[[1-[3-[2-[(5-methyltetrazol-2-yl)methyl]-4-(trifluoromethyl)phenyl]propanoyl]piperidin-4-yl]methyl] benzenesulfonamide;

4-[[1-[3-[2-[(5-methyltetrazol-2-yl)methyl]-4-(trifluoromethyl)phenyl]propanoyl]pyrrolidin-2-yl]methoxy]benzenesulfonamide;

4-[[1-[3-[2-[(5-methyltetrazol-2-yl)methyl]-4-(trifluoromethyl)phenyl]propanoyl]pyrrolidin-3-yl]methoxy]benzenesulfonamide;

4-(1-(3-(2-((5-methyl-2H-tetrazol-2-yl)methyl)-4-(trifluoromethyl)phenyl)propanoyl)piperidin-4-yl)benzenesulfonamide;

4-(4-(3-methyl-2H-tetrazol-2-yl)methyl)-4-(trifluoromethyl)phenyl)propanoyl)piperazin-1-yl)benzenesulfonamide;

4-fluoro-3-[[1-[3-[2-[(5-methyltetrazol-2-yl)methyl]-4-(trifluoromethyl)phenyl]propanoyl]piperidin-4-yl]methyl]benzenesulfonamide;

2,3-difluoro-4-[1-[3-[2-[(5-methyltetrazol-2-yl)methyl]-4-(trifluoromethyl)phenyl]propanoyl]piperidin-4-yl]sulfanylbenzenesulfonamide;

2,3-difluoro-4-[1-[3-[2-[(5-methyltetrazol-2-yl)methyl]-4-(trifluoromethyl)phenyl]propanoyl]piperidin-4-yl]sulfinylbenzenesulfonamide;

2,3-difluoro-4-[1-[3-[2-[(5-methyltetrazol-2-yl)methyl]-4-(trifluoromethyl)phenyl]propanoyl]piperidin-4-yl]sulfonylbenzenesulfonamide;

2,3-difluoro-4-[2-[1-[3-[2-[(5-methyltetrazol-2-yl)methyl]-4-(trifluoromethyl)phenyl]propanoyl]piperidin-4-yl]ethyl sulfonyl]benzenesulfonamide;

2-[1-[3-[2-[(5-methyltetrazol-2-yl)methyl]-4-(trifluoromethyl)phenyl]propanoyl]piperidin-4-yl]sulfanyl-1,3-thiazole-5-sulfonamide;

2-[1-[3-[2-[(5-methyltetrazol-2-yl)methyl]-4-(trifluoromethyl)phenyl]propanoyl]piperidin-4-yl]sulfonyl-1,3-thiazole-5-sulfonamide;

2-[2-[1-[3 [(5-methyltetrazol-2-yl)methyl]-4-(trifluoromethyl)phenyl]propanoyl]piperidin-4-yl]ethylsulfinyl]-1,3-thiazole-5-sulfonamide;

3-fluoro-4-[[1-[3-[2-[(5-methyltetrazol-2-yl)methyl]-4-(trifluoromethyl)phenyl]propanoyl]piperidin-4-yl]methyl sulfanyl]benzenesulfonamide;

3-fluoro-4-[[1-[3-[2-[(5-methyltetrazol-2-yl)methyl]-4-(trifluoromethyl)phenyl]propanoyl]piperidin-4-yl]methyl sulfinyl]benzenesulfonamide;

3-fluoro-4-[[1-[3-[2-[(5-methyltetrazol-2-yl)methyl]-4-(trifluoromethyl)phenyl]propanoyl]piperidin-4-yl]methyl sulfonyl]benzenesulfonamide;

3-fluoro-4-[1-[3-[2-[(5-methyltetrazol-2-yl)methyl]-4-(trifluoromethyl)phenyl]propanoyl]azetidin-3-yl]sulfanylbenzenesulfonamide;

3-fluoro-4-[1-[3-[2-[(5-methyltetrazol-2-yl)methyl]-4-(trifluoromethyl)phenyl]propanoyl]azetidin-3-yl]sulfinylbenzenesulfonamide;

3-fluoro-4-[1-[3-[2-[(5-methyltetrazol-2-yl)methyl]-4-(trifluoromethyl)phenyl]propanoyl]azetidin-3-yl]sulfonylbenzenesulfonamide;

3-fluoro-4-[1-[3-[2-[(5-methyltetrazol-2-yl)methyl]-4-(trifluoromethyl)phenyl]propanoyl]piperidin-4-yl]sulfinylbenzenesulfonamide;

3-fluoro-4-[1-[3-[2-[(5-methyltetrazol-2-yl)methyl]-4-(trifluoromethyl)phenyl]propanoyl]piperidin-4-yl]sulfonylbenzenesulfonamide;

3-fluoro-4-[2-[1-[3-[2-[(5-methyltetrazol-2-yl)methyl]-4-(trifluoromethyl)phenyl]propanoyl]piperidin-4-yl]ethyl sulfanyl]benzenesulfonamide;

3-fluoro-4-[2-[1-[3-[2-[(5-methyltetrazol-2-yl)methyl]-4-(trifluoromethyl)phenyl]propanoyl]piperidin-4-yl]ethyl sulfinyl]benzenesulfonamide;

3-fluoro-4-[2-[1-[3-[2-[(5-methyltetrazol-2-yl)methyl]-4-(trifluoromethyl)phenyl]propanoyl]piperidin-4-yl]ethyl sulfonyl]benzenesulfonamide;

3-fluoro-4-[2-[1-[6-(2,2,2-trifluoroethoxy)-5-(trifluoromethyl)pyridine-3-carbonyl]piperidin-4-yl]ethyl sulfonyl]benzenesulfonamide;

3-fluoro-4-[4-[3-[2-[(5-methyltetrazol-2-yl)methyl]-4-(trifluoromethyl)phenyl]propanoyl]piperazin-1-yl]sulfonylbenzenesulfonamide;

4-[[1-[2-cyclopropyl-6-(oxan-4-ylmethoxy)pyridine-4-carbonyl]piperidin-4-yl]methylsulfanyl]-3-fluorobenzenesulfonamide;

4-[[1-[2-cyclopropyl-6-(oxan-4-ylmethoxy)pyridine-4-carbonyl]piperidin-4-yl]methylsulfinyl]-3-fluorobenzenesulfonamide;

4-[[1-[2-cyclopropyl-6-(oxan-4-ylmethoxy)pyridine-4-carbonyl]piperidin-4-yl]methylsulfonyl]-3-fluorobenzenesulfonamide;

4-[1-(6-cyclobutyloxy-5-cyclopropylpyridine-3-carbonyl)piperidin-4-yl]sulfonyl-3-fluorobenzenesulfonamide;

4-[1-[2-cyclopropyl-6-(oxan-4-ylmethoxy)pyridine-4-carbonyl]azetidin-3-yl]sulfanyl-3-fluorobenzenesulfonamide;

4-[1-[2-cyclopropyl-6-(oxan-4-ylmethoxy)pyridine-4-carbonyl]azetidin-3-yl]sulfinyl-3-fluorobenzenesulfonamide;

4-[1-[2-cyclopropyl-6-(oxan-4-ylmethoxy)pyridine-4-carbonyl]azetidin-3-yl]sulfonyl-3-fluorobenzenesulfonamide;

4-[1-[2-cyclopropyl-6-(oxan-4-ylmethoxy)pyridine-4-carbonyl]piperidin-4-yl]sulfonyl-2,3-difluorobenzenesulfonamide;

4-[1-[2-cyclopropyl-6-(oxan-4-ylmethoxy)pyridine-4-carbonyl]piperidin-4-yl]sulfonyl-3-fluorobenzenesulfonamide;

4-[1-[3-[4-chloro-2-[(5-methyltetrazol-2-yl)methyl]phenyl]propanoyl]piperidin-4-yl]sulfonyl-3-fluorobenzenesulfonamide;

4-[1-[3-[4-cyano-2-[(5-methyltetrazol-2-yl)methyl]phenyl]propanoyl]piperidin-4-yl]sulfonyl-3-fluorobenzenesulfonamide;

4-[2-[1-[2-cyclopropyl-6-(oxan-4-ylmethoxy)pyridine-4-carbonyl]piperidin-4-yl]ethylsulfanyl]-3-fluorobenzenesulfonamide;

4-[2-[1-[2-cyclopropyl-6-(oxan-4-ylmethoxy)pyridine-4-carbonyl]piperidin-4-yl]ethylsulfinyl]-3-fluorobenzenesulfonamide;

4-[2-[1-[2-cyclopropyl-6-(oxan-4-ylmethoxy)pyridine-4-carbonyl]piperidin-4-yl]ethylsulfonyl]-3-fluorobenzenesulfonamide;

4-[2-[1-[5-cyclopropyl-6-(cyclopropylmethoxy)pyridine-3-carbonyl]piperidin-4-yl]ethylsulfonyl]-3-fluorobenzenesulfonamide;

4-[4-[2-cyclopropyl-6-(oxan-4-ylmethoxy)pyridine-4-carbonyl]piperazin-1-yl]sulfonyl-3-fluorobenzenesulfonamide;

4-[4-[3-[2-[(5-methyltetrazol-2-yl)methyl]-4-(trifluoromethyl)phenyl]propanoyl]piperazin-1-yl]sulfonylbenzenesulfonamide;

5-[1-[3-[2-[(5-methyltetrazol-2-yl)methyl]-4-(trifluoromethyl)phenyl]propanoyl]piperidin-4-yl]sulfanylthiophene-2-sulfonamide;

5-[2-[1-[3-[2-[(5-methyltetrazol-2-yl)methyl]-4-(trifluoromethyl)phenyl]propanoyl]piperidin-4-yl]ethylsulfonyl]thiophene-2-sulfonamide;

5-fluoro-6-[1-[3-[2-[(5-methyltetrazol-2-yl)methyl]-4-(trifluoromethyl)phenyl]propanoyl]piperidin-4-yl]sulfanylpyridine-3-sulfonamide;
6-[1-[2-cyclopropyl-6-(oxan-4-ylmethoxy)pyridine-4-carbonyl]piperidin-4-yl]sulfanyl-5-fluoropyridine-3-sulfonamide;
4-[1-[3-[4-(difluoromethoxy)-2-[(5-methyltetrazol-2-yl)methyl]phenyl]propanoyl]piperidin-4-yl]sulfonyl-3-fluorobenzenesulfonamide;
4-[2-[1-[3-[4-(difluoromethoxy)-2-[(5-methyltetrazol-2-yl)methyl]phenyl]propanoyl]piperidin-4-yl]ethyl sulfinyl]-2,3-difluorobenzenesulfonamide;
2,3-difluoro-4-[2-[1-[3-[2-[(5-methyltetrazol-2-yl)methyl]-4-(trifluoromethyl)phenyl]propanoyl]piperidin-4-yl]ethyl sulfinyl]benzenesulfonamide;
2-[2-[1-[3-[4-(difluoromethoxy)-2-[(5-methyltetrazol-2-yl)methyl]phenyl]propanoyl]piperidin-4-yl]ethyl sulfinyl]-1,3-thiazole-5-sulfonamide;
2-[2-[1-[3-[2-[(5-methyltetrazol-2-yl)methyl]-4-(trifluoromethyl)phenyl]propanoyl]piperidin-4-yl]ethyl sulfonyl]-1,3-thiazole-5-sulfonamide;
(+)-3-fluoro-4-[[1-[3-[2-[(5-methyltetrazol-2-yl)methyl]-4-(trifluoromethyl)phenyl]propanoyl]piperidin-4-yl]sulfinyl]benzenesulfonamide;
(+)-4-[[1-[3-[2-[(5-methyltetrazol-2-yl)methyl]-4-(trifluoromethyl)phenyl]propanoyl]pyrrolidin-2-yl]methoxy]benzenesulfonamide;
(+)-4-[[1-[3-[2-[(5-methyltetrazol-2-yl)methyl]-4-(trifluoromethyl)phenyl]propanoyl]pyrrolidin-3-yl]methoxy]benzenesulfonamide;
(−)-3-fluoro-4-[[1-[3-[2-[(5-methyltetrazol-2-yl)methyl]-4-(trifluoromethyl)phenyl]propanoyl]piperidin-4-yl]sulfinyl]benzenesulfonamide;
(−)-4-[[1-[3 [(5-methyltetrazol-2-yl)methyl]-4-(trifluoromethyl)phenyl]propanoyl]pyrrolidin-2-yl]methoxy]benzenesulfonamide;
(−)-4-[[1-[3 [(5-methyltetrazol-2-yl)methyl]-4-(trifluoromethyl)phenyl]propanoyl]pyrrolidin-3-yl]methoxy]benzenesulfonamide; and
4-((4-(3-(2-((5-methyl-2H-tetrazol-2-yl)methyl)-4-(trifluoromethyl)phenyl)propanoyl)piperazin-1-yl)methyl)benzenesulfonamide;
or a pharmaceutically acceptable salt thereof.

24. A compound selected from the group consisting of:
3-fluoro-4-[[4-[3-[2-[(5-methyltetrazol-2-yl)methyl]-4-(trifluoromethyl)phenyl]propanoyl]piperazin-1-yl]methyl]benzenesulfonamide;
2,3-difluoro-4-[1-[3-[2-[(5-methyltetrazol-2-yl)methyl]-4-(trifluoromethyl)phenyl]propanoyl]piperidin-4-yl]sulfonylbenzenesulfonamide;
3-fluoro-4-[1-[3-[2-[(5-methyltetrazol-2-yl)methyl]-4-(trifluoromethyl)phenyl]propanoyl]piperidin-4-yl]sulfonylbenzenesulfonamide;
3-fluoro-4-[4-[3-[2-[(5-methyltetrazol-2-yl)methyl]-4-(trifluoromethyl)phenyl]propanoyl]piperazin-1-yl]sulfonylbenzenesulfonamide;
4-[1-[2-cyclopropyl-6-(oxan-4-ylmethoxy)pyridine-4-carbonyl]piperidin-4-yl]sulfonyl-2,3-difluorobenzenesulfonamide;
4-[1-[2-cyclopropyl-6-(oxan-4-ylmethoxy)pyridine-4-carbonyl]piperidin-4-yl]sulfonyl-3-fluorobenzenesulfonamide; and
5-fluoro-6-[1-[3-[2-[(5-methyltetrazol-2-yl)methyl]-4-(trifluoromethyl)phenyl]propanoyl]piperidin-4-yl]sulfanylpyridine-3-sulfonamide;
or a pharmaceutically acceptable salt thereof.

25. A process to prepare a compound according to claim 1, or a pharmaceutically acceptable salt thereof, comprising the reaction of a compound of formula (II) in the presence of a compound of formula (III):

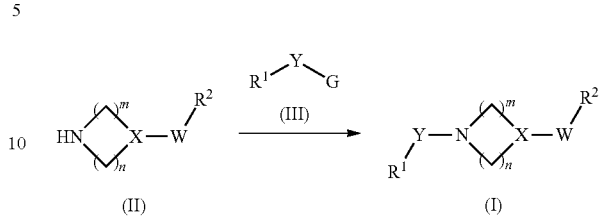

wherein $R^1$, $R^2$, Y, W, X, m and n are as defined for formula (I),
and wherein when Y is $-(CH_2)_qC(O)-$, $-(CH=CH)_r-C(O)-$ or $-(CH\equiv CH)_r-C(O)-$, then G is halogen or hydroxyl;
and wherein when Y is $-OC(O)-$, then G is chloro.

26. A pharmaceutical composition comprising a compound according to claim 1, or a pharmaceutically acceptable salt thereof, and a therapeutically inert carrier.

27. A method for the treatment of an ocular condition, which method comprises administering an effective amount of a compound according to claim 1, or a pharmaceutically acceptable salt thereof.

28. A compound according to claim 1, or a pharmaceutically acceptable salt thereof, when manufactured according to a process comprising the reaction of a compound of formula (II) in the presence of a compound of formula (III):

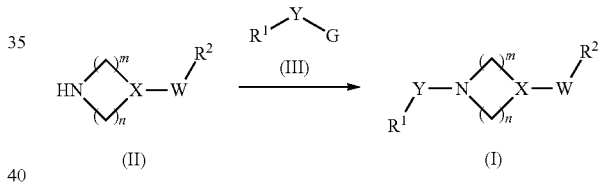

wherein $R^1$, $R^2$, Y, W, X, m and n are as defined for formula (I),
and wherein when Y is $-(CH_2)_qC(O)-$, $-(CH=CH)_r-C(O)-$ or $-(CH\equiv CH)_r-C(O)-$, then G is halogen or hydroxyl;
and wherein when Y is $-OC(O)-$, then G is chloro.

29. A pharmaceutical composition comprising a compound according to claim 23, or a pharmaceutically acceptable salt thereof, and a therapeutically inert carrier.

30. A pharmaceutical composition comprising a compound according to claim 24, or a pharmaceutically acceptable salt thereof, and a therapeutically inert carrier.

31. A method for the treatment of an ocular condition, which method comprises administering an effective amount of a compound according to claim 23, or a pharmaceutically acceptable salt thereof.

32. A method for the treatment of an ocular condition, which method comprises administering an effective amount of a compound according to claim 24, or a pharmaceutically acceptable salt thereof.

33. The method of claim 27, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

34. The method of claim 31, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

35. The method of claim 32, wherein the ocular condition is proliferative retinopathy, non-proliferative (diabetic) retinopathy, dry macular degeneration, wet age-related macular degeneration (AMD), macular edema, central arterial occlusion, central venous occlusion, traumatic injury, or glaucoma.

* * * * *